US009555096B2

(12) United States Patent
Bublot et al.

(10) Patent No.: US 9,555,096 B2
(45) Date of Patent: *Jan. 31, 2017

(54) RECOMBINANT HVT VECTORS EXPRESSING ANTIGENS OF AVIAN PATHOGENS AND USES THEREOF

(71) Applicant: Merial Inc., Duluth, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US)

(73) Assignee: MERIAL, INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,419

(22) Filed: Jun. 23, 2015

(65) Prior Publication Data

US 2015/0283225 A1    Oct. 8, 2015

Related U.S. Application Data

(63) Continuation of application No. 13/689,625, filed on Nov. 29, 2012, now Pat. No. 9,114,108.

(60) Provisional application No. 61/694,957, filed on Aug. 30, 2012, provisional application No. 61/564,877, filed on Nov. 30, 2011.

(51) Int. Cl.
| | |
|---|---|
| *A61K 39/17* | (2006.01) |
| *A61K 39/12* | (2006.01) |
| *C12N 7/00* | (2006.01) |
| *C12N 15/86* | (2006.01) |
| *A61K 39/00* | (2006.01) |

(52) U.S. Cl.
CPC ............... *A61K 39/17* (2013.01); *A61K 39/12* (2013.01); *C12N 7/00* (2013.01); *C12N 15/86* (2013.01); *A61K 2039/5256* (2013.01); *A61K 2039/552* (2013.01); *A61K 2039/70* (2013.01); *C12N 2710/16334* (2013.01); *C12N 2710/16343* (2013.01); *C12N 2720/10034* (2013.01); *C12N 2720/10071* (2013.01); *C12N 2760/18134* (2013.01); *C12N 2760/18171* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 5,187,087 A | 2/1993 | Sondermeijer et al. | |
| 5,650,153 A | 7/1997 | Ishikawa et al. | |
| 5,853,733 A | 12/1998 | Cochran et al. | |
| 5,980,906 A * | 11/1999 | Audonnet ............ | C07K 14/005 424/199.1 |
| 6,183,753 B1 | 2/2001 | Cochran et al. | |
| 6,299,882 B1 | 10/2001 | Junker | |
| 6,866,852 B2 | 3/2005 | Saitoan et al. | |
| 9,101,598 B2 * | 8/2015 | Bublot ................. | A61K 39/295 |
| 9,114,108 B2 * | 8/2015 | Bublot ................. | A61K 39/12 |
| 2007/0212377 A1 * | 9/2007 | Okuda ................. | A61K 39/245 424/229.1 |
| 2015/0283225 A1 * | 10/2015 | Bublot ................. | A61K 39/12 424/186.1 |

FOREIGN PATENT DOCUMENTS

| | | |
|---|---|---|
| EP | 1 298 139 | 4/2003 |
| WO | WO-A-87/04463 | 7/1987 |
| WO | WO 2008/038845 | 4/2008 |

OTHER PUBLICATIONS

Taylor et al. (Journal of Virology. 1990; 64 (4): 1441-1450.*
Sequence alignment of SEQ ID No. 8 with Geneseq database access No. AAR53527, submitted 2003.*
The sequence alignment of SEQ ID No. 42 with Geneseq database access No. ABR43422, submitted 2003.*
Petherbridge et al. (Journal of Virological Methods. 2009; 158: 111-117.*
Sequence alignment of SEQ ID No. 2 with PIR_80 database access No. VGNZTE by Taylor et al J of Vir 1990.*
Bublot et al J.Comp. Path.2007,vol. 137, S81-S84, "Use of a Vectored Vaccine against Infectious Bursal Disease of Chickens in the Face of High-Titred maternally Derived Antibody".
Petherbridge, et al., J. Virol. Methods 158, 11-17, 2009, "Cloning of Gallid herpesvirus 3 (Marek's disease virus serotype-2) genome as infectious bacterial artificial chromosomes for analysis of viral gene functions".
Jarosinski, et al., J. of Virology 81, 10575-10587, 2007, "Horizontal Transmission of Marek's Disease Virus Requires $U_S2$, the $U_L13$ protein Kinase, and gC".
Jarosinski, et al., J. of Virology 84, 7911-7916, 2010, "Further analysis of Marek's disease virus horizontal transmission confirms that $U_L44$ (gC) and $U_L13$ protein kinase activity are essential, while $U_S2$ is nonessential".
Johnson et al, 2010 Avian Dis 54, 1251-1259, "Protection Against Infectious Laryngotracheitis by In Ovo Vaccination with Commercially Available Viral Vector Recombinant Vaccines".
Morgan et al 1992, Avian dis. 36, 858-70, "Protection of Chickens from Newcastle and Marek's Diseases with a Recombinant Herpesvirus of Turkeys Vaccine Expressing the Newcastle Disease Virus Fusion Protein".
Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancún, Mexico, Aug. 14-18, 2011.
U.S. Appl. No. 13/689,572, filed Dec. 2014, Bublot et al.
Singh et al., Research in Veterinary Science 89, 140-145, 2010, "Comparative efficacy of BAC-derived recombinant SB-1 vaccine and the parent wild type strain in preventing replication, shedding and disease induced by virulent Marek's disease virus".

(Continued)

*Primary Examiner* — Shanon A Foley
(74) *Attorney, Agent, or Firm* — Judy Jarecki-Black; Ruoying Chen; Merial Inc.

(57) ABSTRACT

The present invention provides recombinant herpesvirus of turkeys (HVT) vectors that contain and express antigens of avian pathogens, compositions comprising the recombinant HVT vectors, polyvalent vaccines comprising the recombinant HVT vectors and one or more wild type viruses or recombinant vectors. The present invention further provides methods of vaccination against a variety of avian pathogens and method of producing the recombinant HVT vectors.

23 Claims, 44 Drawing Sheets

(56) References Cited

OTHER PUBLICATIONS

Slacum et al, 2009, The compatibility of HVT recombinants with other Marek's disease vaccines, 58th Western Poultry Disease Conference, Sacramento, CA, USA, Mar. 23-25, p. 84.

Spatz et al, Virus Gene 42, 331-338, 2011, "Comparative genomic sequence analysis of the Marek's disease vaccine strain SB-1".

Witter et al, 1984, Avian Pathology 13, 75-92, "Polyvalent Marek's disease vaccines: safety, efficacy and protective synergism in chickens with maternal antibodies".

Database UniProt, EBI accetion No. UNIPROT: Q64957, 1996 & Vakharia et al. "Use of Polymerase chain reaction for efficient cloning of DSRNA infectious bursal disease virus", Avian Disease, vol. 36, No. 3, pp. 736-742, 1996.

Database UniPROT, EBI accession No. UNIPROT A7XL40, 2007 & Miller et al., "Antigenic differences among Newcastle disease virus strains of different genotypes used in vaccine formulation affect viral shedding after a virulent challenge", Vaccine, vol. 25, No. 41, p. 7238-7246, 2007.

Vladimir et al., "Structure and properties of a herpesvirus of turkeys recombinant in which US1, US10 and SORF3 genes have been replaced by a lacZ expression cassette", Journal of General Virology, vol. 76, No. 11, p. 2903-2907, 1995.

Bublot et al., "Use of a vectored vaccine against infectious bursal disease of chickens in the face of high-titred maternally devired antibody", Journal of Comparative Pathology, vol. 137, p. S81-S84, 2007.

* cited by examiner

Figure 1

| SEQ ID NO | Type | Gene |
|---|---|---|
| 1 | DNA | NDV-F VIId codon optimized DNA sequence |
| 2 | Protein | NDV-F protein sequence from codon-optimized VIId strain |
| 3 | DNA | NDV-F VIId wildtype sequence |
| 4 | Protein | NDV-F protein sequence from wildtype VIId strain |
| 5 | DNA | NDV-F Ca02 codon optimized DNA sequence |
| 6 | Protein | NDV-F protein sequence from codon-optimized Ca02 strain |
| 7 | DNA | IBDV DNA encoding VP2 protein |
| 8 | Protein | IBDV VP2 protein |
| 9 | DNA | SV40 promoter |
| 10 | DNA | CMV-IE promoter |
| 11 | DNA | SV40 polyA signal |
| 12 | DNA | Synthetic polyA signal |
| 13 | oligo | MB080 primer |
| 14 | oligo | MB081 primer |
| 15 | oligo | optF primer |
| 16 | oligo | VIIoptF RP primer |
| 17 | oligo | SV40promoterF primer |
| 18 | DNA | Partial plasmid pHM103+Fopt DNA sequence (for vHVT114) |
| 19 | DNA | Partial plasmid pSB1 44 cds SV FCAopt (for vSB1-009) |
| 20 | DNA | Partial plasmid pHVT US2 SV- Fopt-synPA (for vHVT306) |
| 21 | DNA | Partial plasmid pCD046+NDV-F wt (for vHVT110) |
| 22 | DNA | Partial plasmid pHM103+NDV-F wt (for vHVT111) |
| 23 | DNA | Partial plasmid pHM103 + NDV-F CA02 (for vHVT116) |
| 24 | DNA | Partial plasmid HVTIG2 SV Fwt SbfI sequence (for vHVT301) |
| 25 | DNA | Partial plasmid pHVTUS10 cds F opt plasmid (for vHVT302) |
| 26 | DNA | Partial plasmid pHVT US20 cds F CA02 opt sequence (for vHVT303) |
| 27 | DNA | Partial plasmid HVT IG2 SVFopt syn tail sequence (for vHVT304) |
| 28 | DNA | Partial plasmid pHVT US2 SV-FCA02 opt-synPA (for vHVT307) |

Genome Structure of HVT and Insertion Sites

Genomic Structure of HVT, ORFs of the *BamHI* fragment, and Insertion/Replacement Locations
(GenBank accession number for HVT FC126 sequence: AF291866.1)

Figure 3

Plasmid map of pHM103 containing codon-optimized NDV-F gene amp

Intergene 1 arm pHM103 + Fopt
7212 bp

SV40 Promoter

*Not*I (2264)

Intergene 1 arm polyA SV 40

*Not*I (3941)

NDV-FconsVIId-CSmut

Figure 1: vHVT114 Identity PCR

Lane 1: no template
Lane 2: FC126 cl2
Lane 3: vHVT114

Dual Immunofluorescent Assay

Panel A is from the pre-MSV passage
Panel B is from the pre-MSV+12 passage.

Figure 6

Southern blot using the NDV-F probe

~ 1.6

BamHI    PstI    SphI    NcoI

1 = pHM103+Fopt donor
2 = vHVT114
3 = FC126 cl2

Immunoprecipitation and Western Blot of vHVT114

Lane M: Pre-Stained Standard (SeeBlue, Invitrogen);
Lane 1: CEF;
Lane 2: vHVT114.

Western blot analysis of immunoprecipitated sample from vHVT306 infected cells

Lane M: pre-stained protein standard (Invitrogen, SeeBlue).
Lane 1: uninfected CEF,
Lane 2: vHVT306,

Figure 9

Western blot analysis of immunoprecipitated sample
from vSB1-009 infected cells

Lane M: pre-stained protein standard (Invitrogen, SeeBlue)
Lane 1: uninfected CEF
Lane 2: vSB1-009 pre-MSV stock

Figure 10

Challenge study of vHVT304 and vHVT114 against NDV ZJ1 and CA02

Figure 11
FIG. 11A
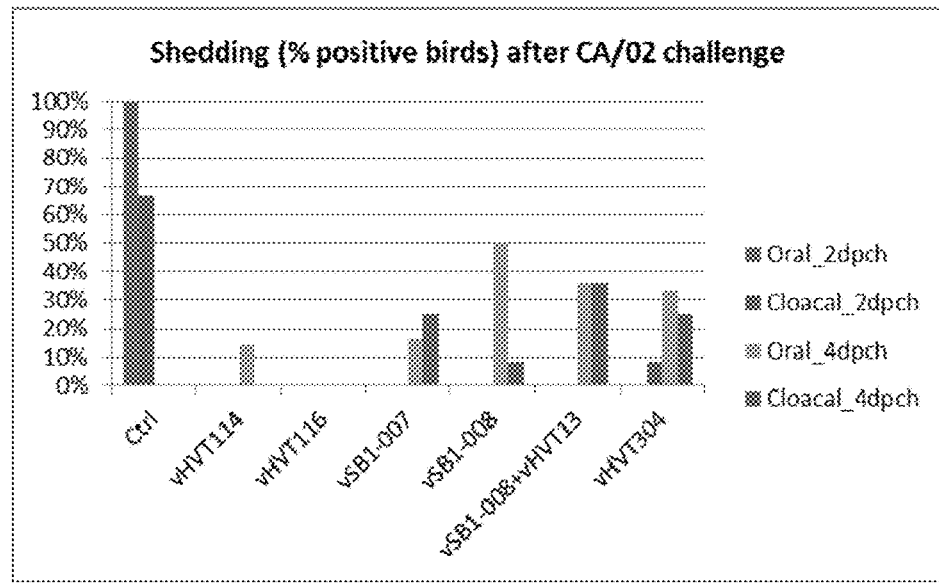
FIG. 11B
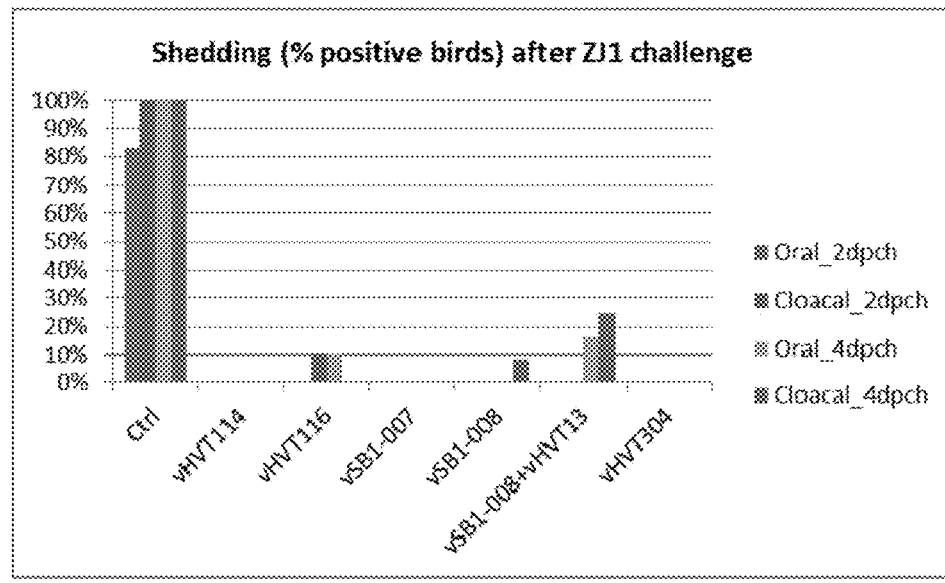

Figure 12
FIG. 12A
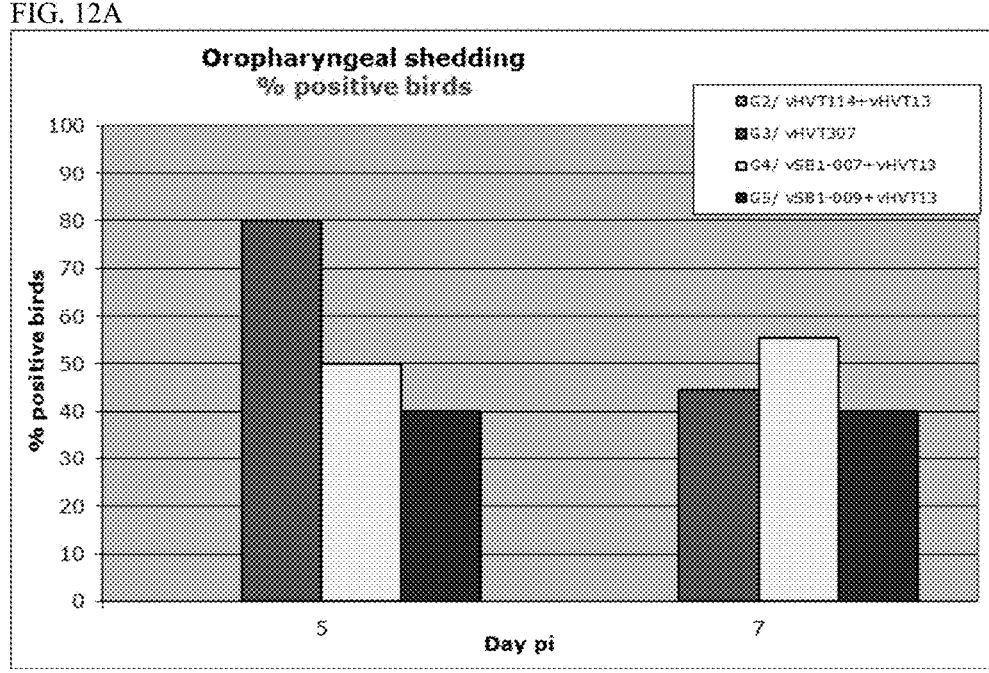
FIG. 12B
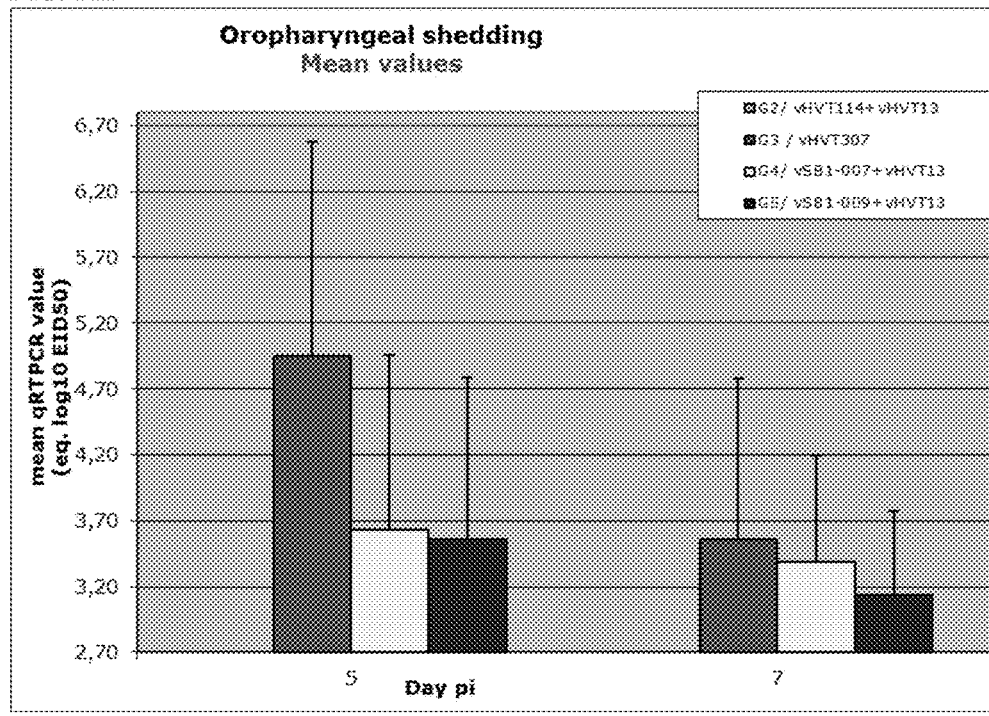

Figure 13A

Sequence alignment

```
                 1                                                50
SEQ 2    (1)   MGSKPSTRIPAPLMLITRIMLILGCIRPTSSLDGRPLAAAGIVVTGDKAV
SEQ 4    (1)   MGSKPSTRIPAPLMLITRIMLILGCIRPTSSLDGRPLAAAGIVVTGDKAV
SEQ 6    (1)   MGSKPSTWISVTLMLITRTMLILSCICPTSSLDGRPLAAAGIVVTGDKAV 51                                               100
SEQ 2   (51)   NVYTSSQTGSIIVKLLPNMPRDKEACAKAPLEAYNRTLTTLLTPLGDSIR
SEQ 4   (51)   NVYTSSQTGSIIVKLLPNMPRDKEACAKAPLEAYNRTLTTLLTPLGDSIR
SEQ 6   (51)   NIYTSSQTGSIIIKLLPNMPKDKEACAKAPLEAYNRTLTTLLTPLGDSIR 101                                              150
SEQ 2  (101)   KIQGSVSTSGGGKQGRLIGAVIGSVALGVATAAQITAAAALIQANQNAAN
SEQ 4  (101)   KIQGSVSTSGGGKQGRLIGAVIGSVALGVATAAQITAAAALIQANQNAAN
SEQ 6  (101)   RIQGSASTSGGGKQGRLVGAIIGSVALGVATAAQITAAAALIQANQNAAN 151                                              200
SEQ 2  (151)   ILRLKESIAATNEAVHEVTDGLSQLSVAVGKMQQFVNDQFNNTARELDCI
SEQ 4  (151)   ILRLKESIAATNEAVHEVTDGLSQLSVAVGKMQQFVNDQFNNTARELDCI
SEQ 6  (151)   ILRLKESIAATNDAVHEVTNGLSQLAVAVGKMQQFVNQFNNTARELDCI 201                                              250
SEQ 2  (201)   KITQQVGVELNLYLTELTTVFGPQITSPALTQLTIQALYNLAGGNMDYLL
SEQ 4  (201)   KITQQVGVELNLYLTELTTVFGPQITSPALTQLTIQALYNLAGGNMDYLL
SEQ 6  (201)   KIAQQVGVELNLYLTELTTVFGPQITSPALTQLTIQALYNLAGGNMDYLL 251                                              300
SEQ 2  (251)   TKLGIGNNQLSSLIGSGLITGYPILYDSQTQLLGIQVNLPSVGNLNNMRA
SEQ 4  (251)   TKLGIGNNQLSSLIGSGLITGYPILYDSQTQLLGIQVNLPSVGNLNNMRA
SEQ 6  (251)   TKLGVGNNQLSSLIGSGLITGNPILYDSQTQLLGIQINLPSVGSLNNMRA 301                                              350
SEQ 2  (301)   TYLETLSVSTTKGYASALVPKVVTQVGSVIEELDTSYCIESDLDLYCTRI
SEQ 4  (301)   TYLETLSVSTTKGYASALVPKVVTQVGSVIEELDTSYCIESDLDLYCTRI
SEQ 6  (301)   TYLETLSVSTTKGFASALVPKVVTQVGSVIEELDTSYCIESDIDLYCTRV 351                                              400
SEQ 2  (351)   VTFPMSPGIYSCLSGNTSACMYSKTEGALTTPYMALKGSVIANCKITTCR
SEQ 4  (351)   VTFPMSPGIYSCLSGNTSACMYSKTEGALTTPYMALKGSVIANCKITTCR
SEQ 6  (351)   VTFPMSPGIYSCLSGNTSACMYSKTEGALTTPYMALKGSVIANCKMTTCR 401                                              450
SEQ 2  (401)   CTDPPGIISQNYGEAVSLIDRHSCNVLSLDGITLRLSGEFDATYQKNISI
SEQ 4  (401)   CTDPPGIISQNYGEAVSLIDRHSCNVLSLDGITLRLSGEFDATYQKNISI
SEQ 6  (401)   CADPPGIISQNYGEAVSLIDRHSCSVLSLDGITLRLSGEFDATYQKNISI
```

Figure 13B

```
              451                                                   500
SEQ 2  (451)  LDSQVIVTGNLDISTELGNVNNSISNALDRLAESNSKLEKVNVRLTSTSA
SEQ 4  (451)  LDSQVIVTGNLDISTELGNVNNSISNALDRLAESNSKLEKVNVRLTSTSA
SEQ 6  (451)  LDSQVIVTGNLDISTELGNVNNSISSTLDKLAESNNKLNKVNVNLTSTSA 501                                                   550
SEQ 2  (501)  LITYIVLTVISLVFGALSLVLACYLMYKQKAQQKTLLWLGNNTLDQMRAT
SEQ 4  (501)  LITYIVLTVISLVFGALSLVLACYLMYKQKAQQKTLLWLGNNTLDQMRAT
SEQ 6  (501)  LITYIVLAIVSLAFGVISLVLACYLMYKQRAQQKTLLWLGNNTLDQMRAT

551
SEQ 2  (551)  TRA--
SEQ 4  (551)  TRA--
SEQ 6  (551)  TRT--
```

SEQ ID NO:2 is 100% identical to SEQ ID NO:4.
SEQ ID NO:2 is 91.5% identical to SEQ ID NO:6.
SEQ ID NO:4 is 91.5% identical to SEQ ID NO:6.

Figure 14A

DNA and protein sequences

NDV-F codon optimized DNA (SEQ ID NO:1)
atgggcagcaagcccagcacaagaatcccagcccccctgatgctgatcaccgcatcat
gctgatcctgggctgcatcagacccacaagctcctggatggacgcccctggccgctg
ccggcatcgtggtgaccggcgacaaggccgtgaacgtgtacaccagcagccagaccggc
agcatcatcgtgaagctgctgcccaacatgcccagagacaaagaggcctgcgccaaggc
ccccctggaagcctacaacagaaccctgaccaccctgctgaccccctgggcgacagca
tcagaaagatccagggctccgtgagcacaagcggcggaggaaagcagggcagactgatc
ggcgccgtgatcggcagcgtggccctggagtggctacagctgccagattaccgctgc
agccgccctgatccaggccaaccagaacgccgccaacatcctgagactgaaagagagca
ttgccgccaccaacgaggccgtgcacgaagtgaccgacggcctgagccagctgtccgtg
gccgtgggcaagatgcagcagttcgtgaacgaccagttcaacaacaccgccagagagct
ggactgcatcaagatcacccagcaggtgggcgtggagctgaacctgtacctgaccgagc
tgaccacagtgttcggccccagatcacaagcccagccctgacacagctgaccatccag
gccctgtacaacctggctggcggcaacatggactatctgctgacaaagctgggaatcgg
caacaaccagctgtccagcctgatcggaagcggcctgatcaccggctacccatcctgt
acgacagccagacacagctgctgggcatccaggtgaacctgcccagcgtgggcaacctg
aacaacatgcgcgccaccacctggaaacctgagcgtgtccaccaccaagggctacgc
cagcgccctggtgccaaggtggtgacacaggtgggcagcgtgatcgaggaactggaca
ccagctactgcatcgagagcgacctggacctgtactgcaccagaatcgtgaccttccca
atgagccccggcatctacagctgcctgagcggcaacaccagcgcctgcatgtacagcaa
gaccgaaggcgcactgacaacaccctacatggccctgaagggaagcgtgatcgccaact
gcaagatcaccacctgcagatgcaccgaccccccaggcatcatcagccagaactacgc
gaggccgtgagcctgatcgatcgccattcctgtaacgtgctgtccctggacggcatcac
actgagactgagcggcgagttcgatgccacctaccagaagaacatcagcatcctggaca
gccaggtgatcgtgaccggcaacctggacatcagcaccgagctgggcaacgtgaataac
agcatcagcaacgccctggacagactggccgagagcaacagcaagctggaaaagtgaa
cgtgcgcctgacatccacttccgctctgatcacctacatcgtgctgaccgtgatcagcc
tggtgttcggcgccctgagcctggtgctggcctgctacctgatgtacaagcagaaggcc
cagcagaaaaccctgctgtggctgggcaacaacaccctggaccagatgagagccaccac
cagagcctgatga

NDV-F protein (SEQ ID NO:2)
MGSKPSTRIPAPLMLITRIMLILGCIRPTSSLDGRPLAAAGIVVTGDKAVNVYTSSQTGSIIVKL
LPNMPRDKEACAKAPLEAYNRTLTTLLTPLGDSIRKIQGSVSTSGGGKQGRLIGAVIGSVALGVA
TAAQITAAAALIQANQNAANILRLKESIAATNEAVHEVTDGLSQLSVAVGKMQQFVNDQFNNTAR
ELDCIKITQQVGVELNLYLTELTTVFGPQITSPALTQLTIQALYNLAGGNMDYLLTKLGIGNNQL
SSLIGSGLITGYPILYDSQTQLLGIQVNLPSVGNLNNMRATYLETLSVSTTKGYASALVPKVVTQ
VGSVIEELDTSYCIESDLDLYCTRIVTFPMSPGIYSCLSGNTSACMYSKTEGALTTPYMALKGSV
IANCKITTCRCTDPPGIISQNYGEAVSLIDRHSCNVLSLDGITLRLSGEFDATYQKNISILDSQV
IVTGNLDISTELGNVNNSISNALDRLAESNSKLEKVNVRLTSTSALITYIVLTVISLVFGALSLV
LACYLMYKQKAQQKTLLWLGNNTLDQMRATTRA*

Figure 14B

DNA sequence of NDV-F VIId wildtype (SEQ ID NO:3)
atgggctccaaaccttctaccaggatcccagcacctctgatgctgatcacccggattat
gctgatattgggctgtatccgtccgacaagctctcttgacggcaggcctcttgcagctg
caggaattgtagtaacaggagataaggcagtcaatgtatacacttcgtctcagacaggg
tcaatcatagtcaagttgctcccgaatatgcccagggataaggaggcgtgtgcaaaagc
cccattagaggcatataacagaacactgactactttgctcactcctcttggcgactcca
tccgcaagatccaagggtctgtgtccacatctggaggaggcaagcaaggccgcctgata
ggtgctgttattggcagtgtagctcttggggttgcaacagcggcacagataacagcagc
tgcggccctaatacaagccaaccagaatgccgccaacatcctccggcttaaggagagca
ttgctgcaaccaatgaagctgtgcatgaagtcaccgacggattatcacaactatcagtg
gcagttgggaagatgcagcagtttgtcaatgaccagtttaataatacggcgcgagaatt
ggactgtataaaaatcacacaacaggttggtgtagaactcaacctatacctaactgaat
tgactacagtattcgggccacagatcacctcccctgcattaactcagctgaccatccag
gcactttataatttagctggtggcaatatggattacttattaactaagttaggtatagg
gaacaatcaactcagctcgttaattggtagcggcctgatcactggttaccctatactgt
atgactcacagactcaactcttgggcatacaagtgaatttaccctcagtcgggaactta
aataatatgcgtgccacctatttggagaccttatctgtaagtacaaccaaaggatatgc
ctcagcacttgtcccgaaagtagtgacacaagtcggttccgtgatagaagagcttgaca
cctcatactgtatagagtccgatctggatttatattgtactagaatagtgacattcccc
atgtccccaggtatttattcctgtttgagcggcaacacatcagcttgcatgtattcaaa
gactgaaggcgcactcactacgccgtatatggcccttaaaggctcagttattgccaatt
gtaaaataacaacatgtagatgtacagaccctcctggtatcatatcgcaaaattatgga
gaagctgtatccctgatagatagacattcgtgcaatgtcttatcattagacgggataac
tctaaggctcagtggggaatttgatgcaacttatcaaaagaacatctcaatactagatt
ctcaagtcatcgtgacaggcaatcttgatatatcaactgaacttggaaacgtcaacaat
tcaatcagcaatgccttggataggttggcagaaagcaacagcaagctagaaaaagtcaa
tgtcagactaaccagcacatctgctctcattacctatattgttctaactgtcatttctc
tagttttcggtgcacttagtctggtgttagcgtgttacctgatgtacaaacagaaggca
caacaaaagaccttgctatggcttgggaataataccctcgatcagatgagagccactac
aagagcatga Amino Acid sequence of NDV-F VIId wildtype (SEQ ID NO:4)
```
  1    MGSKPSTRIP APLMLITRIM LILGCIRPTS SLDGRPLAAA GIVVTGDKAV
 51    NVYTSSQTGS IIVKLLPNMP RDKEACAKAP LEAYNRTLTT LLTPLGDSIR
101    KIQGSVSTSG GGKQGRLIGA VIGSVALGVA TAAQITAAAA LIQANQNAAN
151    ILRLKESIAA TNEAVHEVTD GLSQLSVAVG KMQQFVNDQF NNTARELDCI
201    KITQQVGVEL NLYLTELTTV FGPQITSPAL TQLTIQALYN LAGGNMDYLL
251    TKLGIGNNQL SSLIGSGLIT GYPILYDSQT QLLGIQVNLP SVGNLNNMRA
301    TYLETLSVST TKGYASALVP KVVTQVGSVI EELDTSYCIE SDLDLYCTRI
351    VTFPMSPGIY SCLSGNTSAC MYSKTEGALT TPYMALKGSV IANCKITTCR
401    CTDPPGIISQ NYGEAVSLID RHSCNVLSLD GITLRLSGEF DATYQKNISI
451    LDSQVIVTGN LDISTELGNV NNSISNALDR LAESNSKLEK VNVRLTSTSA
501    LITYIVLTVI SLVFGALSLV LACYLMYKQK AQQKTLLWLG NNTLDQMRAT
551    TRA*
```

Figure 14C

DNA sequence of NDV-F-CA02-CSmut (SEQ ID NO:5) from HVT116
atgggcagcaagcccagcacctggatcagcgtgaccctgatgctgatcaccagaaccat
gctgatcctgagctgcatctgccccacaagcagcctggacggcagacccctggccgctg
ccggcatcgtggtgaccggcgacaaggccgtgaacatctacaccagcagccagaccggc
agcatcatcatcaagctgctgcccaacatgcccaaggacaaagaggcctgcgccaaggc
ccccctggaagcctacaacagaaccctgaccaccctgctgaccccctgggcgacagca
tcagaagaatccagggcagcgccaccacaagcggcggaggaaagcagggcagactggtg
ggcgctatcatcggagcgtggccctgggcgtggccacagctgcccagattaccgctgc
agccgccctgattcaggccaatcagaacgccgccaacatcctgagactgaaagagagca
ttgccgccaccaacgacgccgtgcacgaagtgacaaacggactgtcccagctggctgtc
gctgtcggcaagatgcagcagttcgtgaacaaccagttcaacaacacgccagagagct
ggactgcatcaagatcgcccagcaggtgggcgtggagctgaacctgtacctgaccgagc
tgaccacagtgttcggcccccagatcacaagcccgctctgacccagctgacaatccag
gccctgtacaacctggctggcggcaacatggactatctgctgactaagctgggagtggg
caacaaccagctgtccagcctgatcgggtccgggctgatcacaggcaaccccatcctgt
acgacagccagacacagctgctgggcatccagatcaacctgccatccgtgggaagcctg
aacaacatgagagccacctacctggaaaccctgagcgtgtccaccaccaagggcttcgc
cagcgccctggtgcccaaggtggtgacacaggtgggcagcgtgatcgaggaactggaca
ccagctactgcatcgagagcgacatcgacctgtactgcaccagagtggtgaccttccca
atgagccccggcatctacagctgcctgagcggcaacaccagcgcctgcatgtacagcaa
gaccgaaggagcactgacaacaccctacatggccctgaagggaagcgtgatcgccaact
gcaagatgaccacctgcagatgcgccgaccccccaggcatcatcagccagaactacggc
gaggccgtgagcctgatcgacaaacattcctgtagcgtgctgtccctggatggcatcac
actgagactgagcggcgagttcgacgccacctaccagaagaacatcagcatcctggaca
gccaggtgatcgtgaccggcaacctggacatcagcaccgagctgggcaacgtgaacaac
agcatcagcagcaccctggacaagctggccgagtccaacaacaagctgaacaaagtgaa
cgtgaacctgaccagcacaagcgccctgatcacctacatcgtgctggccatcgtgtccc
tggccttcggcgtgatcagcctggtgctggcctgctacctgatgtacaagcagagagcc
cagcagaaaaccctgctgtggctgggcaataacaccctggaccagatgagggccaccac
cagaaccctgatga Amino Acid sequence of NDV-F-CA02-CSmut (SEQ ID NO:6) from
HVT116
         1  MGSKPSTWIS  VTLMLITRTM  LILSCICPTS  SLDGRPLAAA  GIVVTGDKAV
        51  NIYTSSQTGS  IIIKLLPNMP  KDKEACAKAP  LEAYNRTLTT  LLTPLGDSIR
       101  RIQGSATTSG  GGKQGRLVGA  IIGSVALGVA  TAAQITAAAA  LIQANQNAAN
       151  ILRLKESIAA  TNDAVHEVTN  GLSQLAVAVG  KMQQFVNNQF  NNTARELDCI
       201  KIAQQVGVEL  NLYLTELTTV  FGPQITSPAL  TQLTIQALYN  LAGGNMDYLL
       251  TKLGVGNNQL  SSLIGSGLIT  GNPILYDSQT  QLLGIQINLP  SVGSLNNMRA
       301  TYLETLSVST  TKGFASALVP  KVVTQVGSVI  EELDTSYCIE  SDIDLYCTRV
       351  VTFPMSPGIY  SCLSGNTSAC  MYSKTEGALT  TPYMALKGSV  IANCKMTTCR
       401  CADPPGIISQ  NYGEAVSLID  KHSCSVLSLD  GITLRLSGEF  DATYQKNISI
       451  LDSQVIVTGN  LDISTELGNV  NNSISSTLDK  LAESNNKLNK  VNVNLTSTSA
       501  LITYIVLAIV  SLAFGVISLV  LACYLMYKQR  AQQKTLLWLG  NNTLDQMRAT
       551  TRT**

Figure 14D

```
DNA coding for IBDV VP2 protein  (SEQ ID NO:7)
ATGACAAACCTGCAAGATCAAACCCAACAGATTGTTCCGTTCATACGGAGCCTTCTGAT
GCCAACAACCGGACCGGCGTCCATTCCGGACGACACCCTGGAGAAGCACACTCTCAGGT
CAGAGACCTCGACCTACAATTTGACTGTGGGGGACACAGGGTCAGGGCTAATTGTCTTT
TTCCCTGGATTCCCTGGCTCAATTGTGGGTGCTCACTACACACTGCAGAGCAATGGGAA
CTACAAGTTCGATCAGATGCTCCTGACTGCCCAGAACCTACCGGCCAGCTACAACTACT
GCAGACTAGTGAGTCGGAGTCTCACAGTGAGGTCAAGCACACTCCTGGTGGCGTTTAT
GCACTAAACGGCACCATAAACGCCGTGACCTTCCAAGGAAGCCTGAGTGAACTGACAGA
TGTTAGCTACAATGGGTTGATGTCTGCAACAGCCAACATCAACGACAAAATTGGGAATG
TCCTGGTAGGGGAAGGGGTCACTGTCCTCAGCCTACCCACATCATATGATCTTGGGTAT
GTGAGGCTTGGTGACCCCATTCCCGCTATAGGGCTTGACCCAAAAATGGTAGCTACATG
CGACAGCAGTGACAGGCCCAGAGTCTACACCATAACTGCAGCCGATGATTACCAATTCT
CATCACAGTACCAACCAGGTGGGGTAACAATCACACTGTTCTCAGCCAACATTGATGCT
ATCACAAGCCTCAGCATTGGGGAGAGCTCGTGTTTCAAACAAGCGTCCAAGGCCTTGT
ACTGGGCGCCACCATCTACCTTATAGGCTTTGATGGGACTGCGGTAATCACCAGAGCTG
TAGCCGCAGATAATGGGCTGACGGCCGGCACCGACAATCTTATGCCATTCAATCTTGTC
ATTCCAACCAATGAGATAACCCAGCCAATCACATCCATCAAACTGGAGATAGTGACCTC
CAAAAGTGGTGGTCAGGCAGGGGATCAGATGTCATGGTCGGCAAGTGGGAGCCTAGCAG
TGACGATCCATGGTGGCAACTATCCAGGGGCCCTCCGTCCCGTCACACTAGTAGCCTAC
GAAAGAGTGGCAACAGGATCCGTCGTTACGGTCGCTGGGGTGAGTAACTTCGAGCTGAT
TCCAAATCCTGAACTAGCAAAGAACCTGGTTACAGAATACGGCCGATTTGACCCAGGAG
CCATGAACTACACAAAATTGATACTGAGTGAGAGGGACCGTCTTGGCATCAAGACCGTC
TGGCCAACAAGGGAGTACACTGATTTTCGTGAGTACTTCATGGAGGTGGCCGACCTCAA
CTCTCCCCTGAAGATTGCAGGAGCATTTGGCTTCAAAGACATAATCCGGGCTATAAGGA
GGTAA
```

IBDV VP2 protein (SEQ ID NO:8)
MTNLQDQTQQIVPFIRSLLMPTTGPASIPDDTLEKHTLRSETSTYNLTVGDTGSGLIVF
FPGFPGSIVGAHYTLQSNGNYKFDQMLLTAQNLPASYNYCRLVSRSLTVRSSTLPGGVY
ALNGTINAVTFQGSLSELTDVSYNGLMSATANINDKIGNVLVGEGVTVLSLPTSYDLGY
VRLGDPIPAIGLDPKMVATCDSSDRPRVYTITAADDYQFSSQYQPGGVTITLFSANIDA
ITSLSIGGELVFQTSVQGLVLGATIYLIGFDGTAVITRAVAADNGLTAGTDNLMPFNLV
IPTNEITQPITSIKLEIVTSKSGGQAGDQMSWSASGSLAVTIHGGNYPGALRPVTLVAY
ERVATGSVVTVAGVSNFELIPNPELAKNLVTEYGRFDPGAMNYTKLILSERDRLGIKTV
WPTREYTDFREYFMEVADLNSPLKIAGAFGFKDIIRAIRR Sv40 Promoter (SEQ ID NO:9)
gaattcgagctcggtacagcttggctgtggaatgtgtgtcagttagggtgtggaaagtc
cccaggctccccagcaggcagaagtatgcaaagcatgcatctcaattagtcagcaacca
ggtgtggaaagtccccaggctccccagcaggcagaagtatgcaaagcatgcatctcaat
tagtcagcaaccatagtcccgcccctaactccgcccatcccgcccctaactccgcccag
ttccgcccattctccgcccatggctgactaatttttttatttatgcagaggccgagg
ccgcctcggcctctgagctattccagaagtagtgaggaggcttttttggaggcctaggc
ttttgcaaaaagct

Figure 14E

CMV-IE promoter (SEQ ID NO:10)
aactccgcccgttttatgactagaaccaatagttttaatgccaaatgcactgaaatcc
cctaatttgcaaagccaaacgcccctatgtgagtaatacggggactttttacccaatt
tcccaagcggaaagcccctaatacactcatatggcatatgaatcagcacggtcatgca
ctctaatggcggcccatagggactttccacatagggcgttcaccatttcccagcata
ggggtggtgactcaatggcctttacccaagtacattgggtcaatgggaggtaagccaat
gggttttcccattactggcaagcacactgagtcaaatggactttccactggttttg
cccaagtacattgggtcaatgggaggtgagccaatgggaaaacccattgctgccaagt
acactgactcaatagggactttccaatggttttccattgttggcaagcatataaggt
caatgtgggtgagtcaatagggactttccattgtattctgcccagtacataaggtcaat
aggggtgaatcaacaggaaagtcccattggagccaagtacactgcgtcaataggact
ttccattgggttttgcccagtacataaggtcaataggggatgagtcaatgggaaaaacc
cattggagccaagtacactgactcaatagggactttccattgggttttgcccagtacat
aaggtcaataggggtgagtcaacaggaaagtcccattggagccaagtacattgagtca
atagggactttccaatggttttgcccagtacataaggtcaatgggaggtaagccaatg
ggttttcccattactggcacgtatactgagtcattagggactttccaatggttttgc
ccagtacataaggtcaataggggtgaatcaacaggaaagtcccattggagccaagtaca
ctgagtcaatagggactttccattgggttttgcccagtacaaaaggtcaatagggggtg
agtcaatggttttcccattattggcacgtacataaggtcaataggggtgagtcattg
gttttccagccaatttaattaaaacgccatgtactttccaccattgacgtcaatgg
gctattgaaactaatgcaacgtgacctttaaacggtactttccatagctgattaatgg
gaaagtaccgttctcgagccaatacacgtcaatgggaagtgaaagggcagccaaaacgt
aacaccgcccggttttccctggaattccatattggcacgcattctattggctgagc
tgcgttctacgtgggtataagaggcgcgaccagcgtcggtaccgtcgcagtcttcggtc
tgaccaccgtagaacgcagagctcctcgctgcag SV40 polyA signal (SEQ ID NO:11)
Ggggatccagacatgataagatacattgatgagtttggacaaaccacaactagaatgca
gtgaaaaaaatgctttatttgtgaaatttgtgatgctattgctttatttgtaaccatta
taagctgcaataaacaagttaacaacaacaattgcattgatttatgtttcaggttcag
ggggaggtgtgggaggttttttcggatcctctagagtcgac Synthetic polyA signal  (SEQ ID NO:12)
aataaaatatctttatttcattacatctgtgtgttggttttttgtgtgaatcgatagt
actaacatacgctctccatcaaaacaaaacgaaacaaaacaaactagcaaaataggctg
tccccagtgcaagtgcaggtgccagaacatttctctt

Figure 14F

Partial plasmid pHM103+Fopt DNA sequence (SEQ ID NO:18)
        *Green and Italic* = Arms
        Black and bold = NDV Fopt
        BLUE AND UPPERCASE = SV40 PROMOTER
        *Red and Italic and underlined* = SV40 polyA

*gagctcagggtatgatactcagctgttattgtggccgaccaggaggactccaat*
*gcttagcattcataagaacgctagagatgctatttaacgatgtgctgtcgtcta*
*aagaatttgtgcatttagcctttaaatgtaaaaccaatgacgcattcactacgc*
*tcgtgcgtgcaatttctgggccagggtatgcatattccataacagaaatcgaca*
*cttgagaagaggatctgactgtttgggataaaggtcgtttgggtctgtcctagc*
*gatataatttatatgacgatatacattaaacatctgtgtgcagtacttaggtat*
*ttaatcatgtcgatgaaatgttatgtgtaaatatcggacaatatagataacggg*
*cacgctgctattgtaacgtgcgcccgcgcgctagtgctgactaatagtgtggat*
*gatgtatacagtatattacaaacggaaatgatacgtaataaattatgtactctt*
*attgatttataaaaacatacatgcagtgttgctatgtcacataattagcctcgc*
*ccgtctacgctccactgaagataatgggctcccgctgttcaaaaaaatcagcgt*
*gcgtcgataagactttggtgcagtctcttcggggtcgcaatttagatttgccgc*
*atggagggtatctggggattttgccaatgctggagcgacgactgtacgattcg*
*tcccatcgggatctagcagaccaatgatgttgacacacatcggccatgcatgta*
*cggacggtctattgcgcgagtttgttattttcgaaggacaagatggaagtgtat*
*atggaaccgacaataatgttagtttgcatttcttagggcggaatctacatgata*
*tcttatccaagcggggtatgagccagagagatgtgatggtcataaagggtaaat*
*ttttagatctgaaataacgcagttgcccaaacaacgatcgcgattaaaagaaa*
*aatcggatggttcaattaggacatgcatggattctgtgcgcataaaccataacc*
*gcagcactgttgggcacttcggtaactcaaatgcgaagcgttgcacgtctgcga*
*taactacgcctactatgcacattgttactcctgcatcttaaaatatatcctgt*
*agtaatttcacagcaatgtcataacatcatctcgctaaagaatgacctgggat*
*tggagaagtaatgaatatttgcaaccaatgcattgaataaactaacattaaac*G
AATTCGAGCTCGGTACAGCTTGGCTGTGGAATGTGTGTCAGTTAGGGTGTGGAA
AGTCCCCAGGCTCCCCAGCAGGCAGAAGTATGCAAAGCATGCATCTCAATTAGT
CAGCAACCAGGTGTGGAAAGTCCCCAGGCTCCCCAGCAGGCAGAAGTATGCAAA
GCATGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTT
TTTTTATTTATGCAGAGGCCGAGGCCGCCTCGGCCTCTGAGCTATTCCAGAAGT
AGTGAGGAGGCTTTTTTGGAGGCCTAGGCTTTTGCAAAAAGCTgcggccgccac
catgggcagcaagcccagcacaagaatcccagccccctgatgctgatcacccg
catcatgctgatcctgggctgcatcagacccacaagctccctggatggacgccc
cctggccgctgccggcatcgtggtgaccggcgacaaggccgtgaacgtgtacac
cagcagccagaccggcagcatcatcgtgaagctgctgcccaacatgcccagaga
caaagaggcctgcgccaaggccccctggaagcctacaacagaaccctgaccac
cctgctgacccccctgggcgacagcatcagaaagatccagggctccgtgagcac
aagcggcggaggaaagcagggcagactgatcggcgccgtgatcggcagcgtggc
cctgggagtggctacagctgcccagattaccgctgcagccgccctgatccaggc
caaccagaacgccgccaacatcctgagactgaaagagagcattgccgccaccaa

Figure 14G cgaggccgtgcacgaagtgaccgacggcctgagccagctgtccgtggccgtggg
caagatgcagcagttcgtgaacgaccagttcaacaacaccgccagagagctgga
ctgcatcaagatcacccagcaggtgggcgtggagctgaacctgtacctgaccga
gctgaccacagtgttcggcccccagatcacaagcccagccctgacacagctgac
catccaggccctgtacaacctggctggcggcaacatggactatctgctgacaaa
gctgggaatcggcaacaaccagctgtccagcctgatcggaagcggcctgatcac
cggctaccccatcctgtacgacagccagacacagctgctgggcatccaggtgaa
cctgccagcgtgggcaacctgaacaacatgcgcgccacctacctggaaaccct
gagcgtgtccaccaccaagggctacgccagcgccctggtgccaaggtggtgac
acaggtgggcagcgtgatcgaggaactggacaccagctactgcatcgagagcga
cctggacctgtactgcaccagaatcgtgaccttcccaatgagccccggcatcta
cagctgcctgagcggcaacaccagcgcctgcatgtacagcaagaccgaaggcgc
actgacaacaccctacatggccctgaagggaagcgtgatcgccaactgcaagat
caccacctgcagatgcaccgaccccccaggcatcatcagccagaactacggcga
ggccgtgagcctgatcgatcgccattcctgtaacgtgctgtccctggacggcat
cacactgagactgagcggcgagttcgatgccacctaccagaagaacatcagcat
cctggacagccaggtgatcgtgaccggcaacctggacatcagcaccgagctggg
caacgtgaataacagcatcagcaacgccctggacagactggccgagagcaacag
caagctggaaaaagtgaacgtgcgcctgacatccacttccgctctgatcaccta
catcgtgctgaccgtgatcagcctggtgttcggcgccctgagcctggtgctggc
ctgctacctgatgtacaagcagaaggcccagcagaaaccctgctgtggctggg
caacaaccctggaccagatgagagccaccaccagagcctgatga<u>gcggccgc
ggggatccagacatgataagatacattgatgagtttggacaaaccacaactaga
atgcagtgaaaaaatgctttatttgtgaaatttgtgatgctattgctttattt
gtaaccattataagctgcaataaacaagtaacaacaacaattgcattgatttt
atgtttcaggttcagggggaggtgtggaggttttttcggatcctctagagtcg
a</u>caattatttattaataacatatagccaaagacctctatgaacatttagtt
tcccgtatactcaacggcgcgtgtacacacgcatctctttgcatagcgatgaag
tttgttcggcagcagaaatgcagatatccaacaatctggagaaaacttatcat
cacagtggcagtggaaacataccccctctatattcatgtataattatcgtcta
cagcgtccaggatagtggcgtgagaaatggagatctcagccctcctttccat
ggcatgccgcttattgttcattaaacgacaatggtctcaacgcagatatgg
gcatagattctgaagaacccgttgacaatccgaagaagaaggcgtgcaggtctt
tggaagactcgcacgttggtcttataatgtatgatcgagatgtcaccctaatgc
cacatggtacaggcttatcgcggtcatggcgatcggacttgtaatttgcaacga
tgggcaaaggatcgacgacatgccaaacattctgaaccgtagagatgttaacg
atgacgaggatgaatatcccatgctcgctgccatagtatcaagtacacgcgaa
taaggacgcgtcaacatcgttatatgcacacaatgggctacacgtgactaaca
ccccgaatattagtcatatgtgagtttcagtctggctccatatagcctgtag
actatttgtggtttaagtgtaacgaggcgctgtaacgagactcggccgatt
gtaagaacaagcaaatgcactttccatttaacaagaagtgtagagagaatactc
aacctctttggatgtatcctcgag

Figure 14H

Partial plasmid pSB1 44cds SV FCAopt sequence for vSB1-009 (SEQ ID NO:19) (6791 bp)

pSB1 44 cds SV CaF opt
6791 bp

*Green and Italic = UL44 Recombination Arms*
BLUE AND UPPERCASE = SV40 PROMOTER
Black and Bold = NDV-F-CA02-CSmut sequence

*Ctttgtcatgctcggagctctgatcgcatcttatcattacgtctgcatagcaacgtct
ggagacgtgacgtggaagacggggttttagttgtggcggcagggacgattgccggcat
cacggctcgtatggagacattctcctctagccggctttcttcgcgtatacggcgt
tagctattcacgtggtcagagacgccagtcggtctctaatgaacacgtgctactaccgt
gcacgtcgggaaattactgtgaacggtgcatatcgctcggtcgcgcgcgtctcccgcc
cagcacggacgccgaggcgacgcgcgaagaagacgtatccagttacgatacgctggggg
ggaatattcctacgataattctgagctcatagcggtcatctcgattccagccatagcc
agcttcaaaagtacatgtcgaacgcaactaagcaccagtcaacattgactgacacgtt
acgcagtatatgcggttcttggtggtacaagtgtcgcgatattccttccgtcgcgct
accacgaggttctgttccgtccaatccttgtattactgttaatattcggggcaatggct
actaccttagccggcttcggtttacttctcgggcgacattgttttcgcgacagccgc
ggttctgtgctgctacacttgtataaatgtaccgcaacgcgaatagcggaataaagcaat
tggcggccgccgcagctggtaaatgcatattaggaactgccatctcgagcatgttggtt
tgcgtgttaatacaatattcctgatcgcggagcgattaattttatatcatgtgctcat
agcgttcttcgaactgcgaataaaactttcgtggctactaaaggggctatcgtgggt
ttatgcgctgtcgaaaacatgaaaggccgatttaaagctaagttgcgcaggcagaggc
cactccatatacgctctcggagacgcggctcgcacgccagctgaaatattttccccct*
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTG
GAGGCCTAGGCTTTTGCAAAAAGCTcccggggcggccgccacc**atgggcagcaagccca
gcacctggatcagcgtgacCctgatgctgatcaccagaaccatgctgatcctgagctgc
atctgccccacaagcagcctggacggcagaccctggccgctgccggcatcgtggtgac
cggcgacaaggccgtgaacatctacaccagcagccagaccggcagcatcatcatcaagc
tgctgcccaacatgcccaaggacaaagaggcctgcgccaaggcccccCtggaagcctac
aacagaaccctgaccaccctgctgaccccctgggcgacagcatcagaagaatccaggg**

Figure 14I cagcgccaccacaagcggcggaggaaagcagggcagactggtgggcgctatcatcggga
gcgtggccctgggcgtggccacagctgcccagattaccgctgcagccgcctgattcag
gccaatcagaacgccgccaacatcctgagactgaaagagagcattgccgccaccaacga
cgccgtgcacgaagtgacaaacggactgtcccagctggctgtcgctgtcggcaagatgc
agcagttcgtgaacaaccagttcaacaacaccgccagagagctggactgcatcaagatc
gcccagcaggtgggcgtggagctgaacctgtacctgaccgagctgaccacagtgttcgg
cccccagatcacaagcccgctctgacccagctgacaatccaggccctgtacaacctgg
ctggcggcaacatggactatctgctgactaagctgggagtgggcaacaaccagctgtcc
agcctgatcgggtccgggctgatcacaggcaaccccatcctgtacgacagccagacaca
gctgctgggcatccagatcaacctgccatccgtgggaagcctgaacaacatgagagcca
cctacctggaaaccctgagcgtgtccaccaccaagggcttcgccagcgccctggtgccc
aaggtggtgacacaggtgggcagcgtgatcgaggaactggacaccagctactgcatcga
gagcgacatcgacctgtactgcaccagagtggtgaccttcccaatgagccccggcatct
acagctgcctgagcggcaacaccagcgcctgcatgtacagcaagaccgaaggagcactg
acaacaccctacatggccctgaagggaagcgtgatcgccaactgcaagatgaccacctg
cagatgcgccgaccccccaggcatcatcagccagaactacggcgaggccgtgagcctga
tcgacaaacattcctgtagcgtgctgtccctggatggcatcacactgagactgagcggc
gagttcgacgccacctaccagaagaacatcagcatcctggacagccaggtgatcgtgac
cggcaacctggacatcagcaccgagctgggcaacgtgaacaacagcatcagcagcaccc
tggacaagctggccgagtccaacaacaagctgaacaaagtgaacgtgaacctgaccagc
acaagcgccctgatcacctacatcgtgctggccatcgtgtccctggccttcggcgtgat
cagcctggtgctggcctgctacctgatgtacaagcagagagcccagcagaaaccctgc
tgtggctgggcaataacaccctggaccagatgagggccaccaccagaacctgatgagcg
gccgcgatacctgcagg tttgcggtgacattgatctggctcattatatgcccgagctc
ttgtaacatgcggacgcgattccgtagtaggcacatctcaaatgcaaaagcggcatg
tcaacgtataggtacatcggcctgcttacagtcggtaggcatatccaccggaa
aacttcagctttagactcctcaggtgatgaggaatagtatgtaacctctagcagtacg
gtattctaaaaaaggtagatccttttccacacggcacagactaaataacgtacacta
cacaggttctctcgaacttcgtttggacggaattattccctcggcagcgcctaaaaag
caaacctctagagtagataagtgtcagtgaacctaggccttcttgttcacggctgga
aagctaaggacgaggtacacgcgacccagccacgcacgaacagagtttaacggaagc
gtcgtttcggataaggttgtcggacccgcgggtcgttgaaaagtggctgcgcgcc
taccgacgaatacgtcggtaacaatttagaaatcgatatgactgcgagtaccgtaca
atcgcgaaatacggtctctatatagctactggtccttaaatatgtaagtatgatgtcc
cctactccgaagacgaccgcgacttggtcgcagtacgtgggctgctccggatgatgga
cgagaccacatctgagcgacacaaacgttcgcgttcaggatgcccggttgttatgcg
gttgtacgatcgggatcgtcttactgttcgtcatcacagctacggtcgtgctagct
tcgctgtttgcattctcttacatgtccctggagtccggtacatgtcctcacgaatggat
cggtttaggctatagttgtatgcgcgcgatggggagcaacgctaccgagctagaagccc
tagatacgtgctccgacataacagcaagcttgtcgacttactcatgcgaaattcta
atcgaagctatcgc

Figure 14J

**Partial plasmid pHVT US2 SV-Fopt-SynPA for vHVT306
(SEQ ID NO:20)     (7294bp)**

```
                              syn poly A tail
           NDV-FconsVIId-CSmut
       SV40 promoter
SORF3 flanking Arm                          US2 Flanking Arm
``` pHVT US2 SV-Fopt-synPA
7294 bp

*Green and Italic = SORF3 and US2 Recombination Arms*
BLUE AND UPPERCASE = SV40 PROMOTER
Black and Bold = NDV-FconsVIId-CSmut sequence
<u>*Red and Italic and Underlined = Synthetic Poly A tail*</u>

*taaaatgggatctatcattacattcgttaagagtctggataattttactgttgccagc
ttcgatcttgaacgtactgtggatagtgccttacttggaatcgtgaaatttgaaacg
tccattatttggatatcttccggtcgtcccatatccgcctggtaccgtcggatacc
ttgccgtatggattcgtattgacagtcgcgcaatcggggaccaacaacgcgtgggtcc
acactcattcggaaattttccgatgattctgaatatttattgccgctcgttacgagtcg
ttggacatatctgtaatacatttcttcttctgaaggatcgctgcacatttgatctatac
attggccaggatgttcaagtctcagatgttgcattctggcacagcacaactttatggca
tttccgatgtaatcgtccggcagcctgggggagttctatattcgcatattgggatggt
aaggacaatagcagatctcgcaacctccagggaggctataataacgttttaaaggatg
gatttctcataaaatctgtcgcaaattacactgagaatatccttactagcgcgatt
gagagcatcgtcgtccaattttctaaatggaagaaaacaaggcgggcaagagtgttcc
aaacattctcattttggcgaatctctcaaatccatggcgtgcaattgattgcaaaat
tggcacttccgttcacgtttgtatctccaaactctaagacactttttaattgaaaacta
cgttctagtgtggaaagaaacctataggcagaccatagaactatttgacaccacatatc
ttttgtatgtcaaactgaccatgatcgtatgttgctgaatgcactaggcaattcgct
ccgcgactccatacattgaataattccacacgtcagctcatcggttagcaaggtccag
tagttgaagtcatttattttcccgcggctggcaaatctactctggaatatccaa
gttgtcgaatatgatcgcacggctctggtcatggtgaaggaacttgtagcataagac
gcaggtatcataggggtaatatttttttattcactcacatactaaaagtaacgcatatt
agcaccatgtatgggctatcaattgacattgcgtagcactacatcacgattatgtaca
acataatgggacaacatatgcctgcaggtcgaccc*AATTCGAGCTCGGTACAGCTTGGC
TGTGGAATGTGTGTCAGTTAGGGTGTGGAAAGTCCCCAGGCTCCCCAGCAGGCAGAAGT
ATGCAAAGCATGCATCTCAATTAGTCAGCAACCAGGTGTGGAAAGTCCCCAGGCTCCCC
AGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGC
TGACTAATTTTTTTTATTTATGCAGAGGCCGAGGCCGCCTCGGCCTCTGAGCTATTCCA
GAAGTAGTGAGGAGGCTTTTTTGGAGGCCTAGGCTTTTGCAAAAAGCTcccggggcggc

Figure 14K

```
cgccaccatgggcagcaagcccagcacaagaatcccagcccccctgatgctgatcaccc
gcatcatgctgatcctgggctgcatcagacccacaagctccctggatggacgcccctg
gccgctgccggcatcgtggtgaccggcgacaaggccgtgaacgtgtacaccagcagcca
gaccggcagcatcatcgtgaagctgctgcccaacatgcccagagacaaagaggcctgcg
ccaaggccccctggaagcctacaacagaaccctgaccaccctgctgacccccctgggc
gacagcatcagaaagatccagggctccgtgagcacaagcggcggaggaaagcagggcag
actgatcggcgccgtgatcggcagcgtggccctgggagtggctacagctgcccagatta
ccgctgcagccgccctgatccaggccaaccagaacgccgccaacatcctgagactgaaa
gagagcattgccgccaccaacgaggccgtgcacgaagtgaccgacggcctgagccagct
gtccgtggccgtgggcaagatgcagcagttcgtgaacgaccagttcaacaacaccgcca
gagagctggactgcatcaagatcacccagcaggtgggcgtggagctgaacctgtacctg
accgagctgaccacagtgttcggcccccagatcacaagcccagccctgacacagctgac
catccaggccctgtacaacctggctggcggcaacatggactatctgctgacaaagctgg
gaatcggcaacaaccagctgtccagcctgatcggaagcggcctgatcaccggctacccc
atcctgtacgacagccagacacagctgctgggcatccaggtgaacctgcccagcgtggg
caacctgaacaacatgcgcgccacctacctggaaaccctgagcgtgtccaccaccaagg
gctacgccagcgccctggtgcccaaggtggtgacacaggtgggcagcgtgatcgaggaa
ctggacaccagctactgcatcgagagcgacctggacctgtactgcaccagaatcgtgac
cttcccaatgagccccggcatctacagctgcctgagcggcaacaccagcgcctgcatgt
acagcaagaccgaaggcgcactgacaacacctacatggccctgaagggaagcgtgatc
gccaactgcaagatcaccacctgcagatgcaccgaccccccaggcatcatcagccagaa
ctacggcgaggccgtgagcctgatcgatcgccattcctgtaacgtgctgtccctggacg
gcatcacactgagactgagcggcgagttcgatgccacctaccagaagaacatcagcatc
ctggacagccaggtgatcgtgaccggcaacctggacatcagcaccgagctgggcaacgt
gaataacagcatcagcaacgccctggacagactggccgagagcaacagcaagctggaaa
aagtgaacgtgcgcctgacatccacttccgctctgatcacctacatcgtgctgaccgtg
atcagcctggtgttcggcgccctgagcctggtgctggcctgctacctgatgtacaagca
gaaggcccagcagaaaccctgctgtggctgggcaacaacaccctggaccagatgagag
ccaccaccagagcctgatgacgcggcgcgatatcaataaaatatctttattttcattac
atctgtgtgttggttttttgtgtgaatcgatagtactaacatacgctctccatcaaaac
aaaacgaaacaaaacaaactagcaaaataggctgtccccagtgcaagtgcaggtgccag
aacattctcttctagacctgcaggcccgggcaagtagatgcaattcctcacactagt
tgggttatctactattgaattttccctatctgtatacactggagcctctacaag
catattgcatcatgtacgttttatactgtcttaacgccatggaacggaggcgt
cgtcgtcatgtattggacggcaacataggcagcaacacaaattgcgtttaggtgggtg
catgtggaccgataccaagccctgcagctgggaacgtctggtggagagcgataat
ttgatatacgcacgccatattactgtcgttgaagtacgcttatcttctatgttttcaa
atttaggttccaagtggacgtgagaagtgtttgtatctcacatggaatggccaaggc
atccagccaggtgctggtacttaatggcaaacaaacgttttggtagaggtattga
ttctattgcagttctgcagatatctgcagcccgagtatccacaggctacgatacgt
tatcggaggcctccgattctagcattacatagcggtcagtagatcctgccattcgta
gcgcaaccggtacatcttcaaacagtctcacaataaatgcatctctcgttcctgcaa
tcggaacgggcataccactccgctgccgatttaattctcacaattggcgatgcc
ggcgggcaaaacgaatgtggatttggcaaacgacacaggtctgctgtacggactaat
atgggcacaccacatcattcttcagatgctcatgcattgttctatgagaaagatcca
```

Figure 14L tagggtggaggcagcgtcacgagatcgcccaggcaatcgatcgcattcgtctagtaaag
tgacgagagttatcatgcacacaccat

Figure 14M plasmid pCD046+NDV-F wt for vHVT110 (SEQ ID NO:21) (8249 bp)
*Green and Italic = BamHI fragment I intergenic*
*Recombination Arms*
BLUE AND UPPERCASE = MCMV PROMOTER
Black and Bold = NDV-F VIId wildtype consensus sequence
*Red and Italic and Underlined = SV40 Poly A tail*

```
                           NDV-F VIId wt
                                  |
                                  |    poly A SV 40
                                  |       |
  Intergene 1 arm    pMCMV        |       |    Intergene 1 arm
``` pCD046+NDV-F wt
8249bp

*gagctcagggtatgatactcagctgttattgtggcgaccaggaggactccaatgctta*
*gcattcataagaacgctagagatgctatttaacgatgtgctgtcgtctaaagaattcgt*
*gcattagcctttaaatgtaaaaccaatgacgcattcactacgctcgtgcgtgcaattt*
*ctgggccagggtatgcatattccataacagaaatcgacacttgagaagaggatctgact*
*gtttgggataaaggtcgtttcggtctgtcctagcgataaattcatatgacgatataca*
*ttaaacatctgtgtgcagtacttaggtatttaatcatgtcgatgaaatgttatgtgtaa*
*atatcggacaatatagataacgggcacgctgctattgtaacgtgcgccgcgcgctagt*
*gctgactaatagtgtggatgatgtatacagtatattacaaacggaaatgatacgtaaca*
*aatatgtactcttattgatttataaaacatacatgcagtgttgctatgtcacataat*
*tagcctcgccgtctacgctccactgaagataatgggctccgctgttcaaaaaaatca*
*ggtgcgtcgataagacttggtgcagtctcttcgggtgtgcaatttagatttgccgca*
*tggagggtatctgggattttgccaatgctggagcgacgactgtacgattcgtcccat*
*cgggatctagcagaccaatgatgttgacacacatcggccatgcatgtacggacggtcta*
*ttgcgcgagtttgttattttcgaaggacaagatggaagtgtatatggaacgacaataa*
*tgttagcttgcattccttagggcggaatctacatgatatcttatccaagcgggtacga*
*gccagagagatgtgatggtcataaagggtaaattttttagatctgaaataacgcagttg*
*cccaaacaacgatcgcgattaaaagaaaaatcggatggtcaattaggacatgcatgga*
*ttctgtgcgcataaaccataaccgagcactgttgggcacttcggtaactcaaatgcga*
*agcgttgcacgtctgcgataactacgcctactatgcacattgttactcctgcatcttaa*
*aaatatatcctgtagtaattttcacagcaatgtcataacatcatctcgctaaagaatga*
*cctgggattggagaagtaatgaatatttgcaaccaatgcattgaataaactaacattaa*
*acgaattc*AATAGTGGATCCCCCAACTCCGCCCGTTTTATGACTAGAACCAATAGTTTT
TAATGCCAAATGCACTGAAATCCCTAATTTGCAAAGCCAAACGCCCCTATGTGAGTA
ATACGGGGACTTTTTACCCAATTTCCCACGCGGAAAGCCCCTAATACACTCATATGGC
ATATGAATCAGCACGGTCATGCACTCTAATGGCGGCCCATAGGGACTTTCCACATAGGG
GGCGTTCACCATTTCCCAGCATAGGGGTGGTGACTCAATGGCCTTTACCCAAGTACATT
GGGTCAATGGGAGGTAAGCCAATGGGTTTTTCCCATTACTGGCAAGCACACTGAGTCAA
ATGGGACTTTCCACTGGGTTTTGCCCAAGTACATTGGGTCAATGGGAGGTGAGCCAATG
GGAAAAACCCATTGCTGCCAAGTACACTGACTCAATAGGGACTTTCCAATGGGTTTTTC

Figure 14N

```
CATTGTTGGCAAGCATATAAGGTCAATGTGGGTGAGTCAATAGGGACTTTCCATTGTAT
TCTGCCCAGTACATAAGGTCAATAGGGGGTGAATCAACAGGAAAGTCCCATTGGAGCCA
AGTACACTGCGTCAATAGGGACTTTCCATTGGGTTTTGCCCAGTACATAAGGTCAATAG
GGGATGAGTCAATGGGAAAACCCATTGGAGCCAAGTACACTGACTCAATAGGGACTTT
CCATTGGGTTTTGCCCAGTACATAAGGTCAATAGGGGGTGAGTCAACAGGAAAGTTCCA
TTGGAGCCAAGTACATTGAGTCAATAGGGACTTTCCAATGGGTTTTGCCCAGTACATAA
GGTCAATGGGAGGTAAGCCAATGGGTTTTTCCCATTACTGGCACGTATACTGAGTCATT
AGGGACTTTCCAATGGGTTTTGCCCAGTACATAAGGTCAATAGGGGTGAATCAACAGGA
AAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACGTACATA
AGGTCAATAGGGGTGAGTCATTGGGTTTTTCCAGCCAATTTAATTAAAACGCCATGTAC
TTTCCCACCATTGACGTCAATGGGCTATTGAAACTAATGCAACGTGACCTTTAAACGGT
ACTTTCCCATAGCTGATTAATGGGAAAGTACCGTTCTCGAGCCAATACACGTCAATGGG
AAGTGAAAGGGCAGCCAAAACGTAACACCGCCCGGTTTTCCCCTGGAAATTCCATATT
GGCACGCATTCTATTGGCTGAGCTGCGTTCTACGTGGGTATAAGAGGCGCGACCAGCGT
CGGTACCGTCGCAGTCTTCGGTCTGACCACCGTAGAACGCAGAGCTCCTCGCTGCAGgc
ggccgcatgggctccaaaccttctaccaggatcccagcacctctgatgctgatcacccg
gattatgctgatattgggctgtatccgtccgacaagctctcttgacggcaggcctcttg
cagctgcaggaattgtagtaacaggagataaggcagtcaatgtatacacttcgtctcag
acagggtcaatcatagtcaagttgctcccgaatatgcccagggataaggaggcgtgtgc
aaaagccccattagaggcatataacagaacactgactactttgctcactcctcttggcg
actccatccgcaagatccaagggtctgtgtccacatctggaggaggcaagcaaggccgc
ctgataggtgctgttattggcagtgtagctcttggggttgcaacagcggcacagataac
agcagctgcggccctaatacaagccaaccagaatgccgccaacatcctccggcttaagg
agagcattgctgcaaccaatgaagctgtgcatgaagtcaccgacggattatcacaacta
tcagtggcagttgggaagatgcagcagtttgtcaatgaccagtttaataatacggcgcg
agaattggactgtataaaatcacacaacaggttggtgtagaactcaacctatacctaa
ctgaattgactacagtattcgggccacagatcacctcccctgcattaactcagctgacc
atccaggcactttataatttagctggtggcaatatggattacttattaactaagttagg
tatagggaacaatcaactcagctcgttaattggtagcggcctgatcactggttacccta
tactgtatgactcacagactcaactcttgggcatacaagtgaatttaccctcagtcggg
aacttaaataatatgcgtgccacctatttggagaccttatctgtaagtacaaccaaagg
atatgcctcagcacttgtcccgaaagtagtgacacaagtcggttccgtgatagaagagc
ttgacacctcatactgtatagagtccgatctggatttatattgtactagaatagtgaca
ttccccatgtccccaggtatttattcctgtttgagcggcaacacatcagcttgcatgta
ttcaaagactgaaggcgcactcactacgccgtatatggccctttaaaggctcagttattg
ccaattgtaaaataacaacatgtagatgtacagaccctcctggtatcatatcgcaaaat
tatggagaagctgtatccctgatagatagacattcgtgcaatgtcttatcattagacgg
gataactctaaggctcagtggggaatttgatgcaacttatcaaaagaacatctcaatac
tagattctcaagtcatcgtgacaggcaatcttgatatatcaactgaacttggaaacgtc
aacaattcaatcagcaatgccttggataggttggcagaaagcaacagcaagctagaaaa
agtcaatgtcagactaaccagcacatctgctctcattacctatattgttctaactgtca
tttctctagttttcggtgcacttagtctggtgttagcgtgttacctgatgtacaaacag
aaggcacaacaaaagaccttgctatggcttgggaataataccctcgatcagatgagagc
cactacaagagcatgagcggccgcgggatccagacatgataagatacattgatgagtt
tggacaaaccacaactagaatgcagtgaaaaaatgctttatttgtgaaatttgtgatg
```

Figure 14O ctattgctttatttgtaaccattataagctgcaataaacaagttaacaacaacaattgc
attgattttatgtttcaggttcaggggaggtgtgggaggttttttcggatcctctaga
gtcgacaattattttatttaataacatatagccaaagacctctatgaacatttagttt
ccgtatactcaacggcgcgtgtacacacgcatctctttgcatagcgatgaagtttgtt
cggcagcagaaaatgcagatatccaacaatctgagaaaacttatcatcacagtggcag
tggaaacataccccctctatattcatggtataattatcgtctacagcgtccaggatagt
ggcgtgagaaatggagatctgcagcctcctttcatggcatgccgctttattgttca
ttaaacgacaatggtctcaacgcagatatggcatagattctgaagaaccgttgac
aatccgaagaagaaggcgtgcaggtctttggaagactgcacgttggtcttataatgta
tgatcgagatgtcacctaatgccacatggtacaggcttatcgcggtcatgcgatcgg
acttgtaatttgcaacgatgggcaaaggatcgacgacatgcaaacattctgaaccgt
agagatgttaacgatgacgaggatgaatatcccatgctcgctgccatagtatcaagtac
accgcgaataaggacgcgtccaacatcgttatgacacaatgggctacacgtgacta
acacccccgaatattagtcatatgtgagtttcagtctggctcccatatagctgtagac
tatttgtggtttaagtgtgaacgaggcgctgtaacgagactgggccgattgtaagaa
caagcaaatgcacttccatttaacaagaagtgtagagagaatactcaacctctttgga
tgtatcctcgag Figure 14P
Partial plasmid pHM103+NDV-F wt sequence for vHVT111 (SEQ ID NO:22) (7205bp)

pHM103 + NDV-F wt
7205bp

*Green and Italic = BamHI fragment I intergenic Recombination Arms*
BLUE AND UPPERCASE = SV40 PROMOTER
Black and Bold = NDV-F VIId wildtype consensus sequence
*Red and Italic and Underlined = SV40 Poly A tail*

*gagctcagggtatgatactcagctgttattgtggccgaccaggaggactccaatgctta*
*gcattcataagaacgctagagatgctattaacgatgtgctgtcgtctaaagaatttgt*
*gcatttagcctttaaatgtaaaaccaatgacgcattcactacgctcgtgcgtgcaattt*
*ctgggccagggtatgcatattccataacagaaatcgacacttgagaagaggatctgact*
*gtttggataaaggtcgtttgggtctgtcctagcgatataatttatatgacgatataca*
*ttaaacatctgtgtgcagtacttaggtatttaatcatgtcgatgaaatgttcatgtgtaa*
*atatcggacaatatagataacgggcacgctgctattgtaacgtgcgccgcgcgctagt*
*gctgactaatagtgtggatgatgtatacagtatattacaaacggaaatgatacgtaata*
*aattatgtactcttattgatttataaaaacatacatgcagtgttgctatgtcacataat*
*tagcctcgccgtctacgctccactgaagataatgggctccgctgttcaaaaaaatca*
*gcgtgcgtcgataagacttggtgcagtctcttcggggtcgcaatttagatttgccgca*
*tggagggtatctggggattttttgccaatgctggagcgacgactgtacgattcgtcccat*
*cgggatctagcagaccaatgatgttgacacaatcggccatgcatgtacggacggtcta*
*ttgcgcgagtttgttatttcgaaggacaagatggaagtgtatatggaaccgacaataa*
*tgttagttgcatttcttaggcgaatctacatgatatcttatccaagcgggtatga*
*gccagagagatgtgatggtcataaagggtaaatttttagatctgaaataacgcagttg*
*cccaaacaacgatcgcgattaaaagaaaaatcggatggttcaattaggacatgcatgga*
*ttctgtgcgcataaaccataaccgcagcactgttgggcacttcggtaactcaaatgcga*
*agcgttgcacgtctggataactacgctactatgcacattgttactcctgatcttaa*
*aaatatatcctgtagtaattttcacagcaatgtcataacatcatctcgctaaagaatga*
*cctgggattggagaagtaatgaatatttgcaaccaatgcattgaataaactaacattaa*
acgaattcGAGCTCGGTACAGCTTGGCTGTGGAATGTGTGTCAGTTAGGGTGTGGAAAG
TCCCCAGGCTCCCCAGCAGGCAGAAGTATGCAAAGCATGCATCTCAATTAGTCAGCAAC
CAGGTGTGGAAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTAACTCCGCCC
AGTTCCGCCCATTCTCCGCCCCATGGCTGACTAATTTTTTTATTTATGCAGAGGCCGA
GGCCGCCTCGGCCTCTGAGCTATTCCAGAAGTAGTGAGGAGGCTTTTTTGGAGGCCTAG
GCTTTTGCAAAAAGCTgcggccgcatgggctccaaaccttctaccaggatcccagcacc

Figure 14Q

```
tctgatgctgatcacccggattatgctgatattgggctgtatccgtccgacaagctctc
ttgacggcaggcctcttgcagctgcaggaattgtagtaacaggagataaggcagtcaat
gtatacacttcgtctcagacagggtcaatcatagtcaagttgctcccgaatatgcccag
ggataaggaggcgtgtgcaaaagccccattagaggcatataacagaacactgactactt
tgctcactcctcttggcgactccatccgcaagatccaagggtctgtgtccacatctgga
ggaggcaagcaaggccgcctgataggtgctgttattggcagtgtagctcttggggttgc
aacagcggcacagataacagcagctgcggccctaatacaagccaaccagaatgccgcca
acatcctccggcttaaggagagcattgctgcaaccaatgaagctgtgcatgaagtcacc
gacggattatcacaactatcagtggcagttgggaagatgcagcagtttgtcaatgacca
gtttaataatacggcgcgagaattggactgtataaaaatcacacaacaggttggtgtag
aactcaacctatacctaactgaattgactacagtattcgggccacagatcacctcccct
gcattaactcagctgaccatccaggcactttataatttagctggtggcaatatggatta
cttattaactaagttaggtatagggaacaatcaactcagctcgttaattggtagcggcc
tgatcactggttaccctatactgtatgactcacagactcaactcttgggcatacaagtg
aatttaccctcagtcgggaacttaaataatatgcgtgccacctatttggagaccttatc
tgtaagtacaaccaaaggatatgcctcagcacttgtcccgaaagtagtgacacaagtcg
gttccgtgatagaagagcttgacacctcatactgtatagagtccgatctggatttatat
tgtactagaatagtgacattccccatgtccccaggtatttattcctgtttgagcggcaa
cacatcagcttgcatgtattcaaagactgaaggcgcactcactacgccgtatatggccc
ttaaaggctcagttattgccaattgtaaaataacaacatgtagatgtacagaccctcct
ggtatcatatcgcaaaattatggagaagctgtatccctgatagatagacattcgtgcaa
tgtcttatcattagacgggataactctaaggctcagtggggaatttgatgcaacttatc
aaaagaacatctcaatactagattctcaagtcatcgtgacaggcaatcttgatatatca
actgaacttggaaacgtcaacaattcaatcagcaatgccttggataggttggcagaaag
caacagcaagctagaaaagtcaatgtcagactaaccagcacatctgctctcattcct
atattgttctaactgtcatttctctagttttcggtgcacttagtctggtgttagcgtgt
tacctgatgtacaaacagaaggcacaacaaaagaccttgctatggcttgggaataatac
cctcgatcagatgagagccactacaagagcatgagcggccgcggggatccagacatgat
aagatacattgatgagtttggacaaacoacaactagaatgcagtgaaaaaatgctta
tttgtgaaatttgtgatgctattgctttatttgtaaccattataagctgcaataaacaa
gttaacaacaacaattgcattgatttatgtttcaggtcaggggaggtgtgggaggt
ttttcggatcctctagagtcgacaatatttttattaataacatatagccaaagacc
tctatgaacattagttccgtatactcaacggcgcgtgtacacacgcatctcttgc
atagcgatgaagtttgttcggcagcagaaatgcagatatccaacaatctggagaaaac
ttatcatcacagtggcagtggaaacataccoctctatattcatggtataattatcgtc
tacagcgtcaggatagtggcgtgagaaatggagatctgcagcctctttccatggc
atgcgctttattgttcattaaacgcacaatggtctcaacgcagatatgggcatagat
tctgaagaaccgttgacaatcgaagaagaaggcgtgcaggtctttggaagactcgca
cgttggtcttataatgtatgatcgagatgtcaccctaatgcacatggtacaggcttat
cgcggtcatggcgatcggacttgtaatttgcaacgatgggcaaggatgacgacatgc
caaacattctgaacccgtagagatgttaacgatgacgaggatgaatatccatgctcgc
tgccatagtatcaagtacacgcgaataaggacgcgtccaacatcgttatatgcacaca
atgggctacacgtgactaacacccccgaatattgtcatatgtgagtttcagtctggct
cccatatagcctgtagactattgtgcttaagtgtgaacgagcgctgtgaacgagac
tcgggccgattgtaagaacaagcaaatgcacttccatttaacaagaagtgtagagaga
atactcaactctttggatgtatcctcgag
```

Figure 14R
Partial plasmid pHM103+NDV-F CA02 for vHVT116 (SEQ ID NO:23) (7212bp)

NDV-F-CA02-CSmut
SV40 Promoter       polyA SV 40
Intergene 1 arm                          Intergene 1 arm pHM103 + NDV-F CA02
7212bp

*Green and Italic = BamHI fragment I intergenic Recombination Arms*
BLUE AND UPPERCASE = SV40 PROMOTER
Black and Bold = NDV-F-CA02-CSmut sequence
*Red and Italic and Underlined = SV40 Poly A tail*

*gagctcagggtatgatactcagctgttattgtggcgacaggaggactccaatgctta
gcattcataagaacgctagagatgctatttaacgatgtgctgtcgtctaaagaatttgt
gcatttagcctttaaatgtaaaaccaatgacgcattcactacgctcgtgcgtgcaattt
ctgggcagggtatgcatattccataacagaaatcgacacttgagaagaggatctgact
gtttggataaaggtcgtttggtctgtcctagcgatataatttatatgacgatataca
ttaaacatctgtgtcagtacttaggtatttaatcatgtcgatgaaatgttatgtgtaa
atatcggacaatatagataacgggcacgctgctattgtaacgtgcgcccgcgcgctagt
gctgactaatagtgtggatgatgtatacagtatattacaaacggaaatgatacgtaata
aattatgtactcttattgatttataaaaacatacatgcagtgttgctatgtcacataat
tagcctcgcccgtctacgctccactgaagataatgggctccgctgttcaaaaaatca
gcgtgcgtcgataagactttggtgcagtctcttcggggtcgcaatttagatttgccgca
tggaggtatctgggattttttgccaatgctggagcgacgactgtacgattcgtcccat
cgggatctagcagaccaatgatgttgacacacatcggccatgcatgtacggacggtcta
ttgcgcagtttgttattttcgaaggacaagatggaagtgtatatggaacgacaataa
tgctagtttgcatttcttagggcggaatctacatgatatcttatccaagcggggtatga
gccagagagatgtgatggtcataaagggtaaattttttagatctgaaataacgcagttg
cccaaacaacgatcgcgattaaaagaaaaatcggatggttcaattaggacatgcatgga
ttctgtgcgcataaaccataacgcagcactgttgggcacttcgtaactcaaatgcga
agcgttgcacgtctgcgataactacgcctactatgcacattgttactcctgcatcttaa
aaatatatcctgtagtaattttcacagcaatgtcataacatcatctcgctaaagaatga
cctgggattggagaagtaatgaatatttgcaaccaatgcattgaataaactaacattaa
acgaattcGAGCTCGGTACAGCTTGGCTGTGGAATGTGTGTCAGTTAGGGTGTGGAAAG
TCCCCAGGCTCCCCAGCAGGCAGAAGTATGCAAAGCATGCATCTCAATTAGTCAGCAAC
CAGGTGTGGAAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTAACTCCGCCC
AGTTCCGCCCATTCTCCGCCCCATGGCTGACTAATTTTTTTATTTATGCAGAGGCCGA
GGCCGCCTCGGCCTCTGAGCTATTCCAGAAGTAGTGAGGAGGCTTTTTTGGAGGCCTAG
GCTTTTGCAAAAAGCT*gcggccgccaccatgggcagcaagcccagcacctggatcagcg

Figure 14S tgaccctgatgctgatcaccagaaccatgctgatcctgagctgcatctgccccacaagc
agcctggacggcagacccctggccgctgccggcatcgtggtgaccggcgacaaggccgt
gaacatctacaccagcagccagaccggcagcatcatcatcaagctgctgcccaacatgc
ccaaggacaaagaggcctgcgccaaggccccctggaagcctacaacagaaccctgacc
accctgctgaccccctgggcgacagcatcagaagaatccagggcagcgccaccacaag
cggcggaggaaagcagggcagactggtgggcgctatcatcgggagcgtggccctgggcg
tggccacagctgcccagattaccgctgcagccgccctgattcaggccaatcagaacgcc
gccaacatcctgagactgaaagagagcattgccgccaccaacgacgccgtgcacgaagt
gacaaacggactgtcccagctggctgtcgctgtcggcaagatgcagcagttcgtgaaca
accagttcaacaacaccgccagagagctggactgcatcaagatcgcccagcaggtgggc
gtggagctgaacctgtacctgaccgagctgaccacagtgttcggcccccagatcacaag
ccccgctctgacccagctgacaatccaggccctgtacaacctggctggcggcaacatgg
actatctgctgactaagctgggagtgggcaacaaccagctgtccagcctgatcgggtcc
gggctgatcacaggcaaccccatcctgtacgacagccagacacagctgctgggcatcca
gatcaacctgccatccgtgggaagcctgaacaacatgagagccacctacctggaaaccc
tgagcgtgtccaccaccaagggcttcgccagcgccctggtgcccaaggtggtgacacag
gtgggcagcgtgatcgaggaactggacaccagctactgcatcgagagcgacatcgacct
gtactgcaccagagtggtgaccttcccaatgagccccggcatctacagctgcctgagcg
gcaacaccagcgcctgcatgtacagcaagaccgaaggagcactgacaacaccctacatg
gccctgaagggaagcgtgatcgccaactgcaagatgaccacctgcagatgcgccgaccc
cccaggcatcatcagccagaactacggcgaggccgtgagcctgatcgacaaacattcct
gtagcgtgctgtccctggatggcatcacactgagactgagcggcgagttcgacgccacc
taccagaagaacatcagcatcctggacagccaggtgatcgtgaccggcaacctggacat
cagcaccgagctgggcaacgtgaacaacagcatcagcagcaccctggacaagctggccg
agtccaacaacaagctgaacaaagtgaacgtgaacctgaccagcacaagcgccctgatc
acctacatcgtgctggccatcgtgtccctggccttcggcgtgatcagcctggtgctggc
ctgctacctgatgtacaagcagagagcccagcagaaaaccctgctgtggctgggcaata
acacccctggaccagatgagggccaccaccagaacctgatga*gcggccgcggggatccag*
*acatgataagatacattgatgagtttggacaaaccacaactagaatgcagtgaaaaaaa*
*tgctttatttgtgaaatttgtgatgctattgctttattgtaaccattataagctgcaa*
*taaacaagttaacaacaacaattgcattgattttatgtttcaggttcaggggaggtgt*
*gggaggttttttcggatcctctaga*gtcgacaattatctatttaataacatatagcc
aaagaccctctatgaacatttagtttcccgtatactcaacggcgcgtgtacacacgcatc
tctttgcatagcgatgaagtttgttcggcagcagaaatgagatatccaacaatctgg
agaaaactatcatcacagtggcagtggaaacatacccctctatattcatgtataat
tatcgtctacagcgtccaggatagtggcgtgagaaatggagatctgcagcctcttt
ccatggcatgcgctttattgttcattaaacgcacaatggtctcaacgcagatatggg
catagattctgaagaaccgttgacaatcgaagaagaaggcgtgcaggtctttggaag
actcgcacgttggtcttataatgtatgatcgagatgtcacctaatgcacatggtaca
ggcttatcgcggtcatggcgatcggacttgtaatttgcaacgatggcaaggatcgac
gacatgccaaacattctgaaccgtagagatgttaacgatgacgaggatgaatatcca
tgctcgctgccatagtcaagtacaccgcgaataaggacgcgtccaacatcgtatat
gcacacaatggctacacgtgactaacaccccgaatattagtcatatgtgagtttcag
tctggctccatatagcctgtagactatttgtggttaagtgtgaacgaggcgctgtga
acgagactcggccgattgtaagaacaagcaaatgcactttccattaacaagaagtgt
agagagaatactcaactctttggatgtatcctcgag*

Figure 14T

Partial plasmid HVTIG2 SV Fwt SbfI sequence for vHVT301 (SEQ ID NO:24) (6641bp)

HVT IG2 SV Fwt SbfI 6641 bp

*Green and Italic = gp070 and gp066 Recombination Arms*
BLUE AND UPPERCASE = SV40 PROMOTER
Black and Bold = NDV-F VIId wildtype consensus sequence
Red and Underlined = SV40 Poly A tail

*tgtttcgcaccatatccaagctggctgtccctaagagcttattcctgcaagacctcata*
*cggaataattgcccgaccaatacttattacggacataggtaggccgataaatattatgt*
*tgactggaggatggaaaggaggttttgtaacagctacatcgctcgttcatcagcaagcg*
*atactttggatatccgagcttcaaaagccgcataaaccccgctttatttctgaatacgc*
*cccaacagtaacacatgcgtggttcctggcacttggaacgccgtgttttataggcaaga*
*acatactacccaaagaggtcttgggatttctggcgcgtcgttgcaatgaagaaatgaat*
*tctttgttccttgaaatgccgacaactctaaaacggtattcgagcaccattactttac*
*gcgtggatctgaagtaaatccagcgttgttgatggagcctaacagattttgcaactga*
*tggattcgcggaaaatcctatgtttatacgaatccgctatgtgcgacaaccccggagct*
*cagggtatgatactcagctgttattgtggccgaccaggaggactccaatgcttagcatt*
*cataagaacgctagagatgctatttaacgatgtgctgtcgtctaaagaatttgtgcatt*
*tagcctttaaatgtaaaaccaatgacgcattcactacgctcgtgcgtgcaatttctggg*
*ccagggtatgcatattccataacagaaatcgacacttgagaagaggatctgactgtttg*
*ggataaaggtcgtttgggtctgtcctagcgatataatttatatgacgatatacattaaa*
*catctgtgtgcagtacttaggtatttaatcatgtcgatgaaatgttatgtgtaaatatc*
*ggacaatatagataacgggcacgctgctattgtaacgtgcgcccgcgcgctagtgctga*
*ctaatagtgtggatgatgtatacagtatattacaaacggaaatgatacgtaataaa*cct
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTTG
GAGGCCTAGGCTTTTGCAAAAAGCTgcggccgcatgggctccaaaccttctaccaggat
cccagcacctctgatgctgatcacccggattatgctgatattgggctgtatccgtccga
caagctctcttgacggcaggcctcttgcagctgcaggaattgtagtaacaggagataag
gcagtcaatgtatacacttcgtctcagacagggtcaatcatagtcaagttgctcccgaa

Figure 14U tatgcccagggataaggaggcgtgtgcaaaagccccattagaggcatataacagaacac
tgactactttgctcactcctcttggcgactccatccgcaagatccaagggtctgtgtcc
acatctggaggaggcaagcaaggccgcctgataggtgctgttattggcagtgtagctct
tggggttgcaacagcggcacagataacagcagctgcggccctaatacaagccaaccaga
atgccgccaacatcctccggcttaaggagagcattgctgcaaccaatgaagctgtgcat
gaagtcaccgacggattatcaactatcagtggcagttgggaagatgcagcagtttgt
caatgaccagtttaataatacggcgcgagaattggactgtataaaaatcacacaacagg
ttggtgtagaactcaacctatacctaactgaattgactacagtattcgggccacagatc
acctcccctgcattaactcagctgaccatccaggcactttataatttagctggtggcaa
tatggattacttattaactaagttaggtatagggaacaatcaactcagctcgttaattg
gtagcggcctgatcactggttaccctatactgtatgactcacagactcaactcttgggc
atacaagtgaatttaccctcagtcgggaacttaaataatatgcgtgccacctatttgga
gaccttatctgtaagtacaaccaaaggatatgcctcagcacttgtcccgaaagtagtga
cacaagtcggttccgtgatagaagagcttgacacctcatactgtatagagtccgatctg
gatttatattgtactagaatagtgacattccccatgtcccaggtatttattcctgttt
gagcggcaacacatcagcttgcatgtattcaaagactgaaggcgcactcactacgccgt
atatggcccttaaaggctcagttattgccaattgtaaaataacaacatgtagatgtaca
gaccctcctggtatcatatcgcaaaattatggagaagctgtatccctgatagatagaca
ttcgtgcaatgtcttatcattagacgggataactctaaggctcagtggggaatttgatg
caacttatcaaaagaacatctcaatactagattctcaagtcatcgtgacaggcaatctt
gatatcaactgaacttggaaacgtcaacaattcaatcagcaatgccttggataggtt
ggcagaaagcaacagcaagctagaaaagtcaatgtcagactaaccagcacatctgctc
tcattacctatattgttctaactgtcatttctctagttttcggtgcacttagtctggtg
ttagcgtgttacctgatgtacaaacagaaggcacaacaaaagaccttgctatggcttgg
gaataatacctcgatcagatgagagccactacaagagcatgagcggccgcggggatcc
agacatgataagatacattgatgagtttggacaaaccacaactagaatgcagtgaaaaa
aatgctttatttgtgaaatttgtgatgctattgctttatttgtaaccattataagctgc
aataaacaagttaacaacaacaattgcattgatttatgtttcaggttcaggggaggt
gtgggaggttttttcggatcctctagaggggattaatcctgcaggtatgtactcttat
tgatttataaaaacatacatgcagtgttgctatgtcacataattagctcgccgtcta
cgctccactgaagataatgggctcccgctgttcaaaaaatcagcgtgcgtcgataaga
cttggtgcagtctcttcggggtcgcaatttagatttgccgcatggaggtatctggg
attttgcaatgctggacgacgactgtacgattcgtccatcgggatctagcagacc
aatgatgtgacacacatcggcatgcatgtacggacggtctattgcgcgagttgtta
ttttcgaaggacaagatggaagtgtatatggaacgacaataatgttagtttgcatttc
ttaggcggaatctacatgatatcttatcaagcgggtatgagccagagagatgtgat
ggtcataaagggtaaattttagatctgaaataagcagttgccaaacaacgatcgc
gattaaagaaaatcggatggttcaattaggacatgcatggattcgtgcgcataaac
cataaccgcagcactgttgggcacttcggtaactcaaatgcgaagcgttgcacgtctgc
gataactacgctactatgcacattgttactcctgcatcttaaaaatatcctgtagt
aatttcacagcaatgtcataacatcatctcgcta

Figure 14V

Partial plasmid pHVTUS10 cds F opt plasmid for vHVT302 (SEQ ID NO:25) (6348bp)

pHVTUS10 cds F opt
6348 bp
Green and Italic = US10 cds Recombination Arms
Black and Bold = NDV-FconsVIId-CSmut sequence

*tccttacggcggatcgaaacgacattaggcatactcggtaccatttgcattcgat
cagcacggatgaaattaggcaggaatgcggtttatattatgcggcattggacaaacgat
atggcattgattggcagtttatgaatgtcttcatgttggcgtaaacggattcctactg
gttcagaagacaacgacgatatattagagagaaaaagctacccagcataggataaaca
cacattgagcattgagagacataggtatcggtatggatggaaaactacacacgtgaac
accaaacgacttatatactcgagcggtgatactactgagcaagaatgcactgcatctga
gccactgaatgaagactgtgatgaaaatgtgaccatcgatggaattggagaagaatatg
cgcagttcttcatgtcccgcaatggtcccaaatctacatcgcttgagcgaggatacc
aaaaaggtatacgatgtatggttttcaacagactcaattatttccctattatgaggc
gttcaggcggtcttgtttgatatgtatatgctaggtcggttggggcgtcgacttaagc
gatctgactgggagactattatgcatctgtcaccaacgcaaagtcggcgtctacataga
actttaagatttgtggagcgtagaattatccatctaacagttatatacgcacatcggg
ccacgttcgccttcgaggcacttcgacagatacgaattttaaagatggatgaataat
taaattggaaagagtaactacattaatcgagcgtcatgacggcgtccgtgaaaatggg
aatttctactcgaaacaccgtgacatttgacagacctggaattgttattctgatatat
agtgggtgtgtctggcggcaacatacataatgtgcatgcgaaaccactttttcagtgt
acgctgacattgtcaacacggagggtagcatctacatacaatatatgttgattacct*
gcagggcggccgccacc**atgggcagcaagcccagcacaagaatcccagccccctgatg
ctgatcacccgcatcatgctgatcctgggctgcatcagacccacaagctccctggatgg
acgcccctggccgctgccggcatcgtggtgaccggcgacaaggccgtgaacgtgtaca
ccagcagccagaccggcagcatcatcgtgaagctgctgcccaacatgcccagagacaaa
gaggcctgcgccaaggccccctggaagcctacaacagaaccctgaccaccctgctgac
cccctgggcgacagcatcagaaagatccagggctccgtgagcacaagcggcggaggaa
agcagggcagactgatcggcgccgtgatcggcagcgtggccctgggagtggctacagct
gcccagattaccgctgcagccgccctgatccaggccaaccagaacgccgccaacatcct
gagactgaaagagagcattgccgccaccaacgaggccgtgcacgaagtgaccgacggcc
tgagccagctgtccgtggccgtgggcaagatgcagcagttcgtgaacgaccagttcaac
aacaccgccagagagctggactgcatcaagatcacccagcaggtgggcgtggagctgaa
cctgtacctgaccgagctgaccacagtgttcggcccccagatcacaagcccagccctga**

Figure 14W cacagctgaccatccaggccctgtacaacctggctggcggcaacatggactatctgctg
acaaagctgggaatcggcaacaaccagctgtccagcctgatcggaagcggcctgatcac
cggctaccccatcctgtacgacagccagacacagctgctgggcatccaggtgaacctgc
ccagcgtgggcaacctgaacaacatgcgcgccacctacctggaaaccctgagcgtgtcc
accaccaagggctacgccagcgccctggtgcccaaggtggtgacacaggtgggcagcgt
gatcgaggaactggacaccagctactgcatcgagagcgacctggacctgtactgcacca
gaatcgtgaccttcccaatgagccccggcatctacagctgcctgagcggcaacaccagc
gcctgcatgtacagcaagaccgaaggcgcactgacaacaccctacatggccctgaaggg
aagcgtgatcgccaactgcaagatcaccacctgcagatgcaccgaccccccaggcatca
tcagccagaactacggcgaggccgtgagcctgatcgatcgccattcctgtaacgtgctg
tccctggacggcatcacactgagactgagcggcgagttcgatgccacctaccagaagaa
catcagcatcctggacagccaggtgatcgtgaccggcaacctggacatcagcaccgagc
tgggcaacgtgaataacagcatcagcaacgccctggacagactggccgagagcaacagc
aagctggaaaaagtgaacgtgcgcctgacatccacttccgctctgatcacctacatcgt
gctgaccgtgatcagcctggtgttcggcgccctgagcctggtgctggcctgctacctga
tgtacaagcagaaggcccagcagaaaaccctgctgtggctgggcaacaacaccctggac
cagatgagagccaccaccagagcctgatga gcggccgccccgggcctgcaggcataggc
acgctctgatgttacagacacaataccgcatacattattgtaaggttgttaataag
gtttattctatgtaagactacaatacttcgacattgcttgtatacatattaaatactt
tctcaagttcctattacataaatggatctatcattacattcgttaagagtctggata
atttactgtttgccagcttcgatcttggaacgtactgtggatagtgcttacttggaa
tcgtgaaaattcgaaacgtccattatttggatatcttccgttgtccatatccgcct
ggtaccgctcggatacctgccgtatggattcgtattgacagtcgcgcaatcggggga
ccaacaacgcgtggtcacactcattcggaaatttccgatgattctgaatattatt
gccgctcgttacgagtcgttggacatatctgtaatacattcttcttctgaaggatcgc
tgcacatttgatctatacattggccaggatgttcaagtctcagatgttgcattctgca
cagcacaactttatggcatttccgatgtaatcgtccggcagccctggggagttctata
ttcgcatattgggatgtaaggacaatagcagatctcgcaacctccagggaggctataa
taacgttttaaggatggattctcataaaatctgtcgcaaattacactgagaatat
ccttactagcgcgattgagagcatcgtcgtccaatttctaaatggaagaaaacaa
ggcgggcaagagtgttccaaacatttcatttcggcgaatctctcaaatccatggcg
tgcaattgattgcaaaattggcattccgttcacgtttgtatctccaaactctaagaca
cttttaattgaaaactacgttctagtgtggaaagaaactataggcagacatagaac
tatttgacccacatatcttttgtatgtcaaactgaccatgatcgtat

Figure 14X

Partial plasmid pHVT US20 cds F CA02 opt sequence
for vHVT303   (SEQ ID NO:26)    (6348bp)

pHVT US10 cds F CA02 opt
6348 bp

Green and Italic = US10 cds Recombination Arms
Black and Bold = NDV-F-CA02-CSmut sequence

*tccctaoggcggatcgaaacgacattaggcatactcgggtaccatttgcattcgat*
*cagcacggatgaattaggcaggaatgcggtttatattatgcggcattggacaaacgat*
*atggcattgattggcagtttatgaatgtcttcatgttgggcgtaaacgattcctattg*
*gttcagaagacaacgacgatatatttagagagaaaagctaccagcataggataaaca*
*cacattgagcattgagagacataggtatcggtatggatgggaaaactacacacgtgaac*
*accaaacgactatatactcgagcggtgatactactgagcaagaatgcactgcatctga*
*gcactgaatgaagactgtgatgaaatgtgaccatcgatggaattggagaagaatatg*
*cgcagttcttcatgtcccgcaatgggtcccaaatctacatcgcttgagcgaggatacг*
*aaaaggtatacgatgtatggtttcaacagactcaattatttccctattatgaggc*
*gttcaggcggtctttgtttgatatgtatatgctaggtcggttgggcgtcgacttaagc*
*gatctgactgggagactattatgcatctgtcaccaacgcaaagtcggcgtctacataga*
*acttaagatttgtggagcgtagaattatcccatctaacagttatatacgcacatcggg*
*ccacgttccgcttcgaggcacttcgacagatacgaatttaagatggatgaataat*
*taaattggaaagagtaactacattaatcgagcgtcatgacggcgtccgtgaaaatggg*
*aatttctactcgaaacaccgtgacatttgacagacctggaattgttattctgatatat*
*agtgggtgtgtctggcggcaacatacataatgtcatgcgaaaccacttttcagtgt*
*acgctgacattgtgcaacacggagggtagcatctacatacaatatgttgattacct*
gcagggcggccgccaccatgggcagcaagcccagcacctggatcagcgtgaccctgatg
ctgatcaccagaaccatgctgatcctgagctgcatctgccccacaagcagcctggacgg
cagacccctggccgctgccggcatcgtggtgaccggcgacaaggccgtgaacatctaca
ccagcagccagaccggcagcatcatcatcaagctgctgcccaacatgcccaaggacaaa
gaggcctgcgccaaggcccctggaagcctacaacagaaccctgaccaccctgctgac
ccccctgggcgacagcatcagaagaatccagggcagcgccaccacaagcggcggaggaa
agcagggcagactggtgggcgctatcatcgggagcgtggccctgggcgtggccacagct
gcccagattaccgctgcagccgccctgattcaggccaatcagaacgccgccaacatcct
gagactgaaagagagcattgccgccaccaacgacgccgtgcacgaagtgacaaacggac
tgtcccagctggctgtcgctgtcggcaagatgcagcagttcgtgaacaaccagttcaac
aacaccgcagagagctggactgcatcaagatcgcccagcaggtgggcgtggagctgaa
cctgtacctgaccgagctgaccacagtgttcggccccagatcacaagccccgctctga
cccagctgacaatccaggccctgtacaacctggctggcggcaacatggactatctgctg

Figure 14Y actaagctgggagtgggcaacaaccagctgtccagcctgatcgggtccgggctgatcac
aggcaaccccatcctgtacgacagccagacacagctgctgggcatccagatcaacctgc
catccgtgggaagcctgaacaacatgagagccacctacctggaaaccctgagcgtgtcc
accaccaagggcttcgccagcgccctggtgcccaaggtggtgacacaggtgggcagcgt
gatcgaggaactggacaccagctactgcatcgagagcgacatcgacctgtactgcacca
gagtggtgaccttcccaatgagccccggcatctacagctgcctgagcggcaacaccagc
gcctgcatgtacagcaagaccgaaggagcactgacaacaccctacatggccctgaaggg
aagcgtgatcgccaactgcaagatgaccacctgcagatgcgccgaccccccaggcatca
tcagccagaactacggcgaggccgtgagcctgatcgacaaacattcctgtagcgtgctg
tccctggatggcatcacactgagactgagcggcgagttcgacgccacctaccagaagaa
catcagcatcctggacagccaggtgatcgtgaccggcaacctggacatcagcaccgagc
tgggcaacgtgaacaacagcatcagcagcaccctggacaagctggccgagtccaacaac
aagctgaacaaagtgaacgtgaacctgaccagcacaagcgccctgatcacctacatcgt
gctggccatcgtgtccctggccttcggcgtgatcagcctggtgctggcctgctacctga
tgtacaagcagagagcccagcagaaaaccctgctgtggctgggcaataacaccctggac
cagatgagggccaccaccagaacctgatgagcggccgcccgggcctgcaggcataggc
acgtctgatgttacagaccacaataccgatacatttattgtaaggttgttaataaag
gtttattctatgtaagactacaatactttcgacattgcttgtacatattaaatactt
tctcaagttcctattacataaaatggatctatcattacattcgttaagagtctggata
attttactgtttgccagcttcgatcttgaacgtactgtggatagtgcttacttgaa
tcgtgaaaattgaaacgtccattatttggatatcttccgttgtccatatccgcc
tggtaccgctggataccttgccgtatggattcgtattgacagtcgcgcaatcggga
ccaacaacgcgtgggtccacactcattcggaaattttccgatgattctgaatatttatt
gcgctcgttacgagtcgttggacatatctgtaatacattcttcttctgaaggatcgc
tgcacatttgatctatacattggcaggatgttcaagtctcagatgttgcattctgca
cagcacaactttatggcattccgatgtaatcgtccggcagccctggggagttctata
ttcgcatattggatggtaaggacaatagcagatctcgcaacctcaggaggctataa
taacgttttaaaggatggattttctcataaaaatctgtcgcaaattacactgagaatat
cctttactagcgccgattgagagcatcgtcgtccatttctaaatggaaagaaacaa
ggcggcaagagtgttccaaacatttcattttcggcgaatctctcaaatccatggcg
tgcaattgattgcaaaattggcattccgttcacgttgtatctccaaactctaagaca
ctttaattgaaaaactacgttctagtgtggaagaaactataggcagaccatagaac
tatttgacaccacatatcttttgtatgtcaaactgaccatgatcgtat

Figure 14Z

Partial plasmid HVT IG2 SVFopt syn tail sequence for vHVT304 (SEQ ID NO:27) (6598bp)

```
        NDV-F VIId-CSmut
SV40 Promoter              Syn Poly a tail
  gp070                      gp066
```

HVT IG2 SVFopt syn tail.
6598 bp

*Green and italic = gp070 and gp066 Recombination Arms*
BLUE AND UPPERCASE = SV40 PROMOTER
Black and Bold = NDV-FconsVIId-CSmut sequence
Red and Underlined = Synthetic Poly A tail

*Tgtttcgcaccatatccagctggctgtccctaagagcttattcctgcaagacctcata*
*cggaataattgccgaccaatacttattacggacataggtaggccgataaatattatgt*
*tgactggaggatggaaaggaggttttgtaacagctacatcgtcgttcatcagcagcg*
*atactttggatatccgagcttcaaaagccgcataaacccgctttatttctgaatacgc*
*cccaacagtaacacatgcgtggttcctgtcacttggaacgccgtgttttataggcaaga*
*acatactaccaaagaggtcttgggattctggcgcgtcgttgcaatgaagaaatgaat*
*tcttttgttccttgaaatgccgacaactctaaaaacggtattcgagcaccattacttac*
*gcgtggatctgaagtaaatccagcgttgttgatggagcctaacagattttgcaactga*
*tggattcgcggaaaatcctatgtttatacgaatccgctatgtgcgacaaccccggagct*
*cagggtatgatactccagctgttattgtggcgaccaggaggactccaatgcttagcatt*
*cataagaacgctagagatgctatttaacgatgtgctgtcgtctaaagaatttgtgcatt*
*tagccttaaatgtaaaaccaatgacgcattcactacgctcgtgcgtgcaattttctggg*
*ccagggtatgcatattccataacagaaatcgacacttgagaagaggatctgactgtttg*
*ggataaaggtcgtttgggtctgtcctagcgataatttatcgacgatatacattaaa*
*catctgcgtgcagtacttaggtatttaatcatgtcgatgaaatgttatgtgtaaatatc*
*ggacaatatagataacgggcacgctgctattgtaacgtgcgccgcgcgctagtgctga*
*ctaacagtgtggatgatgtatacagtatattacaaacggaaatgatacgtaataaacct*
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCATGGCTGACTAATTTTTTTTATTTATGC
AGAGGCCGAGGCCGCCTCGGCCTCTGAGCTATTCCAGAAGTAGTGAGGAGGCTTTTTG
GAGGCCTAGGCTTTTGCAAAAAGCTcccggggcggccgccaccatgggcagcaagccca
gcacaagaatcccagccccctgatgctgatcacccgcatcatgctgatcctgggctgc
atcagacccacaagctccctggatggacgcccctggccgctgccggcatcgtggtgac

Figure 14AA cggcgacaaggccgtgaacgtgtacaccagcagccagaccggcagcatcatcgtgaagc
tgctgcccaacatgcccagagacaaagaggcctgcgccaaggccccctggaagcctac
aacagaaccctgaccaccctgctgaccccctgggcgacagcatcagaaagatccaggg
ctccgtgagcacaagcggcggaggaaagcagggcagactgatcggcgccgtgatcggca
gcgtggccctgggagtggctacagctgcccagattaccgctgcagccgcctgatccag
gccaaccagaacgccgccaacatcctgagactgaaagagagcattgccgccaccaacga
ggccgtgcacgaagtgaccgacggcctgagccagctgtccgtggccgtgggcaagatgc
agcagttcgtgaacgaccagttcaacaacaccgccagagagctggactgcatcaagatc
acccagcaggtgggcgtggagctgaacctgtacctgaccgagctgaccacagtgttcgg
cccccagatcacaagcccagccctgacacagctgaccatccaggccctgtacaacctgg
ctggcggcaacatggactatctgctgacaaagctgggaatcggcaacaaccagctgtcc
agcctgatcggaagcggcctgatcaccggctacccatcctgtacgacagccagacaca
gctgctgggcatccaggtgaacctgcccagcgtgggcaacctgaacaacatgcgcgcca
cctacctggaaaccctgagcgtgtccaccaccaagggctacgccagcgccctggtgccc
aaggtggtgacacaggtgggcagcgtgatcgaggaactggacaccagctactgcatcga
gagcgacctggacctgtactgcaccagaatcgtgaccttcccaatgagccccggcatct
acagctgcctgagcggcaacaccagcgcctgcatgtacagcaagaccgaaggcgcactg
acaacacctacatggccctgaagggaagcgtgatcgccaactgcaagatcaccacctg
cagatgcaccgaccccaggcatcatcagccagaactacggcgaggccgtgagcctga
tcgatcgccattcctgtaacgtgctgtccctggacggcatcacactgagactgagcggc
gagttcgatgccacctaccagaagaacatcagcatcctggacagccaggtgatcgtgac
cggcaacctggacatcagcaccgagctgggcaacgtgaataacagcatcagcaacgccc
tggacagactggccgagagcaacagcaagctggaaaaagtgaacgtgcgcctgacatcc
acttccgctctgatcacctacatcgtgctgaccgtgatcagcctggtgttcggcgccct
gagcctggtgctggcctgctacctgatgtacaagcagaaggcccagcagaaaaccctgc
tgtggctgggcaacaacaccctggaccagatgagagccaccaccagagcctgatga<u>gcg</u>
<u>gccgcgatatcaataaaatatctttatttcattacatctgtgtgttggttttttgtgt</u>
<u>gaatcgatagtactaacatacgctctccatcaaacaaaacgaaacaaaacaaactagc</u>
<u>aaaataggctgtccccagtgcaagtgcaggtgccagaacatttctcttctagacctgca</u>
gg*ttatgtactcttattgatttataaaacatacatgcagtgttgctatgtcacataat*
*tagcctgcccgtctacgctccactgaagataatgggctccgctgttcaaaaaatca*
*gcgtgcgtcgataagacttggtgcagtctcttcggggtcgcaatttagatttgcgca*
*tggagggtatctggggatttttgccaatgctggagcgacgactgtacgattcgtccat*
*cggatctagcagaccaatgatgttgacacatcggccatgcatgtacggacggtcta*
*ttgcgcgagtttgttattttcgaaggacaagatggaagtgtatatggaacgacaataa*
*tgttagtttgcatttcttaggcggaatctacatgatatcttatccaagcgggtatga*
*gcagagagatgtgatggtcataagggtaaattttttagatctgaaataacgcagttg*
*cccaaacaacgatcgcgattaaaagaaaatcggatggttcaattaggacatgcatgga*
*ttctgtgcgcataaacataacgcagcactgttgggcacttcgtaactcaaatgcga*
*agcgttgcacgtctgcgataactacgctactatgcacattgttactcctgcatcttaa*
*aaatatatcctgtagtaatttcacagcaatgtcataacatcatctcgctaa*

Figure 14BB

Partial plasmid pHVT US2 SV-FCA02 opt-synPA for vHVT307 (SEQ ID NO:28) (7294bp)

pHVT US2 SV-FCAO2opt-synPA
7294 bp

*Green and Italic = US2 and SORF3 Recombination Arms*
BLUE AND UPPERCASE = SV40 PROMOTER
Black and Bold = NDV-F-CA02-CSmut sequence
Red and underlined = Synthetic Poly A tail

*tatctccacatcgtattcaggccacggaagtcttcgttatcgaagctattgttactag
tatctggcgacatcgacggttctgcaacgtcgtaccgctttcgatatttccacagaca
atacccatattcgaggcacttactttcgaagactcaacatctacttccatcgccgccac
gtatgtaatttcgggacgttggatgatataaaatatatagtacgcgtccgggtatacac
ctgtgcgaaagtagtacgagaccggcagtcaaaagacgttccgatcttccacagctc
cagttattcggaaggcgtgggcatgggtgtgtgcatgataactctcgtcactttactag
acgaatgcgatcgattgcctggggcgatctcgtgacgctgcctcaccctatggatcttt
ctcatagaacaatgcatggagcatctgaagaatgatgtgggtgtgcccatattagtccg
tacagcagacctgtgtcggtttgccaaatccacattcgttttgcccggcggcatcgcc
caattgtgagaattaaatcggcaggcgggagtggtatgcccggttccggattggcagga
acgagagatgcatttattgtgagactgtttgaagatgtagcggttgcgctaccgaatg
gcaggatctactgaccggctatgtaatgctagaatcggaggcctccgataacgtatcgt
atagcctgtggatactcggggctgcagatatctgcagaactgcaatagaatcaatacct
ctaccaaaacgtttgtttgccattaaagtaccaggcacctgggctggaatgccttgggc
cattccatgtgagatacaaacacttctcacgtccacttggaacctaaattctgaaaaca
tagaagataaggcgtacttcaacgacagtaatatggcgtgcgtatatcaaattatcggc
tctccaccagacgttcccagctgcaggggcttggtatcgagtccacatgcacccacc
taaacgcaattgtgttgctgcctatgttgccgtccaatacatgacgacgacgctccg
ttccatgggcgttaagacagtagataaaaacgtacatgatggcaatatgcttgtagag
gctccaagtgtatcacagataggggaaaattcaatagtagataaacccaactagtgtg
aggaaattgcatctactt*gccccgggcctgcaggtcgaccCAATTCGAGCTCGGTACA
GCTTGGCTGTGGAATGTGTGTCAGTTAGGGTGTGGAAAGTCCCCAGGCTCCCCAGCAGG
CAGAAGTATGCAAAGCATGCATCTCAATTAGTCAGCAACCAGGTGTGGAAAGTCCCCAG
GCTCCCCAGCAGGCAGAAGTATGCAAAGCATGCATCTCAATTAGTCAGCAACCATAGTC
CGCCCCTAACTCCGCCCATCCCGCCCCTAACTCCGCCCAGTTCCGCCCATTCTCCGCC
CCATGGCTGACTAATTTTTTTTATTTATGCAGAGGCCGAGGCCGCCTCGGCCTCTGAGC
TATTCCAGAAGTAGTGAGGAGGCTTTTTGGAGGCCTAGGCTTTTGCAAAAAGCTcccg
gggcggccgccaccatgggcagcaagcccagcacctggatcagcgtgaccctgatgctg

Figure 14CC

```
atcaccagaaccatgctgatcctgagctgcatctgccccacaagcagcctggacggcag
acccctggccgctgccggcatcgtggtgaccggcgacaaggccgtgaacatctacacca
gcagccagaccggcagcatcatcatcaagctgctgcccaacatgcccaaggacaaagag
gcctgcgccaaggccccctggaagcctacaacagaaccctgaccaccctgctgaccccc
cctgggcgacagcatcagaagaatccagggcagcgccaccacaagcggcggaggaaagc
agggcagactggtgggcgctatcatcgggagcgtggccctgggcgtggccacagctgcc
cagattaccgctgcagccgccctgattcaggccaatcagaacgccgccaacatcctgag
actgaaagagagcattgccgccaccaacgacgccgtgcacgaagtgacaaacggactgt
cccagctggctgtcgctgtcggcaagatgcagcagttcgtgaacaaccagttcaacaac
accgccagagagctggactgcatcaagatcgcccagcaggtgggcgtggagctgaacct
gtacctgaccgagctgaccacagtgttcggcccccagatcacaagcccgctctgaccc
agctgacaatccaggccctgtacaacctggctggcggcaacatggactatctgctgact
aagctgggagtgggcaacaaccagctgtccagcctgatcgggtccgggctgatcacagg
caaccccatcctgtacgacagccagacacagctgctgggcatccagatcaacctgccat
ccgtgggaagcctgaacaacatgagagccacctacctggaaaccctgagcgtgtccacc
accaagggcttcgccagcgccctggtgcccaaggtggtgacacaggtgggcagcgtgat
cgaggaactggacaccagctactgcatcgagagcgacatcgacctgtactgcaccagag
tggtgaccttcccaatgagccccggcatctacagctgcctgagcggcaacaccagcgcc
tgcatgtacagcaagaccgaaggagcactgacaacaccctacatggccctgaagggaag
cgtgatcgccaactgcaagatgaccacctgcagatgcgccgaccccccaggcatcatca
gccagaactacggcgaggccgtgagcctgatcgacaaacattcctgtagcgtgctgtcc
ctggatggcatcacactgagactgagcggcgagttcgacgccacctaccagaagaacat
cagcatcctggacagccaggtgatcgtgaccggcaacctggacatcagcaccgagctgg
gcaacgtgaacaacagcatcagcagcaccctggacaagctggccgagtccaacaacaag
ctgaacaaagtgaacgtgaacctgaccagcacaagcgccctgatcacctacatcgtgct
ggccatcgtgtccctggccttcggcgtgatcagcctggtgctggcctgctacctgatgt
acaagcagagagcccagcagaaaaccctgctgtggctgggcaataacaccctggaccag
atgagggccaccaccagaacctgatgagcggccgcgatatcaataaaatatctttattt
tcattacatctgtgtgttggttttttgtgtgaatcgatagtactaacatacgctctcca
tcaaaacaaaacgaaacaaaacaaactagcaaaataggctgtccccagtgcaagtgcag
gtgccagaacatttctcttctagacctgcaggatatgttgtccattatgttgtacat
aatcgtyatgtagtgctacgaaatgtcaattgacagccatacatggtgctaatagc
gttacttctagtatgcgagtgaataaaaatattaccctatgatactgcgtcttta
tgctacaagttccttcaccatgaccagagccggtgcgatcatattcgacaacttggata
ttcccagagytagatttggccagccgcggggaaaataaatgacttcaactactggacc
ttgctaaccgatgagctgacgtgtggaattattcaatgtatggagtcgcgcgagcgaat
tgccctagtgcattcagcaacatacgatcatggtcagtttgacatacaaaagatatgt
ggtgtcaaatagttctatggtctgctataggtttcttcccacactagaacgtagtttt
tcaattaaaagtgtcttagagtttggagatacaaacgtgaacggaagtgccaatttgc
aatcaattgcacgccatgggatttgagagattcgccgaaaatgaaatgtttggaacac
tcttgccggcttgttttctttccattagaaaattggacgacgatgtctcaatcggc
gctagtaaaggatattctcagtgtaatttgcgacagattttatgagaaatccatcctt
taaaaacgttattatagcctccctggagyttgcgagatctgctattgtccttaccatcc
caatatgcaatatagaactccccaggyctgccggacgattacatcggaaatgccata
aagttgtgctgtgccagaatgaacatctgagactgaacatcctggccaatgtataga
tcaaatgtgcagcgatccttcagaagagaaatgtattacagatatgtccaacgactcg
```

Figure 14DD

```
taacgagcggcaataaatattcagaatcatcggaaaatttccgaatgagtgtggaccca
cgcgttgttggtccccgattgcgcgactgtcaatacgaatccatacgggcaaggtatcc
gagcggtaccagggcgggatatgggacaaccggaagatatccaaataatggacgtttca
aattttcacgattccaagtaaggcactatccacagtacgttccaagatcgaagctggca
aacagtaaaattatccagactcttaacgaatgtaatgatagatccatttta
```

RECOMBINANT HVT VECTORS EXPRESSING ANTIGENS OF AVIAN PATHOGENS AND USES THEREOF

INCORPORATION BY REFERENCE

This application is a continuation of U.S. application Ser. No. 13/689,625 filed on Nov. 29, 2012, now U.S. Pat. No. 9,114,108, which is incorporated herein by reference in its entirety, which claims priority to U.S. provisional application 61/564,877 filed on Nov. 30, 2011 and U.S. provisional application 61/694,957 filed on Aug. 30, 2012.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 2 and 3 (HVT) (WO-A-87/04463), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84; U.S. Pat. No. 5,980,906). Other HVT vectors of interest are those expressing either NDV (Morgan et al 1992, Avian dis. 36, 858-70; U.S. Pat. No. 6,866,852; U.S. Pat. No. 5,650,153) or ILTV (Johnson et al, 2010 Avian Dis 54, 1251-1259; U.S. Pat. No. 6,299,882; U.S. Pat. No. 5,853,733) protective gene(s). One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancún, Mexico, Aug. 14-18, 2011). The combination of HVT and SB-1, a Gallid herpesvirus 3 (MDV serotype 2 or MDV-2) vaccine strain, has shown a synergistic effect on MD protection (Witter and Lee, 1984, Avian Pathology 13, 75-92). To address the interference problem, it is of interest to evaluate the HVT virus as a vaccine vector to express one or more protective antigen(s) against a variety of avian pathogens.

The SB-1 genome was cloned and characterized in bacterial artificial chromosome (BAC) (Petherbridge, et al., J. Virol. Methods 158, 11-17, 2009; Singh et al., Research in Veterinary Science 89, 140-145, 2010). The MDV2 SB-1 sequence was recently obtained and analyzed (Spatz and Schat, Virus Gene 42, 331-338, 2011). A glycoprotein E deletion of SB-1 virus was described by Petherbridge, et al. (J. Virol. Methods 158, 11-17, 2009). However, no research has been reported using SB-1 as a viral vector expressing foreign protective genes.

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between two HVT-based vector vaccines.

SUMMARY OF THE INVENTION

The present invention showed surprising result when polyvalent compositions or vaccines comprising single or double HVT vector were effective to protect animals against a variety of avian pathogens without interference. Surprising results were also observed when various combinations of promoters, codon-optimized gene, polyA tails and insertion sites conferred different levels of efficacy and stability to the expression of one or more heterologous genes in vivo.

The present invention relates to a recombinant HVT vector comprising one or more heterologous polynucleotides coding for and expressing at least one antigen of an avian pathogen.

The present invention provides a composition or vaccine comprising one or more recombinant HVT vectors comprising one or more heterologous polynucleotides coding for and expressing at least one antigen of an avian pathogen.

The present invention provides a polyvalent composition or vaccine comprising one or more recombinant HVT vectors comprising heterologous polynucleotides coding for and expressing at least one antigen of an avian pathogen and one or more recombinant SB1 vectors comprising heterologous polynucleotides coding for and expressing at least one antigen of an avian pathogen.

The present invention relates to a method of vaccinating an animal, or inducing an immunogenic or protective response in an animal, comprising at least one administration of the composition or vector of the present invention.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 3 depicts the plasmid map of pHM103.

FIG. 5A1 and FIG. 5A2 are from the pre-MSV passage. FIG. 5B1 and FIG. 5B2 are from the pre-MSV+12 passage.

FIG. 6 depicts the Southern blot results of vHVT114.

FIG. 9 depicts the Western blot analysis of immunoprecipitated sample from vSB1-009 infected cells.

FIG. 10 depicts the result of challenge study of vHVT304 and vHVT114 against NDV ZJ1 and CA02.

FIG. 11 depicts the viral shedding result after NDV CA02 and ZJ1 challenge. FIG. 11A depicts the vial shedding result after CA/02 challenge. FIG. 11B depicts the vial shedding result after ZJ1 challenge.

FIG. 12A and FIG. 12B depict the viral shedding result after NDV Chimalhuacan challenge.

FIG. 13 shows the sequence alignment and percentage identity.

Figure 14T:
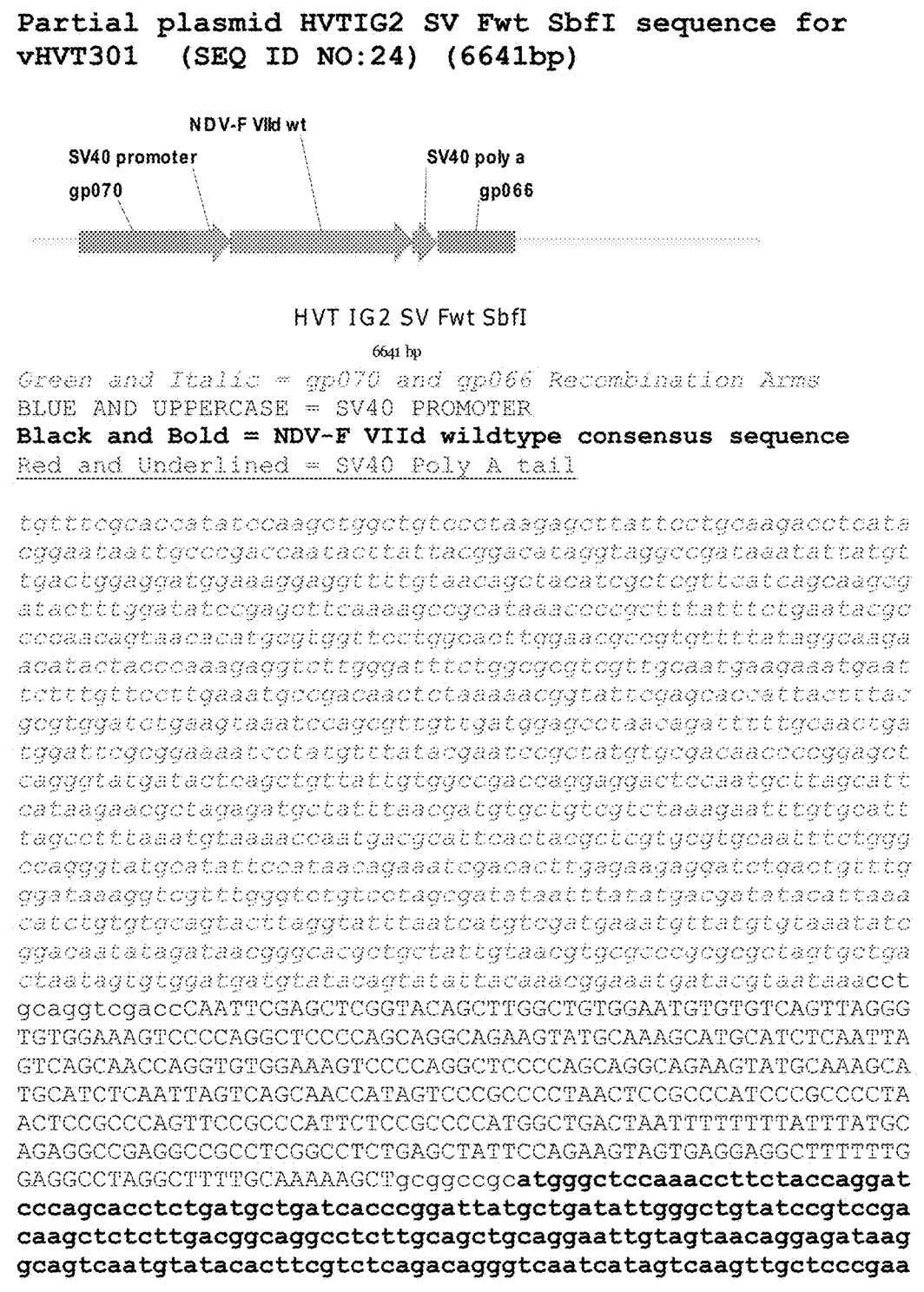

FIG. 14 shows the DNA and protein sequences.

DETAILED DESCRIPTION OF THE INVENTION

Figure 2:
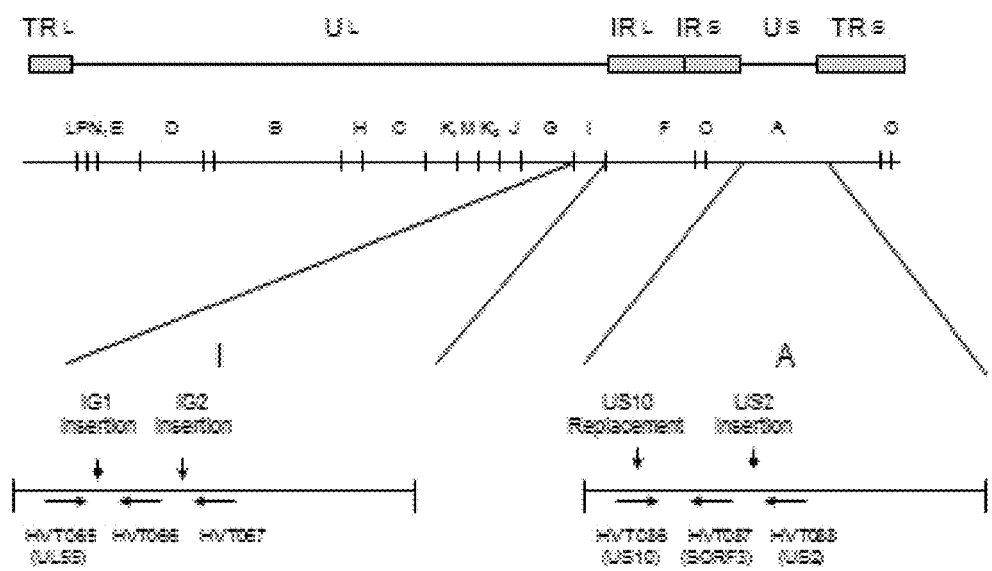
FIG. 2 depicts the genome structure of HVT and its insertion sites.

It is noted that in this disclosure and particularly in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one ore more nucleotides or amino acids, deletion of an entire gene, codon-optimization of a gene, conservative substitution of amino acids, insertion of one or more heterologous polynucleotides.

The term "double HVT construct" or "double HVT vector" refers to an HVT viral vector comprising two heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the invention provides a recombinant HVT viral vector comprising one or more heterologous polynucleotides coding for and expressing at least one antigen or polypeptide of an avian pathogen. The HVT strains used for the recombinant viral vector may be any HVT strains, including, but not limited to, the HVT strain FC126 (Igarashi T. et al., J. Gen. Virol. 70, 1789-1804, 1989).

Another embodiment of the invention provides a recombinant SB-1 viral vector comprising one or more heterologous polynucleotides coding for and expressing at least one antigen or polypeptide of an avian pathogen. The SB-1 strains may be any SB-1 strains, including, but not limited to, the commercial Marek's Disease Vaccine (SB-1 vaccine) (Merial Select Inc., Gainesville, Ga. 30503, USA), the SB-1 strain having the genome sequence as defined by GenBank Accession Number HQ840738.1.

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), Infectious Bursal Disease Virus (IBDV) VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemaglutinin (HA), influenza neuraminidase (NA), protective genes derived from *Mycoplasma gallisepticum* (MG), or *Mycoplasma synoviae* (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *E. coli.*

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant HVT or SB-1 viral vector comprising one or more heterologous polynucleotides coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 4, or 6, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encoding an NDV-F antigen or polypeptide having at least 70%, 75%, 80%, 85%, 90%, 95%, 96%, 97%, 98% or 99% sequence identity to a polypeptide having the sequence as set forth in SEQ ID NO:2, 4, or 6. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1, 3, or 5.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F polypeptides, the DNA sequence of the NDV-F protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F polypeptide encoded by the nucleotide sequence is functionally unchanged.

Successful expression of the heterologous polynucleotides by the recombinant/modified infectious virus requires two conditions. First, the heterologous polynucleotides must be inserted or introduced into a region of the genome of the virus in order that the modified virus remains viable. The second condition for expression of inserted heterologous polynucleotides is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

The insertion site may be any non-essential region of the HVT genome, including, but not limited to, the region between the ATG of ORF UL55 and the junction of UL with the adjacent repeat region (U.S. Pat. No. 5,980,906), the IG1 locus, the IG2 locus, the IG3 locus, the UL43 locus, the US10 locus, the SORF3/US2 locus (see FIG. 2)

In general, it is advantageous to employ a strong promoter functional in eukaryotic cells. The promoters include, but are not limited to, an immediate early cytomegalovirus (CMV) promoter, an SV40 promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, Infectious Laryngotracheitis Virus promoters such as those of glycoprotein gB, gE, gI, gD genes, or other herpesvirus promoters.

One embodiment of the invention provides a recombinant HVT vector comprising a heterologous polynucleotide coding for and expressing the NDV-F antigen or polypeptide. In one aspect of the embodiment, the polynucleotide encoding the NDV-F polypeptide is operably linked to the SV40 promoter having the sequence as set forth in SEQ ID NO:9 and therefore the expression of the NDV-F antigen or polypeptide is regulated by the SV40 promoter. In another aspect of the embodiment, the expression of NDV-F antigen or polypeptide is regulated by the SV40 polyA signal having the sequence as set forth in SEQ ID NO:11.

Another embodiment of the invention provides a recombinant double HVT vector comprising a first heterologous polynucleotide coding for and expressing the NDV-F antigen or polypeptide and a second polynucleotide coding for and expressing the IBDV VP2 antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 4, or 6. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:8. In another aspect, the polynucleotide encoding the NDV-F polypeptide is operably linked to the SV40 promoter having the sequence as set forth in SEQ ID NO:9 and the expression of NDV-F antigen or polypeptide is regulated by the SV40 promoter. In yet another aspect, the expression of NDV-F antigen or polypeptide is regulated by the SV40 polyA signal having the sequence as set forth in SEQ ID NO:11, or the synthetic polyA singal having the sequence as set forth in SEQ ID NO:12. In another aspect, the expression of IBDV VP2 antigen or polypeptide is regulated by the CMV-IE promoter having the sequence as set forth in SEQ ID NO:10 and the SV40 polyA signal having the sequence as set forth in SEQ ID NO:11.

In one embodiment, the present invention relates to a pharmaceutical composition or vaccine comprising one or more recombinant HVT or SB-1 rival vectors of the present invention and a pharmaceutically or veterinarily acceptable carrier, excipient, vehicle or adjuvant.

In another embodiment, the present invention provides a composition or vaccine comprising an HVT viral vector comprising a polynucleotide encoding an NDV-F antigen, an SV40 promoter, and optionally a pharmaceutically or veterinarily acceptable carrier, excipient, vehicle or adjuvant. In another embodiment, the present invention provides a pharmaceutical composition or vaccine comprising a first HVT vector comprising a polynucleotide encoding an NDV-F antigen, a second HVT vector comprising a polynucleotide encoding an IBDV VP2 antigen, and optionally a pharmaceutically or veterinarily acceptable carrier, excipient, vehicle or adjuvant. In another embodiment, the present invention provides a pharmaceutical composition or vaccine comprising an HVT vector comprising a polynucleotide encoding an NDV-F antigen, an SB-1 vector comprising a polynucleotide encoding an NDV-F antigen, optionally a pharmaceutically or veterinarily acceptable carrier, excipient, vehicle or adjuvant. The pharmaceutical composition or vaccine of the present invention may comprise a first HVT vector comprising a polynucleotide encoding an NDV-F antigen, a second HVT vector comprising a polynucleotide encoding an IBDV VP2 antigen, an SB-1 vector comprising a polynucleotide encoding an NDV-F antigen, optionally a pharmaceutically or veterinarily acceptable carrier, excipient, vehicle or adjuvant.

In yet another embodiment, the present invention provides a composition or vaccine comprising a double HVT viral vector comprising: i) a first heterologous polynucleotide coding for and expressing an NDV-F antigen or polypeptide; ii) a second polynucleotide coding for and expressing an IBDV VP2 antigen or polypeptide; and iii) optionally a pharmaceutically or veterinarily acceptable carrier, excipient, vehicle or adjuvant. In yet another embodiment, the composition comprising the double HVT viral vector further comprises an HVT vector comprising a polynucleotide encoding an IBDV VP2 antigen, or an SB-1 vector comprising a polynucleotide encoding an NDV-F antigen, or a combination thereof.

The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek's disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvant or vehicles or excipients, including, but not limited to, alum; CpG oligonucleotides (ODN), in particular ODN 2006, 2007, 2059, or 2135 (Pontarollo R. A. et al., *Vet. Immunol. Immunopath*, 2002, 84: 43-59; Wernette C. M. et al., *Vet. Immunol. Immunopath*, 2002, 84: 223-236; Mutwiri G. et al., *Vet. Immunol. Immunopath*, 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology*, 6: p. 03, p. 157); N,N-dioctadecyl-N',N'-bis(2-hydroxyethyl) propanediamine (such as AVRIDINE®) (Ibid, p. 148); carbomer, chitosan (see U.S. Pat. No. 5,980,912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum*, *Mycoplasma synoviae*, *Pasteurella* sp., *Avibacterium* sp., *E. coli* or *Clostridium* sp.

Usually, one administration of the vaccine is performed either at one day-of-age by the subcutaneous or intramuscular route or in ovo in 17-19 day-old embryo. A second administration can be done within the first 10 days of age. The animals are preferably at least 17 day-embryo or one day old at the time of the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of Recombinant vHVT114 Expressing NDV-F

Preparation of Donor Plasmid pHM103+Fopt

The plasmid pHM103 (Merial Limited) containing the Intergenic I arms of HVT FC126 (see FIG. 2), SV40 promoter and SV40 poly A was digested with NotI, dephosphorylated, and the 5.6 kb fragment was gel extracted. A NotI flanked 1.7 kb fragment of a chemically synthesized codon-optimized genotype VIId NDV-F gene(SEQ ID NO:1, coding for SEQ ID NO:2) was also NotI digested and the 1.7 kb fragment was gel extracted. The 5.6 and 1.7 kb fragments were ligated to create pHM103+Fopt (FIG. 3).

Generation of Recombinant HVT Viral Vector

An in vitro recombination (IVR) was performed by co-electroporation of secondary chicken embryo fibroblast cells (2° CEF cells) using pHM103+Fopt as the donor plasmid and viral DNA isolated from the HVT strain FC126. Co-electroporation was performed using $1\times10^7$ 2° CEF in 300 ul Opti-MEM and shocked at 150 volts with 950 capacitance in a 2 mm electroporation cuvette. The transfected cells were seeded into 96-well plate and incubated for 5 days. The cells grown in the 96-well plate were then duplicated into two 96-well plates. One set of 96-well plates was used for IFA using chicken polyclonal sera against NDV-F to identify positive wells containing recombinants and another set of 96-well plates was used for recovering the infected cells from the positive wells.

The recombinant viral purification was performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock, 5-20 ul were removed and mixed with $1\times10^7$ CEFs in 10 ml DMEM+2% FBS and aliquoted onto a new 96-well plate to have single HVT plaques per well. The supernatant of the wells that contained single plaques were tested for the absence of parental virus by PCR. After five rounds of plaque purification, a recombinant virus designated as vHVT114 was isolated and the purity was tested by IFA and PCR to confirm NDV-F expression and the absence of parental virus.

PCR Analysis of Recombinant vHVT114

DNA was extracted from vHVT114 by phenol/chloroform extraction, ethanol precipitated, and was resuspended in 20 mM HEPES. PCR primers (shown in Table 1) were designed to specifically identify the presence of the codon optimized NDV-F, the SV40 promoter, as well as, the purity of the recombinant virus from FC126 CL2 parental virus. PCR was performed using 200 ng of DNA template along with the specified primers pairs indicted in Table 1. PCR cycling conditions are as follows: 94° C. for 2 mins; 30 cycles of 94°

Figure 4:
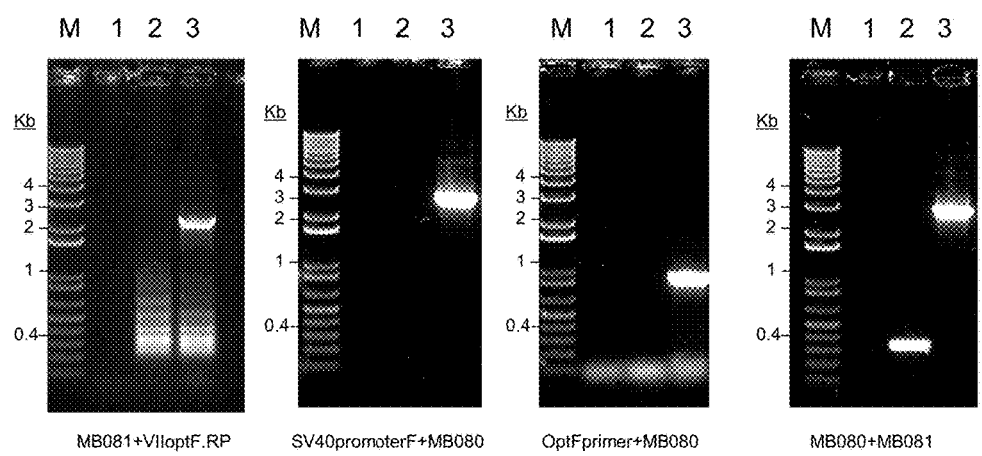
FIG. 4 depicts the PCR analysis results of vHVT114.

C. for 30 secs, 55° C. for 30 secs, 68° C. for 3 mins; 68° C. for 5 mins. The expected PCR products are shown in Table 2. The PCR results are shown in FIG. 4. As shown in FIG. 4, the sizes of PCR products after gel electrophoresis correspond well with the expected sizes and the banding patterns.

TABLE 1

| primer | SEQ ID NO | Sequence 5'-3' |
|---|---|---|
| MB080 | 13 | CGA ACA AAC TTC ATC GCT ATG C |
| MB081 | 14 | TAA CTC AAA TGC GAA GCG TTG C |
| optF | 15 | ACT GAC AAC ACC CTA CAT GGC |
| VIIoptF RP | 16 | GCC AGC ACC AGG CTC AGG G |
| SV40promoterF | 17 | AGC TTG GCT GTG GAA TGT |

TABLE 2

| | Expected size (bp) | |
|---|---|---|
| Primer pairs | FC126 CL21 | vHVT114 |
| MB081 + VIIoptF.RP | — | 2138 |
| SV40promoterF + MB080 | — | 2368 |
| OptFprimer + MB080 | — | 872 |
| MB080 + MB081 | 323 | 2578 |

Expression Analysis of Recombinant vHVT114

Immunofluorescence testing was performed using the vHVT114 which was passaged over ten times beyond an experimental pre-master seed (pre-MSV). The pre-MSV and pre-MSV+12 materials were diluted 1:100 in media. Fifty microliters of the diluted virus was added to 10 ml of DMEM+2% FBS with $1 \times 10^7$ CEFs and then aliquoted onto a 96 well plate (100 ul/well). The plates were incubated for 3 days at 37° C.+5% $CO_2$ until viral plaques were visible. The plates were fixed with 95% ice-cold acetone for three minutes and washed three times with PBS. Chicken anti-sera against Newcastle Disease Virus (lot #C0139, Charles Rivers Laboratory) at 1:1000 were added along with monoclonal antibody L-78 (Merial Limited) at 1:3000 and the plates were incubated at 37° C. for 1 hour. After the 1 hour incubation the plates were washed three times with PBS and FITC anti-chicken (cat #F8888, Sigma) was added along with Alexz Fluor 568 donkey anti-mouse (IgG) (cat #A 10037, Molecular Probe) at 1:500. Again the plates were incubated at 37° C. for 1 hour. After the 1 hour incubation the cells were rinsed three times with PBS. A small amount of PBS was added to prevent the monolayer from drying and causing auto fluorescence. The cells were then visualized with a fluorescent microscope using both the tetramethyl-rhodamine isothiocyanate (TRITC) and fluorescein isothiocyanate (FITC) filters in combination.

Figure 5:
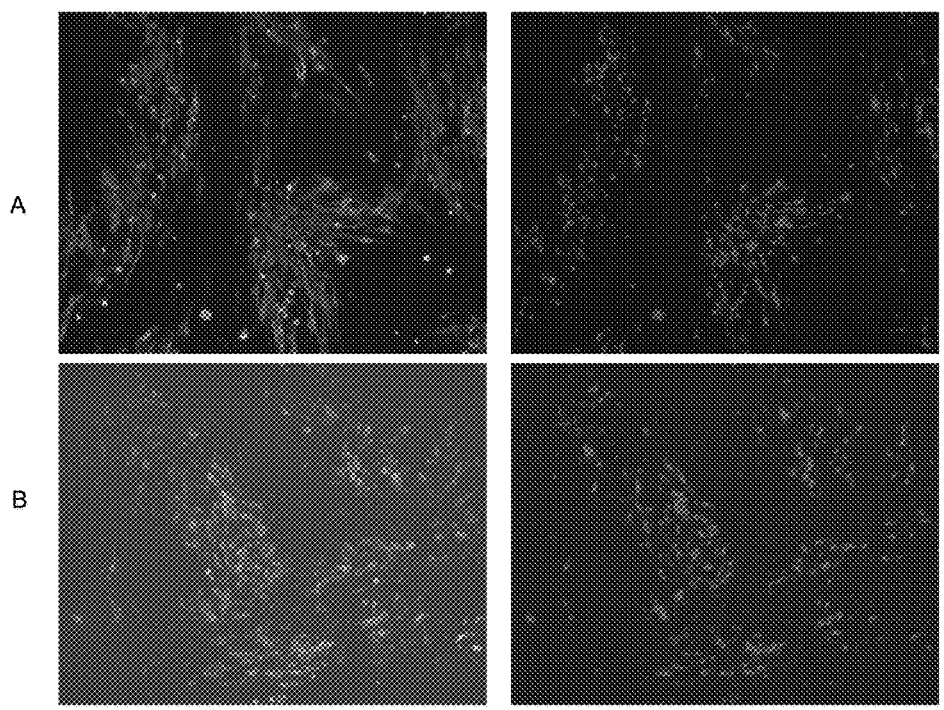
FIG. 5 shows the dual immunofluorescent assay results.

The vHVT114 viral plaques were visualized using both the TRITC and FITC filters for the dual staining. The FITC test showed the NDV-F expression and the TRITC test showed the HVT expression. Because of the small wells of the 96 well plates, each well was recorded with the plaques first counted with the TRITC filter and then recounted with the FITC filter. Over 500 plaques were counted for the pre-MSV and pre-MSV+12 passage. All the plaques were positive for both the FITC and TRITC on both plates. (FIG. 5)

Southern Blot Analysis of Recombinant vHVT114

Total genomic DNA was extracted from HVT FC126 and vHVT114 according to the standard genomic DNA extraction protocol. For each restriction digest, 3 μg of genomic DNA (1 ng for the donor plasmid) was used with a total digestion volume of 20 μl for each sample. The genomic DNA of HVT FC126 (negative control), pHM103+Fopt donor plasmid, and vHVT114 were each digested overnight at 37° C. with BamHI, PstI, SphI, and NcoI restriction endonucleases. The restriction fragments of HVT FC126 (negative control), pHM103+Fopt donor plasmid, and vHVT114 genomic DNA were separated by a 1% agarose gel and transferred to a positively charged Nylon membrane. Following the North2South Chemiluminescent Hybridization and Detection Kit (Thermo Scientific) manufacturers' instructions, the membrane was pre-hybridized for 1 hr and then hybridized with a biotinylated NDV-F probe overnight at 55° C. Following the overnight hybridization, several stringency washes were performed until the membrane was placed in blocking buffer with the addition of Streptavidin-HRP. After rinsing the membrane of any unbound Streptavidin-HRP the substrate solution of Luminal and peroxide were added. The membrane was then exposed to X-ray film and developed. Areas where the biotinylated probe bound to the DNA were chemiluminescent and were captured by the X-ray film. Table 3 shows the expected Southern blot bands using the NDV-F probe. The Southern blot results showed the digestion patterns as expected (FIG. 6).

TABLE 3

| | NDV-F Probe | | |
|---|---|---|---|
| Restriction Endonuclease | Donor plasmid pHM103 + Fopt | vHVT114 | FC126 CL2 |
| BamHI | 7.014 | 6.630 | |
| | 0.198 | 1.259 | — |
| | | 0.198 | |
| PstI | 5.481 | 6.359 | |
| | 0.947 | 0.947 | — |
| | 0.784 | 0.784 | |
| SphI | 4.763 | 2.377 | |
| | 2.377 | 2.119 | — |
| | 0.072 | 0.072 | |
| NcoI | 4.931 | 3.753 | |
| | 2.157 | 2.157 | — |
| | 0.124 | 0.124 | |

Sequence Analysis of the Inserted Region in Recombinant vHVT114

Analysis of vHVT114 genomic DNA region was performed by PCR amplification. Total of 10 primers were used to amplify the entire cassette, as well as, beyond the flanking BamHI-I arms used in the donor plasmid. The 4.727 kb PCR product was gel purified and the entire fragment was sequenced using the sequencing primers. The sequence result confirmed that the vHVT114 contains the correct SV40 promoter, the codon-optimized NDV-F and the SV40 polyA sequences that match exactly the sequence described for the donor plasmid pHM103+Fopt in SEQ ID NO:18.

Western Blot Analysis of Recombinant vHVT114

Approximately $2 \times 10^6$ chicken fibroblast cells were infected at ~0.1 MOI with vHVT114 Pre-MSV. After two days of incubation at 37° C., infected as well as uninfected cells were harvested using a cell scraper after removing the media and rinsing with PBS. The cells were harvested with 1 ml of PBS and centrifuged. The cell pellets were lysed by following the Pierce Classic IP Kit (cat #26146, Thermo Scientific). 100 µl of the anti-NDV-F monoclonal antibody 001C3 (Merial Limited) was used to form the immune complex. The antibody/lysate sample was added to Protein A/G Plus Agarose to capture the immune complex. The immune complex was washed three times to remove non-bound material and then eluted in 50 ul volume using sample buffer elution under non-reducing condition. After boiling for 5 minutes, 10 µl of the samples were loaded into a 10% Acrylamide gel (Invitrogen). The PAGE gel was run in MOPS buffer (Invitrogen) at 200 volts for 1 hour. Then the gel was transferred onto a PVDF membrane.

The Protein Detector Western Blot Kit TMB System (KPL, cat #54-11-50) was used for blotting the PVDF membrane by using the reagents and following manufacturer's directions. After blocking the membrane for 1 hour at room temperature, the membrane was then rinsed three times in 1× Wash Buffer, five minutes each and then soaked in blocking buffer containing 1:1000 dilution of chicken serum raised against NDV virus (Lot #C0139, Charles River Laboratories). After washing three times in a washing buffer, the membrane was incubated with a peroxidase labeled goat anti-chicken IgG (KPL, cat #14-24-06) at a dilution of 1:2000 for 1 hour at room temperature. The membrane was then rinsed three times in 1× Wash Buffer, five minutes each. 5 ml of TMB membrane peroxidase substrate was added to the membrane and gently rocked for about 1 minute. The developing reaction was stopped by placing the membrane into water.

Figure 7:
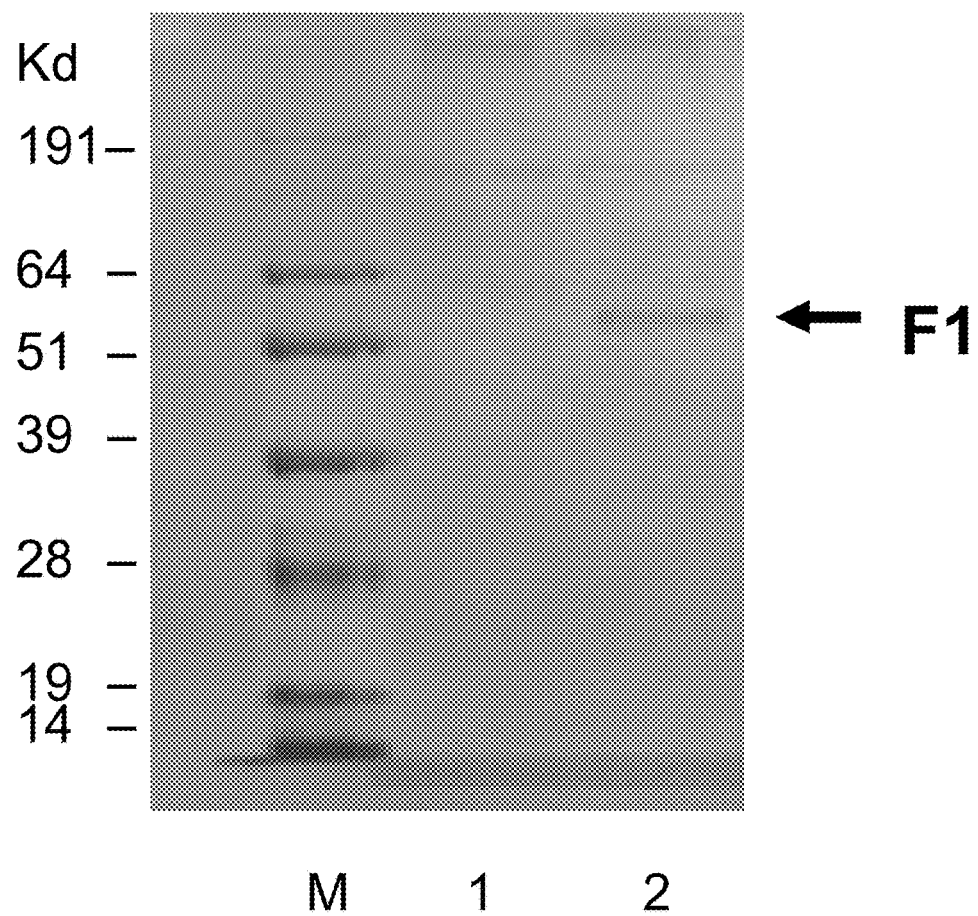
FIG. 7 depicts the immunoprecipitation and Western blot analysis results of vHVT114.

The immunoprecipitation and Western blot technique detected an approximately 55 kD protein in vHVT114 sample that corresponds to the expected size of F1 component of the NDV-F protein (FIG. 7).

Example 2

Construction of Recombinant vHVT110, vHVT111 and vHVT116 Expressing NDV-F

Generation and characterization of HVT recombinants vHVT110, vHVT111 and vHVT116 was essentially done in the same way as for vHVT114 described in example 1. Table 4 shows the features unique to each construct around the expression cassettes, including the respective sequences.

TABLE 4

Characteristics of the expression cassettes of single HVT recombinants

| Name | Parental virus | Promoter | F gene | Poly-A | Locus |
| --- | --- | --- | --- | --- | --- |
| vHVT110 | HVT | mCMV IE | Wt-VIId | SV40 | IG1 |
| vHVT111 | HVT | SV40 | Wt-VIId | SV40 | IG1 |
| vHVT114 | HVT | SV40 | Opt-VIId | SV40 | IG1 |
| vHVT116 | HVT | SV40 | Opt-Ca02 | SV40 | IG1 | vHVT110

The plasmid pCD046 (Merial proprietary material) containing the Intergenic I arms of HVT FC126, mouse CMV promoter and SV40 poly A was digested with NotI, dephosphorylated, and a 6.6 kb fragment was gel extracted. A NotI flanked 1.7 kb fragment of a chemically synthesized NDV-F gene containing wild-type F sequence (SEQ ID NO:3, coding for SEQ ID NO:4) was also NotI digested and the 1.7 kb fragment was gel extracted. The 6.6 and 1.7 kb fragments were ligated to create a donor plasmid pCD046+NDV-F wt (SEQ ID NO:21 for vHVT110) used in transfection to generate recombinant vHVT110. Sequencing of the insert region confirmed that vHVT110 contains the correct sequences of mCMV promoter, the wildtype NDV-F gene and the SV40 polyA. The sequence also exactly matches the sequence described for the donor plasmid pCD046+NDV-F wt in SEQ ID NO:21.

vHVT111

The plasmid pHM103 plasmid (Merial proprietary material) containing the Intergenic I arms of HVT FC126, SV40 promoter and SV40 polyA was digested with NotI, dephosphorylated, and the 5.6 kb fragment was gel extracted. A NotI flanked 1.7 kb fragment of a chemically synthesized NDV-F gene containing wildtype F sequence (SEQ ID NO:3, coding for SEQ ID NO:4) was also NotI digested and a 1.7 kb fragment was gel extracted. The 5.6 and 1.7 kb fragments were ligated to create a donor plasmid (SEQ ID NO:22 for vHVT1110) used in transfection to generate recombinant vHVT111. Sequencing of the insert region confirmed that vHVT111 contains the correct sequences of SV40 promoter, the wildtype NDV-F gene and the SV40 polyA as shown in the sequence of the donor plasmid pHM103+NDV-F wt (SEQ ID NO:22).

vHVT116

The plasmid pHM103 plasmid (Merial proprietary material) containing the Intergenic I arms of HVT FC126, SV40 promoter and SV40 polyA was digested with NotI, dephosphorylated, and the 5.6 kb fragment was gel extracted. A NotI flanked 1.7 kb fragment of a chemically synthesized, codon-optimized, CA02 genotype V NDV-F gene (SEQ ID NO:5, coding for SEQ ID NO:6) was also NotI digested and the 1.7 kb fragment was gel extracted. The 5.6 and 1.7 kb fragments were ligated to create pHM103+NDV-F CA02 (SEQ ID NO:23 for vHVT116) used in transfection to generate recombinant vHVT116. Sequencing of the insert region confirmed that vHVT116 contains the correct sequences of SV40 promoter, the codon-optimized CA02 NDV-F gene and the SV40 polyA as shown in the sequence of the donor plasmid pHM103+NDV-F wt (SEQ ID NO:23).

Discussion

Various cassettes under mCMV or non-CMV promoter were inserted at different loci of HVT genome (Table 4). Despite repeated attempts, generating a construct with a combination of mCMV and codon-optimized F sequence was not successful beyond passage 2. However, when wild-type sequence was driven by mCMV a stable construct, vHVT110 could be generated. In addition, recombinant vHVT111 with wild-type F sequence under SV40 promoter was also stable for more than 10 in vitro passages. Surprisingly, a codon-optimized F sequence under SV40 promoter was similarly found to be stable for more than 10 in vitro passages (e.g. vHVT114 and vHVT116). These results indicate the delicate balance between the strength of the promoter and the nature of the gene they control (codon-optimized or not optimized) in generating a genetically stable HVT construct.

Example 3

Construction of vHVT306, a Double HVT Vector Expressing NDV-F and IBDV VP2

The donor plasmid pHVT US2 SV-Fopt-synPA was constructed containing SV40 promoter, synthetic NDV F codon optimized VII gene, synthetic polyA tail flanked by the SORF3 and US2 arm sequences of HVT FC126.

Generation of Recombinant Virus

A standard homologous recombination procedure was followed by co-electroporation of secondary CEF cells using donor plasmid pHVT US2 SV-Fopt-synPA and viral DNA isolated from vHVT13 (an HVT vector expressing the IBDV VP2 gene, Merial Limited). Essentially the procedure described in example 1 for vHVT114 was followed to generate, plaque purify and characterize recombinants by immunofluorescence.

After two rounds of plaque purification, pure recombinant virus (vHVT306) was isolated and the purity of vHVT306 was tested and confirmed by IFA and PCR.

PCR Analysis

Viral DNA was extracted from vHVT306 pre-master seed virus (pre-MSV) stock by QIA DNeasy Blood & Tissue Kit (Qiagen cat #69506). PCR primers were designed to identify the presence of the NDV F optimized, the NDV F wild type, the SV40 promoter, the mCMV promoter, the flanking arms of US2 HVT virus and SB-1 virus.

PCR amplification with various primers confirmed that the vHVT306 has the expected amplification patterns and amplicons.

Expression Analysis

Indirect immunofluorescent assay (IFA) was performed on the vHVT306 pre-MSV stock. The CEFs that were inoculated with vHVT306 were fixed with ice-cold 95% acetone for three minutes at room temperature and air-dried for 10 min. After three washes with PBS, two primary antibodies, chicken anti-Newcastle Disease Virus sera (Charles Rivers Laboratories cat #10100641, lot #C0117A) at 1:500 dilution and L78 monoclonal antibody against HVT (Merial Select, Gainesville, Ga.) at 1:3000 dilution were added and incubated for 45 min at 37° C. After three washes with PBS, two secondary antibodies, goat anti-chicken IgG—fluorescein (KPL cat #.02-24-06, lot #110020) at 1:500 dilution and donkey anti-mouse IgG-Alexa Fluor 568 (Molecular Probe #A10037, lot #989784) at 1:300 dilution were added. The plates were incubated at 37° C. for 45 min and followed by three washes with PBS. The cells were observed to identify the IFA positive plaques with a fluorescent microscope using fluorescein isothiocyanate (FITC)- and tetramethylrhodamine isothiocyanate (TRITC)-filters of Nikon Eclipse Ti inverted microscope.

Similarly the expression of IBDV VP2 protein (SEQ ID NO:8 encoded by SEQ ID NO:7) of vHVT306 were examined by IFA using chicken anti-IBDV sera (Charles River Laboratories cat #10100610 lot #G0117) (1:500 dilution) and anti-NDV F monoclonal antibody 001C3 (Asceitic fluid, Batch 10/09/044, 02/11/2010) (1:300 dilution) as primary antibodies; followed by goat anti-chicken IgG-fluorescein (KPL cat #.02-24-06, lot #110020) (1:500 dilution) and donkey anti-mouse IgG-Alexa Fluor 568 (Molecular Probe #A10037, lot #989784) (1:300 dilution) as secondary antibodies.

IFA results indicate that vHVT306 expresses the NDV F genes in virus-infected CEFs.

Over 400 vHVT306 plaques were counted using the FITC-filter and TRITC-filter of microscope. The overall expression of NDV F gene and IBDV VP2 match with the HVT plaques (Table 5).

TABLE 5

Dual IFA of vHVT306

| | IFA #1 (total 453 plaques) | | IFA#2 (total 478 plaques) | |
| --- | --- | --- | --- | --- |
| Virus | Anti-NDV serum positive plaques | Anti-HVT MAb positive plaques | Anti-NDV F MAb positive plaques | Anti-IBDV serum positive plaques |
| vHVT306 pre-MSV | 453 | 453 | 478 | 478 |

Southern Blot Analysis

Total genomic DNA was extracted from vHVT306 pre-MSV stock infected CEFs. The Southern blot analysis was performed according to the standard protocol.

A total 3 probes were used to confirm the NDV F cassette (SV40 promoter, NDV F codon optimized gene, synthetic poly A tail) between SORF3 and US2 of vHVT306 as well as retention of IBDV VP2 cassette (mCMV promoter, IBDV VP2 gene, SV40 poly A tail).

The Southern blot results showed the digestion patterns as expected based on Vector NTI (Invitrogen, 1600 Faraday Ave., Carlsbad, Calif.) map analysis. The NDV F cassette (SV40 promoter, NDV F codon optimized gene, synthetic poly A tail) is located between SORF3 and US2, and IBDV VP2 cassette (mCMV promoter, IBDV VP2 gene, SV40 poly A tail) is intact like the parent virus (vHVT13).

Genomic Analysis

The genomic DNA of vHVT306 pre-MSV stock was sequenced to verify the sequence of the recombination arm region as well as inserted gene cassette.

Primers were designed to amplify the entire inserted gene cassette including recombination arm used in donor plasmid. Analysis of vHVT306 genomic DNA was performed by PCR amplification and followed by nucleotide sequence determination.

The vHVT306 (donor plasmid pHVT US2 SV-Fopt-synPA) containing the recombinant arms, SV40 promoter and NDV F codon-optimized gene was confirmed to be correct as shown in SEQ ID NO:20.

Western Blot Analysis

The CEF monolayer was infected with vHVT306 pre-MSV at MOI~0.1. After a 4-day incubation, the CEFs were pelleted and washed with PBS followed by lysis with IP Lysis/Wash buffer of Pierce Classic IP Kit (Thermo Scientific cat #26146) according to the manufacturer's protocols. The lysate was pre-cleared and incubated with 100 ul of anti-NDV F monoclonal antibody 001C3 to make the immune complex. The immune complex was captured by Protein A/G Plus Agarose and after removing of the unbounded immune complex by washing steps, the 50 ul of sample buffer was used to elute under non-reducing conditions. The uninfected CEFs were included as controls. The 20 ul of eluted samples were separated in a 10% Bis-Tris Gels by electrophoresis. After the electrophoresis, the separated proteins were transferred onto PV DF membrane. The Protein Detection TMB Western Blot Kit (KPL cat #54-11-50) was used to detect the NDV antigens on PVDF membrane with chicken anti-NDV serum (Charles River Laboratories Laboratories cat #10100641, lot #C0117A), and goat anti-chicken IgG-peroxidase conjugate (KPL cat #14-24-06) following the manufacturers' protocols.

Figure 8:
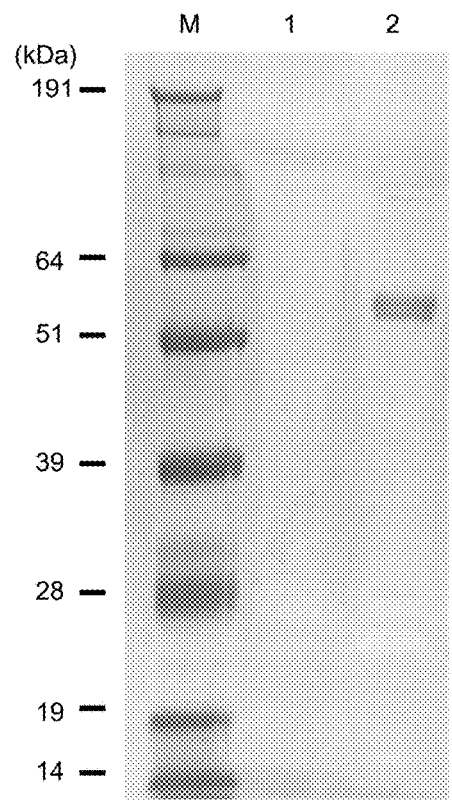
FIG. 8 depicts the Western blot analysis of immunoprecipitated sample from vHVT306 infected cells.

The NDV F protein expression of vHVT306 was confirmed by two-step immunodetection. First, the expressed NDV F proteins from vHVT306 infected CEF were captured by the immunoprecipitation using anti-NDV F monoclonal antibody 001C3. Subsequently Western blot analysis using anti-NDV polyclonal serum (Charles River Laboratories cat #10100641, lot #C0117A) was applied to detect the NDV F protein in the captured samples (NDV F protein-monoclonal antibody complex) (FIG. 8). A 55 kDa protein in vHVT306 pre-MSV lysates was detected by anti-NDV serum which corresponds to the expected size of NDV F1 fusion protein (FIG. 8).

Example 4

Construction of Double HVT Vectors vHVT301, vHVT302, vHVT303, vHVT304 and vHVT307 Expressing NDV-F and IBDV VP2

Generation and characterization of double HVT recombinants vHVT301, vHVT302, vHVT303, vHVT304, and vHVT307 were essentially done in the same way as for vHVT306 described in example 3. Table 6 shows the features unique to each construct around the expression cassettes, including the respective sequences.

TABLE 6

Characteristics of the expression cassettes of double HVT recombinants

| Name | Parental virus | Promoter | F gene | Poly-A | Locus |
|---|---|---|---|---|---|
| vHVT301 | vHVT13 | SV40 | Wt-VIId | SV40 | IG2 |
| vHVT302 | vHVT13 | US10 | Opt-VIId | US10 | US10 |
| vHVT303 | vHVT13 | US10 | Opt-V | US10 | US10 |
| vHVT304 | vHVT13 | SV40 | Opt-VIId | Synthetic | IG2 |
| vHVT306 | vHVT13 | SV40 | Opt-VIId | Synthetic | SORF3-US2 |
| vHVT307 | vHVT13 | SV40 | Opt-V | Synthetic | SORF3-US2 | vHVT301

The plasmid pHVT IG2 SbfI (Merial proprietary material) containing the Intergenic 2 arm sequences of vHVT13. was digested with SmaI, dephosphorylated, and the 4.3 kb fragment was gel extracted. The donor plasmid pHM103+ NDV-F wt containing an SV40 promoter, wildtype NDV-F genotype VIId, SV40 poly A tail was EcoRI and SalI digested, klenow treated, and the 2.3 kb fragment was gel extracted. The two fragments were ligated to create a donor plasmid pHVT IG2 SV Fwt SbfI (SEQ ID NO: 24) used in transfection to generate recombinant vHVT301.

vHVT302

A synthetically synthesized plasmid, pHVT US10 cds, containing the US10 arm sequences of vHVT13 was digested with NotI, dephosphorylated, and the 4.7 kb fragment was gel extracted. A NotI flanked 1.7 kb fragment of a chemically synthesized, codon-optimized, NDV-F genotype VIId was NotI digested and gel extracted. The two fragments were ligated to create a donor plasmid pHVT US10 cds F opt used in transfection to generate recombinant vHVT302. The transcription of the inserted F gene should be driven by the native US10 promoter and be stopped by the native US10 polyA signal. No exogenous promoter or polyA is added to express this insert. Sequencing of the insert region confirmed that vHVT302 contains the correct sequence of the codon-optimized VIId NDV-F gene as shown in the sequence of the donor plasmid pHVT US10 cds F opt (SEQ ID NO: 25).

vHVT303

The synthetically synthesized plasmid pHVT US10 cds containing the US10 arm sequences of vHVT13 was digested with NotI, dephosphorylated, and the 4.7 kb fragment was gel extracted. A NotI flanked 1.7 kb fragment of a chemically synthesized, codon-optimized, NDV-F genotype V was NotI digested and gel extracted. The two fragments were ligated to create a donor plasmid pHVT US10 cds F CAO2 opt used in transfection to generate recombinant vHVT303. As with vHVT302, the transcription of this inserted F gene should also be driven by the native US10 promoter and be stopped by the native US10 polyA signal. No exogenous promoter or polyA is added to express this insert. Sequencing of the insert region confirmed that vHVT303 contains the correct sequence of the codon-optimized NDV-F genotype V as shown in the sequence of the donor plasmid pHVT US10 cds F CA02 (SEQ ID NO: 26).

vHVT304

The donor plasmid pHVT IG2 SbfI containing the Intergenic 2 arm sequences of vHVT13 was digested with SbfI, dephosphorylated, and the 4.3 kb fragment was gel extracted. A synthetically synthesized plasmid containing an SV40 promoter+codon optimized NDV-F genotype VIId+ synthetic poly A tail flanked by SbfI was digested with SbfI and the 2.3 kb fragment was gel extracted. The two fragments were ligated to create a donor plasmid pHVT IG2 SV Fopt syn tail used in transfection to generate recombinant vHVT304. Sequencing of the insert region confirmed that vHVT304 contains the correct sequences of SV40 promoter, the codon-optimized VIId NDV-F gene, and the synthetic poly A tail as shown in the sequence of the donor plasmid pHVT IG2 SV Fopt syn tail (SEQ ID NO:27).

vHVT307

The donor plasmid pHVT US2-SORF3 containing the US2 and SORF3 arm sequences of vHVT13 was digested with SbfI, dephosphorylated, and the 5.1 kb fragment was gel extracted. The plasmid SB-1 UL55 SV CaF syn tail SbfI containing an SV40 promoter+codon optimized NDV-F genotype V+synthetic poly A tail flanked by SbfI was digested with SbfI and the 2.3 kb fragment was gel extracted. The two fragments were ligated to create a donor plasmid pHVT US2 SV-FCA02 opt-synPA used in transfection to generate recombinant vHVT307. Sequencing of the insert region confirmed that vHVT307 contains the correct sequences of SV40 promoter, the codon-optimized VIId NDV-F gene, and the synthetic poly A tail as shown in the sequence of the donor plasmid pHVT US2 SV-FCA02 opt-synPA (SEQ ID NO: 28).

Discussion

One of the main goals of this work was to develop a multivalent avian Herpesvirus-based vector by incorporating multiple protective genes of interest to one avian Herpesvirus backbone (e.g. HVT). A prerequisite for this approach is to define expression cassettes containing appropriate promoter-gene-plyA combinations and evaluate for their genetic stability and ability to protect against the specific disease.

For the purpose of creating an efficacious MD-IBD-ND trivalent vector vaccine, either codon-optimized or non-optimized Newcastle Disease Virus (NDV)-F gene sequences were cloned into vHVT13 backbone (HVT-IBD, a licensed vaccine to simultaneously protect chickens against MD and IBD) under human CMV (mouse CMV is already used in vHVT13). All vHVT-IBD-F constructs under human CMV promoter lost F-protein expression within six passages whether or not the NDV-F sequence is codon-optimized and regardless of the insertion site. The loss of F protein expression was rapid (within two passes) when hCMV was combined with codon-optimized F protein as compared to a combination of hCMV with wild-type F-sequence (loss of F protein expression within 6 passages). Taken together, the data shows that human CMV is not an ideal promoter for the generation of stable HVT recombinants expressing NDV-F protein. Surprisingly, this example shows that SV40 promoter and HVT endogenous promoter (US10 promoter) generated stable HVT recombinants expressing NDV-F protein.

Example 5

Construction of Recombinant vSB1-009 Expressing NDV-F

The aim of the study is to construct a recombinant SB-1 viral vector vSB1-009 in which an expression cassette containing SV40 promoter and Newcastle disease virus fusion protein (NDV-F) is inserted to replace UL44 coding sequence (gC) of SB-1.

A donor plasmid pSB1 44 cds SV FCAopt was constructed containing UL44 flanking arms of SB1 virus, SV40 promoter and NDV F codon optimized gene sequence (SEQ ID NO:5, coding for SEQ ID NO:6).

Generation of Recombinant Virus

A standard homologous recombination procedure was followed by co-electroporation of secondary CEF cells using donor plasmid pSB1 44 cds SV FCAopt and viral DNA isolated from SB-1 virus infected CEFs. Essentially the procedure described in example 1 for vHVT114 was followed to generate, plaque purify and characterize recombinants by immunofluorescence.

After two rounds of plaque purification, pure recombinant virus (vSB1-009) was isolated and the purity of vSB1-009 was tested by IFA and PCR to validate the appropriate insertion as well as no remnant parental virus.

PCR Analysis

Viral DNA was extracted from vSB1-009 pre-master seed virus (pre-MSV) stock by QIA DNeasy Blood & Tissue Kit (Qiagen cat #69506). PCR primers were designed to identify the presence of the NDV F optimized, the NDV F wild type, the SV40 promoter, the mCMV promoter, the UL44 flanking arms of SB-1 virus and HVT virus. PCR amplifications were performed using approximately 200 ng of DNA template along with the primer pairs.

PCR amplification with various primers confirmed that the vSB1-009 has the expected amplification patterns and amplicons.

Expression Analysis

Indirect immunofluorescent assay (IFA) was performed on the vSB1-009 pre-MSV stock to examine the expression of NDV F gene and SB-1 virus antigen. The CEFs that were inoculated with vSB1-009 were fixed with ice-cold 95% acetone for three minutes at room temperature and air-dried for 10 min. The plates were washed with PBS, then two primary antibodies, chicken anti-Newcastle Disease Virus sera (Charles Rivers Laboratories cat #10100641, lot #C0117A) at 1:500 dilution and Y5.9 monoclonal antibody against SB-1 virus (Merial Select, Gainesville, Ga.) at 1:3000 dilution were added and the plates were incubated for 45 min at 37° C. After three washes with PBS, two secondary antibodies, goat anti-chicken IgG-fluorescein (KPL cat #.02-24-06, lot #110020) at 1:500 dilution and donkey anti-mouse IgG-Alexa Fluor 568 (Molecular Probe #A10037, lot #989784) at 1:250 dilution were added. The plates were incubated at 37° C. for 45 min and followed by three washes with PBS. The wells were screened for IFA positive plaques with a fluorescent microscope using fluorescein isothiocyanate (FITC) and tetramethylrhodamine isothiocyanate (TRITC)-filters of Nikon Eclipse Ti inverted microscope. Similarly, reactivity of vSB1-009 with NDV F Mab was examined by Dual IFA using anti-MDV serum (Charles River Laboratories, cat #10100628, lot #D0111) (1/300 dilution) and anti-NDV F monoclonal antibody (1/300 dilution) as primary antibody. The goat anti-chicken IgG-fluorescein (KPL cat #.02-24-06, lot #110020) (1:500 dilution) and donkey anti-mouse IgG-Alexa Fluor 568 (Molecular Probe #A10037, lot #989784) (1:250 dilution) were used as secondary antibodies. The wells were observed to identify the IFA positive plaques with a fluorescent microscope using FITC- and TRITC-filters of Nikon Eclipse Ti inverted microscope.

IFA results indicate that vSB1-009 expresses the NDV F protein in virus-infected CEF. Over 500 vSB1-009 plaques were counted for NDV F protein expression as well as SB-1 virus specific protein expression with dual IFA. The expression of NDV F protein completely matched with SB-1 virus antigen expression in each virus plaque (Table 7).

TABLE 7

Dual IFA of vSB1-009

| Virus | Dual IFA plate#1 (total 189 plaques) | | Dual IFA plate#2 (total 361 plaques) | |
|---|---|---|---|---|
| | Anti-NDV serum positive plaques | Anti-SB-1 MAb positive plaques | Anti-NDV serum positive plaques | Anti-SB-1 MAb positive plaques |
| vSB1-009 pre-MSV | 189 | 189 | 361 | 361 |

NDV F Mab reactivity was confirmed by Dual IFA. Over 200 vSB1-009 plaques were examined for NDV F Mab reactivity as well as anti-MDV serum reactivity. The reactivity with NDV F Mab completely matched with anti-MDV serum reactivity in each virus plaque (Table 8).

TABLE 8

Reactivity of vSB1-009 with anti-NDV F Mab

| Virus | Dual IFA (total 254 plaques) | |
|---|---|---|
| | Anti-MDV serum positive plaques | Anti-NDV F MAb positive plaques |
| vSB1-009 pre-MSV | 254 | 254 |

Southern Blot Analysis

Total genomic DNA was extracted from vSB1-009 pre-MSV stock infected CEFs. The genomic DNA of vSB1-009, SB-1 virus (negative control), pSB1 44 cds SV FCA opt donor plasmid were digested at 37° C. with EcoRI, NcoI, and KpnI restriction endonucleases separately. The restriction fragments were separated by a 0.8% agarose gel electrophoresis and transferred onto a positively charged Nylon membrane. After transfer, the membrane was treated with 0.4M NaOH and then neutralized with 2×SSC-HCl buffer. The membrane was then air dried and UV crosslinked.

Following the North2South Chemiluminescent Hybridization and Detection Kit (Thermo Scientific cat #89880) manufacturers' instructions, the membrane was pre-hybridized for 1 hr and then hybridized with the probe at 55° C. for overnight. For hybridization, two probes were used; 1) the SbfI fragment of pSB1 44 cds SV FCA opt as NDV F cassette probe, 2) the SmaI-EcoRI fragment of pUC57 SB1 44 arm (GenScript) as recombination arm probe. After the overnight hybridization, several stringency washes were conducted until the membrane was placed in blocking buffer with the addition of Streptavidin-HRP. After rinsing the membrane of any unbound Streptavidin-HRP, the substrate solution of Luminal and peroxide were added. The membrane was then exposed to X-ray film and the film was developed.

The Southern blot results were as expected based on Vector NTI map analysis. The NDV F cassette (SV40 promoter, NDV-F CA02 codon optimized gene) replaced the UL44 coding sequences of SB-1 virus.

Genomic Analysis

The genomic DNA of vSB1-009 pre-MSV stock was conducted by nucleotide sequence determination of the region of recombination arm as well as inserted gene cassette. Primers were designed and used to amplify the entire NDV-F gene cassette including the recombination arms.

The vSB1-009 sequence (donor plasmid pSB1 44 cds SV FCAopt) containing the recombinant arms, SV40 promoter and NDV F codon-optimized gene was confirmed to be correct as shown in SEQ ID NO:19.

Western Blot Analysis

The CEF monolayer was infected with vSB1-009 pre-MSV at MOI~0.1. After a 5-day incubation, the CEFs were pelleted and washed with PBS followed by lysis with IP Lysis/Wash buffer of Pierce Classic IP Kit (Thermo Scientific cat #26146) according to the manufacturers' protocols. The lysate was pre-cleared and incubated with 100 ul of anti-NDV F monoclonal antibody to make the immune complex. The immune complex was captured by Protein A/G Plus Agarose and after removing of the un-bounded immune complex by washing steps, the 50 ul of sample buffer was used to elute under non-reducing conditions. The uninfected CEFs were included as a control. The 20 ul of eluted samples were separated in 10% Bis-Tris gels by electrophoresis. After the electrophoresis, the separated proteins in a gel were transferred onto PVDF membrane. The Protein Detection TMB Western Blot Kit (KPL cat #54-11-50) was used to detect the NDV antigens onto PVDF membrane with chicken anti-NDV serum (Charles River Laboratories Laboratories cat #10100641, lot #C0117A), and goat anti-chicken IgG-peroxidase conjugate (KPL cat #14-24-06) following the manufacturers' protocols.

The NDV F protein expression of vSB1-009 was confirmed by two-step immunodetection. First, the expressed NDV F proteins from vSB1-009 infected CEF lysate were captured by the immunoprecipitation using anti-NDV F monoclonal antibody 001C3. Subsequently Western blot analysis using anti-NDV polyclonal serum (Charles River Laboratories cat #10100641, lot #C0117A) was applied to detect the NDV F protein in the captured samples (NDV F protein-monoclonal antibody complex) (FIG. 9). An approximately 55 kDa protein in vSB1-007 pre-MSV lysates was detected by anti-NDV serum that corresponding the expected size of NDV F1 fusion protein (FIG. 9).

Generation and characterization of HVT recombinants vSB1-004, vSB1-006, vSB1-007 and vSB1-008 were essentially done in the same way as for vSB1-009 described in this example. Table 9 shows the features unique to each construct around the expression cassettes, including the respective sequences. The generation and characterization of recombinant SB1 viral vectors were also described in U.S. patent application Ser. No. 13/689,572 filed on Nov. 29, 2012 (Merial, Inc.), which is incorporated herein by reference in its entirety.

TABLE 9

Characteristics of the expression cassettes of SB1 recombinants

| Name | Parental virus | Promoter | F gene | Locus |
|---|---|---|---|---|
| vSB1-009 | SB1 | SV40 | Opt-CA02 | UL44 (gC) |
| vSB1-004 | SB1 | mCMV IE | Wt-VIId | US10 |
| vSB1-006 | SB1 | SV40 | Opt-VIId | UL55/LORF5 |
| vSB1-007 | SB1 | SV40 | Opt-VIId | UL44 (gC) |
| vSB1-008 | SB1 | SV40 | Opt-CA02 | UL55/LORF5 |

Example 6

Efficacy of vHVT110, vHVT111, vHVT114 and vSB1-004 Expressing the NDV F Gene Against Challenges with NDV Chimalhuacan and Malaysian (MAL04-01) Strains at 14 Days of Age in SPF Chickens The aim of the study was to assess the efficacy of 3 HVT recombinant constructs (vHVT110, vHVT111 and vHVT114) and 1 SB1 recombinant construct (vSB1-004) expressing the NDV F gene against Newcastle disease challenges (Chimalhuacan and Malaysian virus strains) performed at 14 days of age in SPF chickens.

The characteristics of these 5 vaccine candidates are described in Table 10 below.

TABLE 10

Characteristics of the vectors used in the challenge study

| Name | Parental virus | Promoter | F gene | Poly-A | Locus |
|---|---|---|---|---|---|
| vHVT110 | HVT | mCMV IE | Wt-VIId | SV40 | IG1 |
| vHVT111 | HVT | SV40 | Wt-VIId | SV40 | IG1 |
| vHVT114 | HVT | SV40 | Opt-VIId | SV40 | IG1 |
| vSB1-004 | SB-1 | mCMV IE | Wt-VIId | SV40 | US10 |

On D0, 100 one-day-old SPF chickens were randomly allocated into 10 groups of 10 birds. The birds were injected by subcutaneous injection in the neck at D0 with 0.2 mL of recombinant vaccines containing a target dose of 2000 pfu as described in Table 11 below. It should be mentioned that the titer of vSB1-004 (31600 pfu) administered to birds of groups 6 was well above the target. The birds were challenged by the intramuscular route on D14 with velogenic ND Malaysia (genotype VIId) strain (sub-groups "a") or with virulent ND Chimalhuacan (genotype V) strain (sub-groups "b").

TABLE 11

Challenge study with vHVT110, vHVT111, vHVT114 and vSB1-004

| Group | Vaccine at day-old (D0) | NDV serology at D14* | % protection against mortality/morbidity after Newcastle challenge at 14 days of age (D14) Malaysian strain | Chimalhuacan strain |
|---|---|---|---|---|
| G1a | — | 0/10 | 0%/0% | — |
| G1b | — | — | — | 0%/0% |
| G2a | vHVT110 | 7/10 | 100%/89% | — |
| G2b | vVHT110 | — | — | 100%/70% |
| G3a | vHVT111 | 2/10 | 30%/20% | — |
| G3b | vHVT111 | — | — | 67%/11% |

TABLE 11-continued

Challenge study with vHVT110, vHVT111, vHVT114 and vSB1-004

| Group | Vaccine at day-old (D0) | NDV serology at D14* | % protection against mortality/morbidity after Newcastle challenge at 14 days of age (D14) Malaysian strain | Chimalhuacan strain |
|---|---|---|---|---|
| G4a | vHVT114 | 9/10 | 100%/100% | — |
| G4b | vHVT114 | — | — | 89%/89% |
| G5a | vSB1-004 | 3/10 | 70%/50% | — |
| G5b | vSB1-004 | — | — | 40%/30% |

*Number of birds positive by NDV HI test/total tested

Each group was monitored before and after challenge. Clinical signs after challenge were scored daily as follows: healthy/with specific symptoms (ruffled feathers, prostration, torticollis, tremor)/dead. On D14, serum samples were taken in each group for serology (Newcastle Disease virus haemagglutination inhibition (HI) test).

As expected, the unvaccinated animals (G1a and G1b) displayed no NDV antibodies on D14. A low titer seroconversion (mean HI titer<0.6 log 10) was obtained in each vaccinated group (sub-groups "a" and "b" of G2 to G5) confirming the vaccine takes. The number of positive birds/total tested was group-dependent and was the highest (90%) in vHVT114 vaccinated birds (see Table above).

Percentages of protection against mortality and morbidity are reported in the table above. Full susceptibility was observed in the control groups G1a and G1b thus validating the high severity of both challenges. Lowest protection levels were observed in the groups vaccinated with vHVT111 or vSB1-004. Highest protection rates against morbidity and mortality were obtained in the groups vaccinated with vHVT110 or vHVT114 whatever the challenge strain used (homologous strain i.e. Malaysian genotype VIId or heterologous strain i.e. Chimalhuacan genotype V). There was a correlation between the % of birds positive by HI test before challenge and the % protection.

The difference of protection obtained between vHVT110 and vHVT111 clearly illustrates the importance of the promoter, the mCMV IE promoter being more potent than the SV40 promoter for the transcription of the wild type (wt) genotype VIId F gene. The difference of protection obtained between vHVT111 and vHVT114 illustrates the importance of the nucleotide sequence of the F gene, the optimized sequence being more potent than the wild type (or native) sequence.

In conclusion, the results of this study showed the importance of the promoter and the nucleotide sequence of the F gene in the ND protection induced by Marek's disease vector vaccines. An optimal combination of these factors need to be found to reach the best efficacy performances as for vHVT114.

Example 7

Efficacy of vHVT114, vHVT116, vHVT301, vHVT302 and vHVT303 Expressing the NDV F Gene Against Challenges with NDV Texas GB Strain at 14 Days of Age in SPF Chickens The aim of the study was to assess the efficacy of 2 single HVT recombinant constructs (vHVT114 and vHVT116) expressing the NDV F gene and 3 double HVT recombinant constructs (vHVT-301, vHVT302 and vHVT303) expressing both NDV F and IBDV VP2 genes against Newcastle disease challenge (Texas GB strain, genotype II) performed at 14 days of age in SPF chickens.

The characteristics of these 4 vaccine candidates are described in Table 12 below.

TABLE 12

Characteristics of the vectors used in the challenge study

| Name | Parental virus | Promoter | F gene | Poly-A | Locus |
|------|----------------|----------|--------|--------|-------|
| vHVT114 | HVT | SV40 | Opt-VIId | SV40 | IG1 |
| vHVT116 | HVT | SV40 | Opt-V | SV40 | IG1 |
| vHVT301 | vHVT13* | SV40 | Wt-VIId | SV40 | IG2 |
| vHVT302 | vHVT13 | US10 | Opt-VIId | US10 | US10 |
| vHVT303 | vHVT13 | US10 | Opt-V | US10 | US10 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 120 one-day-old SPF chickens were randomly allocated into 6 groups of 20 birds. The birds were injected by subcutaneous injection in the neck at D0 with 0.2 mL of recombinant vaccines containing a target dose of 1000 pfu as described in Table 13 below. The birds were challenged by the intramuscular route on D14 with 4.5 log 10 EID50 velogenic ND Texas GB (genotype II) strain.

TABLE 13

Results of efficacy

| Group | Vaccine at day-old (D0) | % clinical protection (number infected/total) after Newcastle challenge at 14 days of age (D14) |
|-------|--------------------------|-------------------------------------------------------------------------------------------------|
| G1 | — | 0% (20/20) |
| G2 | vHVT114 | 80% (4/20) |
| G3 | vHVT116 | 70% (6/20) |
| G4 | vHVT301 | 15% (17/20) |
| G5 | vHVT302 | 52.6% (9/19)* |
| G6 | vHVT303 | 15% (17/20) |

*1 bird died before challenge

Each group was monitored before and after challenge. NDV clinical signs and mortality were recorded after challenge.

Percentages of clinical protection are reported in the table above. Full susceptibility was observed in the non-vaccinated challenged control group G1 thus validating the high severity of both challenges. Partial protection was observed for the 5 vaccine candidates, the best performances being obtained with vHVT114 and vHVT116. Among the double HVT recombinants, the vHVT302 was the most protective. It performed better than vHVT303 suggesting that the optimized genotype VIId NDV F gene may be better cross-protective against genotype II challenge than the optimized genotype V NDV F gene. A similar tendency was observed with single HVT, the vHVT114 (VIId gene) performing slightly better than vHVT116 (V gene) but the difference was less pronounced. These results indicated that both genotypes VIId and V NDV F genes inserted in the HVT vector provide cross-protection against an heterologous genotype II NDV challenge; the VIId gene may potentially be more cross-protective. The vHVT302 induced a better ND protection than vHVT301 confirming the importance of the promoter, poly-A and locus of insertion. In conclusion, the results of this study showed the very good early ND protection induced by tested Marek's disease vector vaccines, especially for the tested single HVT-ND.

Example 8

Efficacy of vHVT114, vHVT116, vSB1-007, vSB1-008 (Alone or with vHVT13) and vHVT 304 Against Challenges with NDV ZJ1 (Genotype VIId) and California/02 (Genotype V) at 21 Days of age in SPF Chickens The aim of the study was to assess the efficacy of 2 single HVT recombinant constructs (vHVT114 and vHVT116), 2 SB1 recombinant constructs (vSB1-007 & vSB1-008) expressing the NDV F gene and a double HVT recombinant (vHVT304) against Newcastle disease challenge with NDV ZJ1 (genotype VIId) and California/02 (genotype V) performed at 21 days of age in SPF chickens.

The characteristics of these 5 vaccine candidates are described in Table 14 below.

TABLE 14

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vHVT116 | HVT | SV40 | Opt-V | SV40 | IG1 |
| vSB1-007 | SB-1 | SV40 | Opt-VIId | gC | UL44 (gC) |
| vSB1-008 | SB-1 | SV40 | Opt-V | SV40 | IG1 |
| vHVT304 | vHVT13* | SV40 | Opt-VIId | Synth | IG2 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 158 one-day-old SPF chickens were randomly allocated into 6 groups of 24 birds (vaccinated) and 1 group of 12 birds (non-vaccinated controls). The birds were injected by subcutaneous injection in the neck at D0 with 0.2 mL of recombinant vaccines containing a target dose of 1000 pfu as described in Table 15 below. The birds were then separated into two sub-groups, each sub-group being challenged by the intramuscular route on D21 with 5 log 10 EID50 of either NDV ZJ1 (genotype VIId) or California/02 (genotype V) velogenic strain.

TABLE 15

Results of efficacy

| Group | Vaccine at day-old (D0) | % clinical protection | |
|---|---|---|---|
| | | CA/02 (genotype V) | ZJ1 (genotype VIId) |
| G1 | — | 0% | 0% |
| G2 | vHVT114 | 100% | 100% |
| G3 | vHVT116 | 100% | 90% |
| G4 | vSB1-007 | 92% | 100% |
| G5 | vSB1-008 | 100% | 100% |
| G6 | vSB1-008 + vHVT13 | 100% | 83% |
| G7 | vHVT304 | 92% | 75% |

Each group was monitored before and after challenge. Technical problems observed with isolators reduced the number of birds in group 2 (vHVT114: from 24 to 14) and in group 3 (vHVT116: from 24 to 20). NDV clinical signs were recorded after challenge. Serum was collected from blood samples taken from birds of groups 2 and 7 before challenge (D21) for NDV serology by HI test using each challenge strains as antigen.

Mean serologic HI titers in G2 and G7 before challenge are shown in FIG. 10. HI titers were higher with the ZJ1 antigen in both groups. The HI titers induced by vHVT114 were higher than those induced by vHVT304.

Percentages of protection against mortality and morbidity are reported in the table above. Full susceptibility was observed in the non-vaccinated challenged control group G1 thus validating the high severity of both challenges. All vaccines induced high levels (≥75%) of protection against both challenges. Full clinical protection against both challenges was induced by vHVT114 and vSB1-008. Following a similar tendency as the HI titers, the ND protection induced by vHVT304 was slightly lower than that induced by vHVT114.

The shedding was evaluated after challenge by real time RT-PCR in oral and cloacal swabs taken 2 and 4 days post-challenge. Percentage of positive (Ct<40) birds are shown for both challenges in FIGS. 11A and 11B. Note that all 6 birds were dead at 4 dpch in the control group challenged with the CA/02 isolate and only one bird (out of 6) was still alive at 4 dpch in the control group challenged with ZJ1. Shedding was detected in all control birds. Reduction of the percentage of birds positive for shedding was observed in all vaccinated groups.

In conclusion, the results of this study showed the very good ND protection at 3 weeks of age induced by tested Marek's disease vector vaccines.

Example 9

Efficacy of vHVT114, vSB1-007, vSB1-009, vHVT306 and vHVT307 Vaccines Against Challenges with NDV Texas GB Strain at 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 28 days of age in SPF chickens.

The characteristics of the 5 recombinant vaccine candidates tested in this study are described in Table 16 below.

TABLE 16

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | UL44 (gC) |
| vSB1-009 | SB-1 | SV40 | Opt-V | gC | UL44 (gC) |
| vHVT306 | vHVT13 | SV40 | Opt-VIId | Synth | SORF3-US2 |
| vHVT307 | vHVT13 | SV40 | Opt-V | Synth | SORF3-US2 |

The Marek's disease virus serotype 1 (CVI988 (or Rispens) strain; Gallid herpesvirus 2) and serotype 2 (SB-1 strain; gallid herpesvirus 3) vaccines were used also in combination with recombinant viruses in some of the groups.

On D0, 135 one-day-old SPF chickens were randomly allocated into 9 groups of 15 birds. The birds were injected by subcutaneous injection in the neck at D0 with 0.2 mL containing a target dose of 2000 pfu for recombinant vaccines (vSB1-007, vSB1-009, vHVT13, vHVT306, vHVT307, vHVT114), and 1000 pfu for parental Marek's disease vaccine strains (SB-1 and CVI988). The design of the 9 groups is shown in Table 17 below. The birds were challenged by the intramuscular route on D28 with 4.0 log 10 EID50 velogenic ND Texas GB (genotype II) strain.

TABLE 17

Results of efficacy

| Group | Vaccine at day-old (D0) | % ND protection after Newcastle disease challenge at 28 days of age |
|---|---|---|
| G1 | — | 0% |
| G2 | vSB1-007 + vHVT13 | 80% |
| G3 | vSB1-009 | 100% |
| G4 | vSB1-009 + vHVT13 | 86% |
| G5 | vSB1-009 + vHVT13 + CV1988 | 93% |
| G6 | vHVT306 + SB-1 | 100% |
| G7 | vHVT307 | 100% |
| G8 | vHVT307 + SB-1 | 93% |
| G9 | vHVT114 + vHVT13 + SB-1 | 100% |

Each group was monitored before and after challenge. NDV clinical signs after challenge were recorded.

Percentages of protection against mortality and morbidity are reported in the table above. Full susceptibility was observed in the non-vaccinated challenged control group G1 thus validating the high severity of challenge. Excellent levels of protection were observed in all vaccinated groups. Birds from G3, G6, G7 and G9 were fully protected. This study shows that the vSB1-ND candidates can be co-administered with vHVT13 and CVI988 and still provide a very good ND protection. Similarly, double HVT-IBD+ND are compatible with SB-1 and vHVT-ND (vHVT114) is compatible with vHVT13 and SB-1.

In conclusion, the results of this study showed the lack of interference on ND protection induced by the tested Marek's disease parental and vector vaccines.

Example 10

Efficacy of vHVT114, vHVT307, vSB1-007 and vSB1-009 in Combination with vHVT13 Against Challenges with NDV Chimalhuacan Strain (Genotype V) at D28 in SPF Chickens The aim of the study was to assess the efficacy of 1 HVT recombinant construct (vHVT114) and 2 SB1 recombinant constructs (vSB1-007 and vSB1-009) expressing the NDV F gene in combination with vHVT-IBD (vHVT13), as well as a double HVT vHVT307 expressing both NDV F and IBDV VP2 against Newcastle disease challenge (Chimalhuacan, genotype V) performed at 28 days of age in SPF chickens.

The characteristics of these 4 vaccine candidates are described in Table 18 below.

TABLE 18

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | UL44 (gC) |
| vSB1-009 | SB-1 | SV40 | Opt-V | gC | UL44 (gC) |
| vHVT307 | vHVT13 | SV40 | Opt-V | Synth | SORF3-US2 |

On D0, 45 one-day-old SPF chickens were randomly allocated into 4 groups of 10 birds and 1 group of 5 birds (unvaccinated control group). The birds were injected by subcutaneous injection in the neck at D0 with 0.2 mL or recombinant vaccines containing a target dose of 2000 pfu as described in Table 19 below. The birds were challenged by the intramuscular route on D28 with 5.0 log 10 EID50 velogenic Chimalhuacan (genotype V) strain.

TABLE 19

Results of efficacy

| Group | Vaccine at day-old (D0) | % protection against mortality | % protection against morbidity |
|---|---|---|---|
| G1 | — | 0% | 0% |
| G2 | vHVT114 + vHVT13 | 100% | 100% |
| G3 | vHVT307 | 80% | 80% |
| G4 | vSB1-007 + vHVT13 | 90% | 90% |
| G5 | vSB1-009 + vHVT13 | 90% | 90% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Percentages of protection against mortality and morbidity are reported in the table above. Full susceptibility was observed in the non-vaccinated challenged control group G1 thus validating the high severity of challenge. Very good protection was observed in all 4 vaccinated groups, a full clinical protection being induced by vHVT114+vHVT13. The percentage of positive birds and the mean shedding titer (expressed as log 10 EID50 equivalent per mL) are shown in FIGS. 12A and 12B. Surprisingly, no shedding was detected in G2 indicating a complete (against both clinical signs and shedding) ND protection induced by vHVT114 even if co-administered with vHVT13, in the tested conditions. The shedding levels detected in the other vaccinated groups were low with a slightly higher level detected in G3 (vHVT307) at 5 days post-infection (pi) only.

In conclusion, this example further illustrates the excellent ND protection induced by double HVT-IBD+ND recombinant or a combination of SB1-ND or HVT-ND and HVT-IBD (vHVT13) recombinant viruses. Contrary to the general belief in the field that a second HVT vaccine (regular HVT vaccines or recombinant HVT vaccines) interferes with the immunity to the foreign genes inserted into the first recombinant HVT vaccine, the present invention showed surprising result that vHVT114 in combination with vHVT13 offered excellent protection against NDV and no interference effect was observed.

Example 11

Efficacy of vHVT306, vSB1-008 in Combination with vHVT13 Administered by SC or in ovo Route Against Challenge with NDV Chimalhuacan Strain (Genotype V) at D28 in SPF Chickens The aim of the study was to assess the efficacy of the vHVT306 double HVT expressing both NDV F and IBDV VP2 genes, and the vSB1-008 SB1 recombinant expressing the NDV F gene in combination with vHVT-IBD (vHVT13), administered by the in ovo or by the subcutaneous route against Newcastle disease challenge (Chimalhuacan, genotype V) performed at 28 days of age in SPF chickens.

The characteristics of these 2 ND vaccine candidates are reported in the table 14 (vSB1-008) and in table 16 (vHVT306).

The design of the groups is shown on Table 20. Sixty SPF embryonated eggs (after approximately 18 days and 18 hours of incubation; D-3) were used for the in ovo administration (20 per group for G1, G2 and G3). Fifty microliters of vaccine containing 2000 PFU were administered by the in ovo route using the IntelliLab System device from AviTech LLC (Salisbury, Md., USA). Hatchability and survival were recorded after in ovo administration. On D0, 20 one-day-old SPF chickens were randomly allocated into 2 groups of 10 birds (G4 and G5). The birds were injected by subcutaneous (SC) injection in the neck at D0 with 0.2 mL or recombinant vaccines containing a target dose of 2000 pfu as described in Table 20 below. Ten birds per group were challenged by the intramuscular route on D28 with 5.0 log 10 EID50 velogenic Chimalhuacan (genotype V) strain.

TABLE 20

Study design and results of ND efficacy

| Group | Vaccine at day-old (D0) | Admin. route | % protection against mortality | % protection against morbidity |
|---|---|---|---|---|
| G1 | vHVT13 | In ovo | 0% | 0% |
| G2 | vHVT306 | In ovo | 100% | 100% |
| G3 | vSB1-008 + vHVT13 | In ovo | 78% | 68% |
| G4 | vHVT306 | SC | 100% | 100% |
| G5 | vSB1-008 + vHVT13 | SC | 100% | 70% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Full hatchability and viability were recorded up to D28 (challenge day) for birds of groups G1 and G2. Hatchability in G3 was 85% and one additional bird died after hatching in this group. The lower hatchability of that group may be due to egg incubator problems. Body weights of males and females in G1, G2 and G3 were similar at D1 and at D28.

Percentages of protection against mortality and morbidity are reported in the table 20. Full susceptibility was observed in the non-vaccinated challenged control group G1 thus validating the high severity of challenge. Very good protection was observed in all 4 vaccinated groups, a full clinical protection being induced by vHVT306 administered by both routes.

The percentage of positive birds and the mean shedding titer (expressed as log 10 EID50 equivalent per mL) are shown in Table 21. Absence of detectable or very low shedding was observed in G2 and G4 vaccinated with vHVT306. The shedding levels detected in the groups vaccinated with vSB1-008+vHVT13 were higher especially at 5 days post-infection (pi).

TABLE 21

Results of protection against shedding (percentage of birds with detectable shedding and mean viral load in log10) evaluated at D5 and D7 after NDV challenge

| Group | Vaccine at day-old (D0) | Admin. Route | Percent of positive birds (D5/D7 pi) | Mean viral load* (D5/D7 pi) |
|---|---|---|---|---|
| G2 | vHVT306 | In ovo | 0/0% | 2.7/2.7 |
| G3 | vSB1-008 + vHVT13 | In ovo | 100/38% | 5.2/3.2 |
| G4 | vHVT306 | SC | 20/10% | 3.2/2.9 |
| G5 | vSB1-008 + vHVT13 | SC | 80/50% | 4.6/3.4 |

*Mean quantitative real time PCR value expressed in equivalent log10 EID50; the threshold is set at 2.7 log10.

In conclusion, this example shows excellent ND protection induced by vHVT306 double HVT recombinant administered either by in ovo or by SC routes. The performance of vSB1-008+vHVT13 was slightly lower especially after in ovo administration, but it may be at least partially due to egg incubator problems. Indeed, the in ovo safety testing of another SB1-ND recombinant (vSB1-009) at 1000 or 4000 PFU associated with 6000 PFU of vHVT13 did not show any difference in hatchability and early survival with a group receiving 6000 PFU of vHVT13 only.

Example 12

Efficacy of vHVT304, vHVT306, vSB1-007 and vSB1-008 in Combination with vHVT13 Against Challenge with NDV Chimalhuacan Strain (Genotype V) at D42 in Commercial Broiler Chickens The aim of the study was to assess the efficacy of two double HVT (vHVT304 and vHVT306) expressing both NDV F and IBDV VP2 genes, and two SB1 recombinants (vSB1-007 and vSB1-008) expressing the NDV F gene in combination with vHVT-IBD (vHVT13) against Newcastle disease challenge (Chimalhuacan, genotype V) performed at 42 days of age in commercial broiler chickens.

The characteristics of these 4 ND vaccine candidates are reported in tables 14 and 16. The design of the groups is shown on Table 22. On D0, 55 one-day-old commercial broiler chickens were randomly allocated into 5 groups of 11 birds. The birds were injected by subcutaneous (SC) injection in the neck at D0 with 0.2 mL or recombinant vaccines containing a target dose of 2000 pfu as described in Table 22 below. Ten birds per group were challenged by the intramuscular route on D42 with 5.0 log 10 EID50 velogenic Chimalhuacan (genotype V) strain.

TABLE 22

Study design and results of ND efficacy

| Group | Vaccine at day-old (D0) | % protection against mortality | % protection against morbidity |
|---|---|---|---|
| G1 | vHVT13 | 0% | 0% |
| G2 | vHVT304 | 82% | 82% |
| G3 | vHVT306 | 100% | 100% |
| G4 | vSB1-007 + vHVT13 | 100% | 100% |
| G5 | vSB1-008 + vHVT13 | 91% | 91% |

Each group was monitored before and after challenge. NDV clinical signs were recorded during 14 days after challenge. Oropharyngeal swabs were taken in the vaccinated groups at 5 and 7 days post-challenge to evaluate the viral load by real time RT-PCR.

Percentages of protection against mortality and morbidity are reported in the table 22. Full susceptibility was observed in the non-vaccinated challenged control group G1 thus validating the high severity of challenge. Very good protection was observed in all 4 vaccinated groups, a full clinical protection being induced by vHVT306 and by vSB1-007+vHVT13.

The percentage of positive birds and the mean shedding titer (expressed as log 10 EID50 equivalent per mL) are shown in Table 23. The best reduction of shedding was induced by vHVT306 and vSB1-007+vHVT13, which were also the best candidates for clinical protection.

TABLE 23

Results of protection against shedding (percentage of birds with detectable shedding and mean viral load in log10) evaluated at D5 and D7 after NDV challenge (pi)

| Group | Vaccine at day-old (D0) | Percent of positive birds (D5/D7 pi) | Mean viral load* (D5/D7 pi) |
|---|---|---|---|
| G2 | vHVT304 | 100/100% | 5.4/4.6 |
| G3 | vHVT306 | 40/50% | 3.5/3.7 |
| G4 | vSB1-007 + vHVT13 | 80/70% | 3.8/4.8 |
| G5 | vSB1-008 + vHVT13 | 100/100% | 4.8/4.3 |

*Mean quantitative real time PCR value expressed in equivalent log10 EID50; the threshold is set at 2.7 log10.

The vHVT306 ND protection was found to be better than that of vHVT304. These two double HVT contain the same NDV F expression cassette but inserted in two different loci, the IBDV VP2 one being inserted at the same position. This example therefore illustrates the importance of the locus of insertion in the design of HVT recombinants. The vSB1-007+vHVT13 was better than vSB1-008+vHVT13. The vSB1-007 genomic structure differs from that of vSB1-008 in different aspects: locus of insertion, promoter, poly-adenylation signal and F gene origin. The combination of these foreign sequences and locus of insertion in vSB1-007 were likely responsible for its better ND protection performances.

In summary, this example illustrates the importance of the locus of insertion and other regulatory sequences of the NDV expression cassette in the ND protection induced by HVT and MDV serotype 2 vectors.

Example 13

Efficacy of Double HVT-ND+IBD (vHVT304 and vHVT306) or SB1-ND (vSB1-008) in Combination with vHVT13 Recombinant Vaccines, Against Challenge with a Classical IBDV Isolate on D14 in SPF Chickens The aim of the study was to assess the early IBD efficacy of double HVT recombinants vHVT304 and vHVT306 as well as that of vHVT13 co-administered with a SB1-ND (vSB1-008) recombinant constructs against a virulent infectious bursal disease virus (vIBDV) challenge (Faragher 52/70 strain) performed at 14 days of age in SPF chickens.

The characteristics of the double HVT and SB1 recombinants used in this study are shown in Tables 14 and 16.

On D0, 95 one-day-old SPF chickens were randomly allocated into 9 groups of 10 birds and 1 group of 5 birds (unvaccinated unchallenged control group). The birds were injected by subcutaneous injection in the neck at D0 with 0.2 mL or recombinant vaccines containing a target dose of 300 or 1000 pfu as described in the Table 24 below. On D14, blood sample was collected from 5 birds per group for serological testing with the Kit ProFLOK® plus IBD (Synbiotics Corp). The birds (10 birds per group except for group 7 in which 1 bird died before challenge) were challenged by the eye drop (0.05 mL per bird) on D14 with 2.5 log 10 EID50.

TABLE 24

Study design and results of IBD efficacy

| Group | Vaccine at day-old (dose in PFU) | IBD + ELISA titer at D14[1] | Number Dead/ Sick[2] | % protection[3] | Mean bursal/ body weight ratio[4] |
|---|---|---|---|---|---|
| G1 | vSB1-008 (1000) | 0.2 | 7/10 | 0% | 0.0013 |
| G2 | vHVT13 (300) | 2.7 | 0/0 | 100% | 0.0051 |
| G3 | vHVT13 (1000) | 2.7 | 0/0 | 90% | 0.0049 |
| G4 | vHVT13 + vSB1-008 (300) | 1.9 | 1/1 | 60% | 0.0041 |
| G5 | vHVT13 + vSB1-008 (1000) | 2.4 | 0/0 | 70% | 0.0041 |
| G6 | vHVT304 (300) | 2.9 | 0/0 | 60% | 0.0037 |
| G7 | vHVT304 (1000) | 2.2 | 0/0 | 67% | 0.0047 |
| G8 | vHVT306 (300) | 2.4 | 0/0 | 80% | 0.0033 |
| G9 | vHVT306 (1000) | 2.7 | 0/0 | 40% | 0.0026 |

[1]Mean IBD + ELISA titers expressed in log10 in the serum of 5 birds per group sampled at D14 before challenge;
[2]Birds sick for more than 2 days or still sick on D25 were considered as sick.
[3]Protection against clinical signs and severe bursal lesion (bursal score <3)
4The bursal/body weight ratio of the unvaccinated/unchallenged group was 0.0047.

Each group was monitored before and after challenge. IBDV clinical signs were recorded for 11 days after challenge (from D15 to D25). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 25.

TABLE 25

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008:0587 of EU Pharmacopoeia "Avian Infectious Bursal Disease vaccine (live)

A bird was considered as affected if it died and/or showed notable sign of disease and/or severe lesions of the bursa of Fabricius (i.e., histology score 3).

The mean ELISA IBD+antibody titer expressed in log 10 before challenge is shown in Table 24. Significant titers were detected in all vaccinated groups that were significantly higher than that of the control group G1. The serology titer was not dose-dependent.

Severe clinical signs were observed after challenge in all birds of the control group G1. Seven out of 10 birds of that group died within the 11 days observation period indicating the high severity of challenge. None of the vaccinated birds showed severe clinical signs after challenge except 1 bird of G4 that died. Percentages of protection against severe bursal lesions are shown in the table above. Significant IBD protection was observed in all groups, the best protection being observed in G2 and G3 (vHVT13 alone). The co-administration of vSB1-008+vHVT13 and the double vHVT304 and vHVT306 constructs induced similar levels of IBD protection. The protection was not dose-dependent. The mean bursal/body weight ratios are also shown in Table 24. Ratios in all vaccinated groups were higher than those of the challenged control group.

In conclusion, these data indicate that both the combination of a SB1-ND vector with a single HVT-IBD or double HVT expressing both NDV-F and IBDV-VP2 induce IBD antibodies and early IBD protection in a severe IBDV challenge model.

Example 14

Efficacy of Single HVT-ND (vHVT114) or SB1-ND (vSB1-007 and vSB1-009) in Combination with vHVT13 Recombinant Vaccines, Against Challenge with a Very Virulent IBDV Isolate on D23 in Commercial Broiler Chickens The aim of the study was to assess the IBD efficacy of vHVT13 co-administered with an HVT-ND (vHVT114) or SB1-ND (vSB1-007 and vSB1-009) recombinant constructs against a very virulent infectious bursal disease virus (vvIBDV) challenge (91-168/980702) performed at 23 days of age in commercial broiler chickens.

The characteristics of these 4 vaccine candidates are described in Tables 14 and 16. On D0, 90 one-day-old broiler chickens were randomly allocated into 7 groups of 12 birds and 1 group of 6 birds (unvaccinated unchallenged control group). The birds were injected by subcutaneous injection in the neck at D0 with 0.2 mL or recombinant vaccines containing a target dose of 3000 pfu as described in the Table 26. On D14, blood sample was collected from 5 birds per group for serological testing with the Kit Pro-FLOK® plus IBD (Synbiotics Corp). The serum of 10 extra one-day-old broiler chickens was tested at D0 with the same kit to evaluate the level of IBDV maternal antibody. The birds (10 birds per group) were challenged by the eye drop (0.05 mL per bird) on D23 with 4.3 log 10 EID50.

Each group was monitored before and after challenge. IBDV clinical signs were recorded for 11 days after challenge (from D23 to D33). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 25.

A bird was considered as affected if it died and/or showed notable sign of disease and/or severe lesions of the bursa of Fabricius (i.e., histology score 3).

TABLE 26

Study design and serology results

| Group | Vaccine at day-old (D0) | IBD + ELISA titer at D23[1] | Mean bursal/body weight ratio[2] |
|---|---|---|---|
| G1 | — | 3.9 | 0.0007 |
| G2 | vHVT13 | 4.0 | 0.0015 |
| G3 | vHVT114 + vHVT13 | 4.1 | 0.0015 |
| G4 | vSB1-007 + vHVT13 | 3.8 | 0.0018 |
| G5 | vSB1-009 + vHVT13 | 4.0 | 0.0019 |

[1]Mean IBD + ELISA titers expressed in log10 in the serum of 5 birds per group sampled at D23 before challenge;
[2]The bursal/body weight ratio of the unvaccinated/unchallenged group was 0.0047

The mean ELISA IBD+serological titer at D0 was 4.36±0.01 log 10 indicating a very high level of IBD maternal antibody. At D23, the mean ELISA titer was still high (3.9) in the control G1. ELISA mean titers in the vaccinated groups were not different from the control group.

Neither morbidity nor mortality was observed in any of the groups after challenge. Percentages of protection against severe bursal lesions are shown in the table 24 above. The result showed that co-administration of vHVT114, vSB1-007 or vSB1-009 did not interfere with vHVT13-induced IBD protection indicating a lack of interference. Similarly, the mean bursal/body weight ratios of the vaccinated groups were similar and clearly higher than that of the control group, indicating IBD protection and no difference between the vaccination regimens.

In conclusion, the data indicate the compatibility between vHVT114, vSB1-007 or vSB1-009 and vHVT13 for IBD protection.

Example 15

Efficacy of Recombinant HVT and SB1 Vectors Against Marek's Disease

Efficacy is demonstrated for the HVT vectored recombinants and the SB-1 vectored recombinants either alone or in combination. The challenge strains include a virulent Marek's disease (vMD) challenge such as GA22, a very virulent Marek's disease (vvMD) challenge such as RB1B and/or a very virulent plus Marek's disease (vv+MD) challenge such as the T. King virus. One-day-old chickens are inoculated subcutaneously or 18-19-day-old embryonated eggs are inoculated with a 0.2 ml dose or 0.05 ml dose, respectively, of the test viruses. At five days of age the vaccinated chickens and naïve controls are challenged with the relevant Marek's challenge virus (v, vv, or vv+MDV). The challenged birds are observed until seven weeks of age. All birds are terminated and necropsied to observe for grossly visible lesions associated with Marek's disease.

Having thus described in detail preferred embodiments of the present invention, it is to be understood that the invention defined by the above examples is not to be limited to particular details set forth in the above description as many apparent variations thereof are possible without departing from the spirit or scope of the present invention.

What we claim is:

1. A composition or vaccine comprising one or more recombinant herpesvirus of turkeys (HVT) vectors, wherein at least one HVT vector comprises two or more heterologous polynucleotides coding for and expressing at least one antigen of an avian pathogen, wherein the at least one polynucleotide encodes a Newcastle Disease Virus F (NDV-F) polypeptide and is operably linked to an SV40 promoter, and wherein the polynucleotide is codon-optimized.

2. The composition or vaccine of claim 1, wherein the HVT vector further comprises a heterologous polynucleotide coding for and expressing one or more Infectious Bursal Disease Virus (IBDV) VP2 polypeptides.

3. The composition or vaccine of claim 2, wherein the NDV-F polypeptide has at least 95% sequence identity to the amino acid sequence as set forth in SEQ ID NO:2, 4, 6, 33, 35, or 37.

4. The composition or vaccine of claim 2, wherein the IBDV VP2 polypeptide has at least 95% sequence identity to the amino acid sequence as set forth in SEQ ID NO:8 or 42.

5. The composition or vaccine of claim 2, wherein the HVT vector comprises a heterologous polynucleotide coding for and expressing an Newcastle NDV-F polypeptide having at least 95% sequence identity to the amino acid sequence as set forth in SEQ ID NO:2, 4, 6, 33, 35, or 37 and one or two heterologous polynucleotides coding for and expressing one or two IBDV VP2 polypeptides having at least 95% sequence identity to the amino acid sequence as set forth in SEQ ID NO:8 or 42.

6. The composition or vaccine of claim 2, wherein the polynucleotide encoding the NDV-F polypeptide is operably linked to a polyA signal selected from the group consisting of an SV40 polyA signal, US10 polyA signal, and a synthetic polyA signal.

7. The composition or vaccine of claim 2, wherein the polynucleotides encoding NDV-F and IBDV VP2 are inserted in a locus selected from the group consisting of IG2 (intergenic region 2), US10, SORF3-US2, and IG1 (intergenic region 1) of HVT genome.

8. The composition or vaccine of claim 5, wherein the one or two polynucleotides encoding the IBDV VP2 polypeptide is operably linked to CMV promoter, guinea pig CMV promoter, or a combination thereof.

9. The composition or vaccine of claim 2, wherein HVT vector is selected from the group consisting of an HVT vector comprising an SV40 promoter and a polynucleotide encoding an NDV-F antigen inserted in the IG2 locus of the HVT vector, an HVT vector comprising an US10 promoter and a polynucleotide encoding an NDV-F antigen inserted in the US10 locus of the HVT vector, an HVT vector comprising an SV40 promoter and a polynucleotide encoding an NDV-F antigen inserted in the SORF3-US2 locus of the HVT vector, and an HVT vector comprising an SV40 promoter and a polynucleotide encoding an NDV-F antigen and a Guinea pig CMV promoter and a polynucleotide encoding an IBDV VP2 antigen inserted in the SORF3-US2 locus of the HVT vector.

10. The composition or vaccine of claim 2, wherein the composition or vaccine is a multivalent composition or vaccine further comprising a second recombinant HVT vector comprising a heterologous polynucleotide coding for and expressing IBDV VP2 polypeptide.

11. The composition or vaccine of claim 10, wherein the second recombinant HVT vector is the HVT vector included in VAXXITEK™ HVT+IBD.

12. The composition or vaccine of claim 2 or 10, wherein the composition further comprises one or more recombinant SB1 vectors or the parental SB1 strain.

13. The composition or vaccine of claim 12, wherein the recombinant SB1 vector comprises one or more heterologous polynucleotides coding for and expressing NDV-F polypeptide or IBDV VP2 polypeptide.

14. The composition or vaccine of claim 2 or 10, wherein the composition or vaccine further optionally comprises a pharmaceutically or veterinarily acceptable carrier, excipient, vehicle or adjuvant.

15. A recombinant HVT vector comprising one or more heterologous polynucleotides coding for and expressing at least one antigen of an avian pathogen, wherein the at least one polynucleotide encodes a Newcastle Disease Virus F (NDV-F) polypeptide and is operably linked to an SV40 promoter, and wherein the polynucleotide is codon-optimized.

16. The recombinant HVT vector of claim 15, wherein HVT vector further comprises, one or more Infectious Bursal Disease Virus (IBDV) VP2 polypeptides.

17. The recombinant HVT vector of claim 15, wherein the HVT vector comprises a first heterologous polynucleotide coding for and expressing an Newcastle NDV-F polypeptide having at least 95% sequence identity to the amino acid sequence as set forth in SEQ ID NO:2, 4, 6, 33, 35, or 37 and one or two heterologous polynucleotides coding for and expressing one or two IBDV VP2 polypeptides having at least 95% sequence identity to the amino acid sequence as set forth in SEQ ID NO:8 or 42.

18. The recombinant HVT vector of claim 15, wherein the polynucleotides encoding NDV-F and IBDV VP2 are inserted in a locus selected from the group consisting of IG2 (intergenic region 2), US10, SORF3-US2, and IG1 (intergenic region 1) of HVT genome.

19. The recombinant HVT vector of claim 15, wherein the one or two polynucleotides encoding the IBDV VP2 antigen is operably linked to CMV promoter, guinea pig CMV promoter, or a combination thereof.

20. The recombinant HVT vector of claim 15, wherein the HVT vector is selected from the group consisting of an HVT vector comprising an SV40 promoter and a polynucleotide encoding an NDV-F antigen inserted in the IG2 locus of the HVT vector, an HVT vector comprising an US10 promoter and a polynucleotide encoding an NDV-F antigen inserted in the US10 locus of the HVT vector, an HVT vector comprising an SV40 promoter and a polynucleotide encoding an NDV-F antigen inserted in the SORF3-US2 locus of the HVT vector, and an HVT vector comprising an SV40 promoter and a polynucleotide encoding an NDV-F antigen and a Guinea pig CMV promoter and a polynucleotide encoding an IBDV VP2 antigen inserted in the SORF3-US2 locus of the HVT vector.

21. A method of vaccinating an animal or inducing an immunogenic or protective response in an animal against one or more avian pathogens comprising at least one administration of the composition of claim 1 or vector of claim 15.

22. The method of claim 21, wherein the avian pathogen is selected from the group consisting of Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum, Mycoplasma synoviae, Pasteurella* sp., *Avibacterium* sp., *E. coli* and *Clostridium* sp.

23. The method of claim 21, wherein the animal is avian.

\* \* \* \* \*

SEQUENCE LISTING

<160> NUMBER OF SEQ ID NOS: 47

<210> SEQ ID NO 1
<211> LENGTH: 1665
<212> TYPE: DNA
<213> ORGANISM: artificial sequence
<220> FEATURE:
<223> OTHER INFORMATION: NDV-F VIId codon-optimized DNA sequence

<400> SEQUENCE: 1

```
atgggcagca agcccagcac aagaatccca gcccccctga tgctgatcac ccgcatcatg      60
ctgatcctgg gctgcatcag acccacaagc tccctggatg gacgccccct ggccgctgcc     120
ggcatcgtgg tgaccggcga caaggccgtg aacgtgtaca ccagcagcca gaccggcagc     180
atcatcgtga agctgctgcc caacatgccc agagacaaag aggcctgcgc caaggccccc     240
ctggaagcct acaacagaac cctgaccacc ctgctgaccc cctgggcga cagcatcaga     300 aagatccagg gctccgtgag cacaagcggc ggaggaaagc agggcagact gatcggcgcc     360
gtgatcggca gcgtggccct gggagtggct acagctgccc agattaccgc tgcagccgcc     420
ctgatccagg ccaaccagaa cgccgccaac atcctgagac tgaaagagag cattgccgcc     480
accaacgagg ccgtgcacga agtgaccgac ggcctgagcc agctgtccgt ggccgtgggc     540
aagatgcagc agttcgtgaa cgaccagttc aacaacaccg ccagagagct ggactgcatc     600
aagatcaccc agcaggtggg cgtggagctg aacctgtacc tgaccgagct gaccacagtg     660
ttcggccccc agatcacaag cccagccctg acacagctga ccatccaggc cctgtacaac     720
```

-continued

| | |
|---|---|
| ctggctggcg gcaacatgga ctatctgctg acaaagctgg gaatcggcaa caaccagctg | 780 |
| tccagcctga tcggaagcgg cctgatcacc ggctacccca tcctgtacga cagccagaca | 840 |
| cagctgctgg gcatccaggt gaacctgccc agcgtgggca acctgaacaa catgcgcgcc | 900 |
| acctacctgg aaaccctgag cgtgtccacc accaagggct acgccagcgc cctggtgccc | 960 |
| aaggtggtga cacaggtggg cagcgtgatc gaggaactgg acaccagcta ctgcatcgag | 1020 |
| agcgacctgg acctgtactg caccagaatc gtgaccttcc caatgagccc cggcatctac | 1080 |
| agctgcctga gcggcaacac cagcgcctgc atgtacagca gaccgaagg cgcactgaca | 1140 |
| acacctaca tggccctgaa gggaagcgtg atcgccaact gcaagatcac cacctgcaga | 1200 |
| tgcaccgacc ccccaggcat catcagccag aactacggcg aggccgtgag cctgatcgat | 1260 |
| cgccattcct gtaacgtgct gtccctggac ggcatcacac tgagactgag cggcgagttc | 1320 |
| gatgccacct accagaagaa catcagcatc ctggacagcc aggtgatcgt gaccggcaac | 1380 |
| ctggacatca gcaccgagct gggcaacgtg aataacagca tcagcaacgc cctggacaga | 1440 |
| ctggccgaga gcaacagcaa gctggaaaaa gtgaacgtgc gcctgacatc cacttccgct | 1500 |
| ctgatcacct acatcgtgct gaccgtgatc agcctggtgt tcggcgccct gagcctggtg | 1560 |
| ctggcctgct acctgatgta caagcagaag gcccagcaga aaaccctgct gtggctgggc | 1620 |
| aacaacaccc tggaccagat gagagccacc accagagcct gatga | 1665 |

<210> SEQ ID NO 2
<211> LENGTH: 553
<212> TYPE: PRT
<213> ORGANISM: artificial sequence
<220> FEATURE:
<223> OTHER INFORMATION: NDV-F protein sequence from codon-optimized
      VIId gene

<400> SEQUENCE: 2

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
                20                  25                  30

Asp Gly Arg Pro Leu Ala Ala Ala Gly Ile Val Val Thr Gly Asp Lys
            35                  40                  45

Ala Val Asn Val Tyr Thr Ser Ser Gln Thr Gly Ser Ile Ile Val Lys
        50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190
```

```
Thr Ala Arg Glu Leu Asp Cys Ile Lys Ile Thr Gln Gln Val Gly Val
            195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550

<210> SEQ ID NO 3
<211> LENGTH: 1662
<212> TYPE: DNA
<213> ORGANISM: artificial sequence
<220> FEATURE:
<223> OTHER INFORMATION: NDV-F VIId wildtype DNA sequence

<400> SEQUENCE: 3
```

| | |
|---|---|
| atgggctcca aaccttctac caggatccca gcacctctga tgctgatcac ccggattatg | 60 |
| ctgatattgg gctgtatccg tccgacaagc tctcttgacg gcaggcctct tgcagctgca | 120 |
| ggaattgtag taacaggaga taaggcagtc aatgtataca cttcgtctca gacagggtca | 180 |
| atcatagtca agttgctccc gaatatgccc agggataagg aggcgtgtgc aaaagcccca | 240 |
| ttagaggcat ataacagaac actgactact tgctcactc ctcttggcga ctccatccgc | 300 |
| aagatccaag ggtctgtgtc cacatctgga ggaggcaagc aaggccgcct gataggtgct | 360 |
| gttattggca gtgtagctct tggggttgca acagcggcac agataacagc agctgcggcc | 420 |
| ctaatacaag ccaaccagaa tgccgccaac atcctccggc ttaaggagag cattgctgca | 480 |
| accaatgaag ctgtgcatga agtcaccgac ggattatcac aactatcagt ggcagttggg | 540 |
| aagatgcagc agtttgtcaa tgaccagttt aataatacgg cgcgagaatt ggactgtata | 600 |
| aaaatcacac aacaggttgg tgtagaactc aacctatacc taactgaatt gactacagta | 660 |
| ttcgggccac agatcacctc ccctgcatta actcagctga ccatccaggc actttataat | 720 |
| ttagctggtg gcaatatgga ttacttatta actaagttag gtagggaa caatcaactc | 780 |
| agctcgttaa ttggtagcgg cctgatcact ggttaccta tactgtatga ctcacagact | 840 |
| caactcttgg gcatacaagt gaatttaccc tcagtcggga acttaaataa tatgcgtgcc | 900 |
| acctatttgg agaccttatc tgtaagtaca accaaaggat atgcctcagc acttgtcccg | 960 |
| aaagtagtga cacaagtcgg ttccgtgata gaagagcttg acacctcata ctgtatagag | 1020 |
| tccgatctgg atttatattg tactagaata gtgacattcc ccatgtcccc aggtatttat | 1080 |
| tcctgtttga gcggcaacac atcagcttgc atgtattcaa agactgaagg cgcactcact | 1140 |
| acgccgtata tggccttaa aggctcagtt attgccaatt gtaaaataac aacatgtaga | 1200 |
| tgtacagacc ctcctggtat catatcgcaa aattatggag aagctgtatc cctgatagat | 1260 |
| agacattcgt gcaatgtctt atcattagac gggataactc taaggctcag tggggaattt | 1320 |
| gatgcaactt atcaaaagaa catctcaata ctagattctc aagtcatcgt gacaggcaat | 1380 |
| cttgatatat caactgaact tggaaacgtc aacaattcaa tcagcaatgc cttggataggg | 1440 |
| ttggcagaaa gcaacagcaa gctagaaaaa gtcaatgtca gactaaccag cacatctgct | 1500 |
| ctcattacct atattgttct aactgtcatt tctctagttt tcggtgcact tagtctggtg | 1560 |
| ttagcgtgtt acctgatgta caaacagaag gcacaacaaa agaccttgct atggcttggg | 1620 |
| aataataccc tcgatcagat gagagccact acaagagcat ga | 1662 |

<210> SEQ ID NO 4
<211> LENGTH: 553
<212> TYPE: PRT
<213> ORGANISM: artificial sequence
<220> FEATURE:
<223> OTHER INFORMATION: NDV-F protein from wildtype VIId DNA sequence

<400> SEQUENCE: 4

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
```

```
                65                  70                  75                  80
Leu Glu Ala Tyr Asn Arg Thr Leu Thr Thr Leu Leu Thr Pro Leu Gly
                    85                  90                  95

Asp Ser Ile Arg Lys Ile Gln Gly Ser Val Ser Thr Gly Gly
                100                 105                 110

Lys Gln Gly Arg Leu Ile Gly Ala Val Ile Gly Ser Val Ala Leu Gly
            115                 120                 125

Val Ala Thr Ala Ala Gln Ile Thr Ala Ala Ala Leu Ile Gln Ala
        130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                485                 490                 495
```

```
Ser Thr Ser Ala Leu Ile Thr Tyr Ile Val Leu Thr Val Ile Ser Leu
            500                 505                 510

Val Phe Gly Ala Leu Ser Leu Val Leu Ala Cys Tyr Leu Met Tyr Lys
            515                 520                 525

Gln Lys Ala Gln Gln Lys Thr Leu Leu Trp Leu Gly Asn Asn Thr Leu
            530                 535                 540

Asp Gln Met Arg Ala Thr Thr Arg Ala
545                 550
```

<210> SEQ ID NO 5
<211> LENGTH: 1665
<212> TYPE: DNA
<213> ORGANISM: artificial sequence
<220> FEATURE:
<223> OTHER INFORMATION: NDV-F Ca02 codon-optimized DNA sequence

<400> SEQUENCE: 5

```
atgggcagca agcccagcac ctggatcagc gtgaccctga tgctgatcac cagaaccatg      60
ctgatcctga gctgcatctg ccccacaagc agcctggacg cagacccct ggccgctgcc     120
ggcatcgtgg tgaccggcga caaggccgtg aacatctaca ccagcagcca gaccggcagc     180
atcatcatca agctgctgcc aacatgccc aaggacaaag aggcctgcgc caaggccccc     240
ctggaagcct acaacagaac cctgaccacc tgctgacccc cctgggcga cagcatcaga     300
agaatccagg cagcgccac acaagcggc ggaggaaagc agggcagact ggtgggcgct     360
atcatcggga gcgtggccct gggcgtggcc acagctgccc agattaccgc tgcagccgcc     420
ctgattcagg ccaatcagaa cgccgccaac atcctgagac tgaaagagag cattgccgcc     480
accaacgacg ccgtgcacga agtgacaaac ggactgtccc agctggctgt cgctgtcggc     540
aagatgcagc agttcgtgaa caaccagttc aacaacaccg ccagagagct ggactgcatc     600
aagatcgccc agcaggtggg cgtggagctg aacctgtacc tgaccgagct gaccacagtg     660
ttcggccccc agatcacaag ccccgctctg acccagctga caatccaggc cctgtacaac     720
ctggctggcg gcaacatgga ctatctgctg actaagctgg gagtgggcaa caaccagctg     780
tccagcctga tcgggtccgg gctgatcaca ggcaacccca tcctgtacga cagccagaca     840
cagctgctgg gcatccagat caacctgcca tccgtgggaa gcctgaacaa catgagagcc     900
acctacctgg aaaccctgag cgtgtccacc accaagggct cgccagcgc cctggtgccc     960
aaggtggtga cacaggtggg cagcgtgatc gaggaactgg acaccagcta ctgcatcgag    1020
agcgacatcg acctgtactg caccagagtg gtgaccttcc aatgagccc cggcatctac    1080
agctgcctga cggcaacac cagcgcctgc atgtacagca gaccgaagg agcactgaca    1140
acaccctaca tggccctgaa gggaagcgtg atcgccaact gcaagatgac cacctgcaga    1200
tgcgccgacc ccccaggcat catcagccag aactacggcg aggccgtgag cctgatcgac    1260
aaacattcct gtagcgtgct gtccctggat ggcatcacac tgagactgag cggcgagttc    1320
gacgccacct accagaagaa catcagcatc ctggacagcc aggtgatcgt gaccggcaac    1380
ctggacatca gcaccgagct gggcaacgtg aacaacagca tcagcagcac cctggacaag    1440
ctggccgagt ccaacaacaa gctgaacaaa gtgaacgtga acctgaccag cacaagcgcc    1500
ctgatcacct acatcgtgct ggccatcgtg tccctggcct tcggcgtgat cagcctggtg    1560
ctggcctgct acctgatgta caagcagaga gcccagcaga aaccctgct gtggctgggc    1620
aataacaccc tggaccagat gagggccacc accagaacct gatga              1665
```

<210> SEQ ID NO 6
<211> LENGTH: 553
<212> TYPE: PRT
<213> ORGANISM: artificial sequence
<220> FEATURE:
<223> OTHER INFORMATION: NDV-F protein sequence from codon-optimized CA02 gene

<400> SEQUENCE: 6

```
Met Gly Ser Lys Pro Ser Thr Trp Ile

```
Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
        515                 520                 525

Gln Arg Ala Gln Gln Lys Thr Leu Leu Trp Leu Gly Asn Asn Thr Leu
    530                 535                 540

Asp Gln Met Arg Ala Thr Thr Arg Thr
545                 550

<210> SEQ ID NO 7
<211> LENGTH: 1362
<212> TYPE: DNA
<213> ORGANISM: artificial sequence
<220> FEATURE:
<223> OTHER INFORMATION: IBDV DNA sequence encoding VP2

<400> SEQUENCE: 7
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtctttttc     180
cctggattcc ctggctcaat gtgggtgct cactacacac tgcagagcaa tgggaactac     240
aagttcgatc agatgctcct gactgcccag aacctaccgg ccagctacaa ctactgcaga     300
ctagtgagtc ggagtctcac agtgaggtca agcacactcc tggtggcgt ttatgcacta     360 aacggcacca taaacgccgt gaccttccaa ggaagcctga gtgaactgac agatgttagc     420
tacaatgggt tgatgtctgc aacagccaac atcaacgaca aaattgggaa tgtcctggta     480
ggggaagggg tcactgtcct cagcctaccc acatcatatg atcttgggta tgtgaggctt     540 ggtgaccca ttcccgctat agggcttgac ccaaaaatgg tagctacatg cgacagcagt     600
gacaggccca gagtctacac cataactgca gccgatgatt accaattctc atcacagtac     660
caaccaggtg gggtaacaat cactctgttc tcagccaaca ttgatgctat cacaagcctc     720
agcattgggg gagagctcgt gtttcaaaca agcgtccaag ccttgtact gggcgccacc     780 atctacctta taggctttga tgggactgcg gtaatcacca gagctgtagc cgcagataat     840
gggctgacgg ccggcaccga caatcttatg ccattcaatc ttgtcattcc aaccaatgag     900
ataacccagc caatcacatc catcaaactg gagatagtga cctccaaaag tggtggtcag     960
```

-continued

```
gcagggatc agatgtcatg gtcggcaagt gggagcctag cagtgacgat ccatggtggc    1020
aactatccag gggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggaggt aa                       1362
```

<210> SEQ ID NO 8
<211> LENGTH: 453
<212> TYPE: PRT
<213> ORGANISM: artificial sequence
<220> FEATURE:
<223> OTHER INFORMATION: IBDV VP2 protein

<400> SEQUENCE: 8

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
```

```
              290                 295                 300
Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450

<210> SEQ ID NO 9
<211> LENGTH: 368
<212> TYPE: DNA
<213> ORGANISM: artificial sequence
<220> FEATURE:
<223> OTHER INFORMATION: SV40 promoter

<400> SEQUENCE: 9
gaattcgagc tcggtacagc ttggctgtgg aatgtgtgtc agttagggtg tggaaagtcc      60
ccaggctccc cagcaggcag aagtatgcaa agcatgcatc tcaattagtc agcaaccagg     120
tgtggaaagt ccccaggctc cccagcaggc agaagtatgc aaagcatgca tctcaattag     180
tcagcaacca tagtcccgcc cctaactccg cccatcccgc ccctaactcc gcccagttcc     240
gcccattctc cgccccatgg ctgactaatt ttttttattt atgcagaggc cgaggccgcc     300
tcggcctctg agctattcca gaagtagtga ggaggctttt ttggaggcct aggcttttgc     360
aaaaagct                                                             368

<210> SEQ ID NO 10
<211> LENGTH: 1391
<212> TYPE: DNA
<213> ORGANISM: artificial sequence
<220> FEATURE:
<223> OTHER INFORMATION: CMV-IE promoter

<400> SEQUENCE: 10
aactccgccc gttttatgac tagaaccaat agttttaat gccaaatgca ctgaaatccc       60
ctaatttgca aagccaaacg cccctatgt gagtaatacg ggactttttt acccaatttc      120
ccaagcggaa agcccctaa tacactcata tggcatatga atcagcacgg tcatgcactc     180
taatggcggc ccatagggac tttccacata ggggcgttc accatttccc agcataggg      240 tggtgactca atggccttta cccaagtaca ttgggtcaat gggaggtaag ccaatgggtt     300
tttcccatta ctggcaagca cactgagtca aatgggactt ccactgggt tttgcccaag     360 tacattgggt caatgggagg tgagccaatg ggaaaaaccc attgctgcca agtacactga     420
```

```
ctcaataggg actttccaat gggttttttcc attgttggca agcatataag gtcaatgtgg     480
gtgagtcaat agggactttc cattgtattc tgcccagtac ataaggtcaa taggggtga      540 atcaacagga aagtcccatt ggagccaagt acactgcgtc aatagggact ttccattggg     600
ttttgcccag tacataaggt caataggga tgagtcaatg gaaaaaccc attggagcca       660 agtacactga ctcaataggg actttccatt gggttttgcc cagtacataa ggtcaatagg    720
gggtgagtca acaggaaagt cccattggag ccaagtacat tgagtcaata gggactttcc    780
aatgggtttt gcccagtaca taaggtcaat gggaggtaag ccaatgggtt tttcccatta    840
ctggcacgta tactgagtca ttagggactt tccaatgggt tttgcccagt acataaggtc    900 aatagggtg aatcaacagg aaagtcccat tggagccaag tacactgagt caatagggac    960
tttccattgg ttttgccca gtacaaaagg tcaataggg gtgagtcaat gggttttcc      1020 cattattggc acgtacataa ggtcaatagg ggtgagtcat tgggtttttc cagccaattt   1080
aattaaaacg ccatgtactt tcccaccatt gacgtcaatg gctattgaa actaatgcaa    1140 cgtgaccttt aaacggtact ttcccatagc tgattaatgg gaaagtaccg ttctcgagcc   1200
aatacacgtc aatgggaagt gaaagggcag ccaaaacgta acaccgcccc ggttttcccc   1260
tggaaattcc atattggcac gcattctatt ggctgagctg cgttctacgt gggtataaga   1320
ggcgcgacca gcgtcggtac cgtcgcagtc ttcggtctga ccaccgtaga acgcagagct   1380
cctcgctgca g                                                         1391

<210> SEQ ID NO 11
<211> LENGTH: 218
<212> TYPE: DNA
<213> ORGANISM: artificial sequence
<220> FEATURE:
<223> OTHER INFORMATION: SV40 polyA signal

<400> SEQUENCE: 11
ggggatccag acatgataag atacattgat gagtttggac aaaccacaac tagaatgcag     60
tgaaaaaaat gctttatttg tgaaatttgt gatgctattg ctttatttgt aaccattata   120
agctgcaata aacaagttaa caacaacaat tgcattgatt ttatgtttca ggttcagggg   180
gaggtgtggg aggttttttc ggatcctcta gagtcgac                            218

<210> SEQ ID NO 12
<211> LENGTH: 155
<212> TYPE: DNA
<213> ORGANISM: artificial sequence
<220> FEATURE:
<223> OTHER INFORMATION: Synthetic polyA signal

<400> SEQUENCE: 12
aataaaatat ctttattttc attacatctg tgtgttggtt ttttgtgtga atcgatagta     60
ctaacatacg ctctccatca aaacaaaacg aaacaaaaca aactagcaaa ataggctgtc   120
cccagtgcaa gtgcaggtgc cagaacattt ctctt                               155

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
```

-continued

```
cgaacaaact tcatcgctat gc                                              22
```

<210> SEQ ID NO 14
<211> LENGTH: 22
<212> TYPE: DNA
<213> ORGANISM: artificial sequence
<220> FEATURE:
<223> OTHER INFORMATION: primer

<400> SEQUENCE: 14

```
taactcaaat gcgaagcgtt gc                                              22
```

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15

```
actgacaaca ccctacatgg c                                               21
```

<210> SEQ ID NO 16
<211> LENGTH: 19
<212> TYPE: DNA
<213> ORGANISM: artificial sequence
<220> FEATURE:
<223> OTHER INFORMATION: VIIoptF RP primer

<400> SEQUENCE: 16

```
gccagcacca ggctcaggg                                                  19
```

<210> SEQ ID NO 17
<211> LENGTH: 18
<212> TYPE: DNA
<213> ORGANISM: artificial sequence
<220> FEATURE:
<223> OTHER INFORMATION: primer

<400> SEQUENCE: 17

```
agcttggctg tggaatgt                                                   18
```

<210> SEQ ID NO 18
<211> LENGTH: 4344
<212> TYPE: DNA
<213> ORGANISM: artificial sequence
<220> FEATURE:
<223> OTHER INFORMATION: Partial plasmid pHM103+Fopt DNA sequence

<400> SEQUENCE: 18

```
gagctcaggg tatgatactc agctgttatt gtggccgacc aggaggactc caatgcttag     60
cattcataag aacgctagag atgctattta acgatgtgct gtcgtctaaa gaatttgtgc    120
atttagcctt taaatgtaaa accaatgacg cattcactac gctcgtgcgt gcaatttctg    180
ggccagggta tgcatattcc ataacagaaa tcgacacttg agaagaggat ctgactgttt    240
gggataaagg tcgtttgggt ctgtcctagc gatataattt atatgacgat atacattaaa    300
catctgtgtg cagtacttag gtatttaatc atgtcgatga atgttatgt gtaaatatcg     360
gacaatatag ataacgggca cgctgctatt gtaacgtgcg cccgcgcgct agtgctgact    420
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
```

```
ataagacttt ggtgcagtct cttcggggtc gcaatttaga tttgccgcat ggagggtatc      660
tggggatttt tgccaatgct ggagcgacga ctgtacgatt cgtcccatcg ggatctagca      720
gaccaatgat gttgacacac atcggccatg catgtacgga cggtctattg cgcgagtttg      780
ttattttcga aggacaagat ggaagtgtat atggaaccga caataatgtt agtttgcatt      840
tcttagggcg gaatctacat gatatcttat ccaagcgggg tatgagccag agagatgtga      900
tggtcataaa gggtaaattt tttagatctg aaataacgca gttgcccaaa caacgatcgc      960
gattaaaaga aaaatcggat ggttcaatta ggacatgcat ggattctgtg cgcataaacc     1020
ataaccgcag cactgttggg cacttcggta actcaaatgc gaagcgttgc acgtctgcga     1080
taactacgcc tactatgcac attgttactc ctgcatctta aaaatatatc ctgtagtaat     1140
tttcacagca atgtcataac atcatctcgc taaagaatga cctgggattg gagaagtaat     1200
gaatatttgc aaccaatgca ttgaataaac taacattaaa cgaattcgag ctcggtacag     1260
cttggctgtg gaatgtgtgt cagttagggt gtggaaagtc cccaggctcc ccagcaggca     1320
gaagtatgca aagcatgcat ctcaattagt cagcaaccag gtgtggaaag tccccaggct     1380
ccccagcagg cagaagtatg caaagcatgc atctcaatta gtcagcaacc atagtcccgc     1440
ccctaactcc gcccatcccg ccctaactc cgcccagttc cgcccattct ccgccccatg     1500
gctgactaat tttttttatt tatgcagagg ccgaggccgc ctcggcctct gagctattcc     1560
agaagtagtg aggaggcttt tttggaggcc taggcttttg caaaaagctg cggccgccac     1620
catgggcagc aagcccagca caagaatccc agccccctg atgctgatca cccgcatcat     1680
gctgatcctg ggctgcatca gacccacaag ctccctggat ggacgccccc tggccgctgc     1740
cggcatcgtg gtgaccggcg acaaggccgt gaacgtgtac accagcagcc agaccggcag     1800
catcatcgtg aagctgctgc ccaacatgcc cagagacaaa gaggcctgcg ccaaggcccc     1860
cctggaagcc tacaacagaa ccctgaccac cctgctgacc cccctgggcg acagcatcag     1920
aaagatccag ggctccgtga gcacaagcgg cggaggaaag cagggcagac tgatcggcgc     1980
cgtgatcggc agcgtggccc tgggagtggc tacagctgcc cagattaccg ctgcagccgc     2040
cctgatccag gccaaccaga acgccgccaa catcctgaga ctgaaagaga gcattgccgc     2100
caccaacgag gccgtgcacg aagtgaccga cggcctgagc cagctgtccg tggccgtggg     2160
caagatgcag cagttcgtga acgaccagtt caacaacacc gccagagagc tggactgcat     2220
caagatcacc cagcaggtgg gcgtggagct gaacctgtac ctgaccgagc tgaccacagt     2280
gttcggcccc cagatcacaa gcccagccct gacacagctg accatccagg ccctgtacaa     2340
cctggctggc ggcaacatgg actatctgct gacaaagctg ggaatcggca caaccagct     2400 gtccagcctg atcggaagcg gcctgatcac cggctacccc atcctgtacg acagccagac     2460
acagctgctg ggcatccagg tgaacctgcc cagcgtgggc aacctgaaca acatgcgcgc     2520
cacctacctg gaaaccctga gcgtgtccac caccaagggc tacgccagcg ccctggtgcc     2580
caaggtggtg acacaggtgg gcagcgtgat cgaggaactg acaccagct actgcatcga     2640 gagcgacctg gacctgtact gcaccagaat cgtgaccttc ccaatgagcc ccggcatcta     2700
cagctgcctg agcggcaaca ccagcgcctg catgtacagc aagaccgaag cgcactgac     2760 aacacccac atggccctga agggaagcgt gatcgccaac tgcaagatca ccacctgcag     2820
atgcaccgac cccccaggca tcatcagcca gaactacggc gaggccgtga gcctgatcga     2880
tcgccattcc tgtaacgtgc tgtccctgga cggcatcaca ctgagactga gcggcgagtt     2940
```

```
cgatgccacc taccagaaga acatcagcat cctggacagc caggtgatcg tgaccggcaa    3000
cctggacatc agcaccgagc tgggcaacgt gaataacagc atcagcaacg ccctggacag    3060
actggccgag agcaacagca agctggaaaa agtgaacgtg cgcctgacat ccacttccgc    3120
tctgatcacc tacatcgtgc tgaccgtgat cagcctggtg ttcggcgccc tgagcctggt    3180
gctggcctgc tacctgatgt acaagcagaa ggcccagcag aaaaccctgc tgtggctggg    3240
caacaacacc ctggaccaga tgagagccac caccagagcc tgatgagcgg ccgcggggat    3300
ccagacatga taagatacat tgatgagttt ggacaaacca caactagaat gcagtgaaaa    3360
aaatgcttta tttgtgaaat tgtgatgct  attgctttat tgtaaccat  tataagctgc    3420 aataaacaag ttaacaacaa caattgcatt gattttatgt ttcaggttca gggggaggtg    3480
tgggaggttt tttcggatcc tctagagtcg acaattattt tatttaataa catatagccc    3540
aaagacctct atgaacattt agtttcccgt atactcaacg gcgcgtgtac acacgcatct    3600
ctttgcatag cgatgaagtt tgttcggcag cagaaaatgc agatatccaa caatctggag    3660
aaaacttatc atcacagtgg cagtggaaac ataccccctc tatattcatg gtataattat    3720
cgtctacagc gtccaggata gtggcgtgag aaaatggaga tctgcagccc tcctttccat    3780
ggcatgccgc tttattgttc attaaacgca caatggtctc aacgccagat atgggcatag    3840
attctgaaga acccgttgac aatccgaaga agaaggcgtg caggtctttg gaagactcgc    3900
acgttggtct tataatgtat gatcgagatg tcaccctaat gccacatggt acaggcttat    3960
cgcggtcatg gcgatcggac ttgtaatttg caacgatggg caaggatcg  acgacatgcc    4020 aaacattctg aacccgtaga gatgttaacg atgacgagga tgaatatccc atgctcgctg    4080
ccatagtatc aagtacaccg cgaataagga cgcgtccaac atcgttatat gcacacaatg    4140
ggctacacgt gactaacacc cccgaatatt agtcatatgt gagtttcagt ctggctccca    4200
tatagcctgt agactatttg tggtttaagt gtgaacgagg cgctgtgaac gagactcggg    4260
ccgattgtaa gaacaagcaa atgcactttc catttaacaa gaagtgtaga gagaatactc    4320
aacctctttg gatgtatcct cgag                                            4344
```

<210> SEQ ID NO 19
<211> LENGTH: 4085
<212> TYPE: DNA
<213> ORGANISM: artificial sequence
<220> FEATURE:
<223> OTHER INFORMATION: Partial plasmid pSB1 44cds SV FCAopt sequence
      for vSB1-009

<400> SEQUENCE: 19

```
cttttgtcat gctcggagct ctgatcgcat cttatcatta cgtctgcata gcaacgtctg      60
gagacgtgac gtgaagacc  gggttttag  ttgtggcggc agggacgatt gccggcatca     120
cggctccgta tggagacatt tctcctctag ccggctttct ttcggcgtat acggcgttag     180
ctattcacgt ggtcagagac gccagtcggt ctctaatgaa cacgtgctac taccgtgcac     240
gtcgggaaat tactgtgaac ggtgcatatc gcctcggtcg cgcgcgtctc ccgcccagca     300
cggacgccga ggcgacgcgc gaagaagacg tatccagtta cgatacgctg ggggggaata     360
ttcctacgat aattctgagc ctcatagcgg tcatctcgat ccagccata  gccagctttc     420 aaaagtacat gtcgaacgca actaagcacc agtcaacatt gactgacacg ttacgcagta     480
tatgcggttt cttggtgggt acaagtgtcg cgatattcct tccgtcgcgc taccacgagg     540
ttctgttccg tccaattctt gtattactgt taatattcgg ggcaatggct actaccttag     600
```

```
ccggcttcgg tttacttctc gggccgacat tgttttccgc gacagccgcg gttctgtgct    660
gctacacttg tataaatgta cgcaacgcga atagcggaat aaagcaattg gcggccgccg    720
cagctggtaa atgcatatta ggaactgcca tctcgagcat gttggtttgc gtgttaatac    780
aatattcctg atcgcggagc gattaatttt tatatcatgt gctcatagcg ttctttcgaa    840
ctgcgaataa aactttcgtg gctactaaag gggcctatcg tgggtttatg cgctgtcgaa    900
aacatgaaag ggccgattta aagctaagtt gcgcaggcag aggccactcc atatacgctc    960
tcggagacgc ggctcgcacg ccagctgaaa tattttcccc cctgcaggtc gacccaattc   1020
gagctcggta cagcttggct gtggaatgtg tgtcagttag ggtgtggaaa gtccccaggc   1080
tccccagcag gcagaagtat gcaaagcatg catctcaatt agtcagcaac caggtgtgga   1140
aagtccccag gctccccagc aggcagaagt atgcaaagca tgcatctcaa ttagtcagca   1200
accatagtcc cgcccctaac tccgcccatc ccgcccctaa ctccgcccag ttccgcccat   1260
tctccgcccc atggctgact aattttttt atttatgcag aggccgaggc cgcctcggcc    1320
tctgagctat tccagaagta gtgaggaggc ttttttggag gcctaggctt ttgcaaaaag   1380
ctcccggggc ggccgccacc atgggcagca agcccagcac ctggatcagc gtgaccctga   1440
tgctgatcac cagaaccatg ctgatcctga gctgcatctg ccccacaagc agcctggacg   1500
gcagacccct ggccgctgcc ggcatcgtgg tgaccggcga caaggccgtg aacatctaca   1560
ccagcagcca gaccggcagc atcatcatca agctgctgcc caacatgccc aaggacaaag   1620
aggcctgcgc caaggccccc ctggaagcct acaacagaac cctgaccacc ctgctgaccc   1680
ccctgggcga cagcatcaga gaatccaggg cagcgccac cacaagcggc ggaggaaagc    1740
agggcagact ggtgggcgct atcatcggga gcgtggccct gggcgtggcc acagctgccc   1800
agattaccgc tgcagccgcc ctgattcagg ccaatcagaa cgccgccaac atcctgagac   1860
tgaaagagag cattgccgcc accaacgacg ccgtgcacga agtgacaaac ggactgtccc   1920
agctggctgt cgctgtcggc aagatgcagc agttcgtgaa caaccagttc aacaacaccg   1980
ccagagagct ggactgcatc aagatcgccc agcaggtggg cgtggagctg aacctgtacc   2040
tgaccgagct gaccacagtg ttcggccccc agatcacaag ccccgctctg acccagctga   2100
caatccaggc cctgtacaac ctggctggcg gcaacatgga ctatctgctg actaagctgg   2160
gagtgggcaa caaccagctg tccagcctga tcgggtccgg gctgatcaca ggcaacccca   2220
tcctgtacga cagccagaca cagctgctgg gcatccagat caacctgcca tccgtgggaa   2280
gcctgaacaa catgagagcc acctacctgg aaaccctgag cgtgtccacc accaagggct   2340
tcgccagcgc cctggtgccc aaggtggtga cacaggtggg cagcgtgatc gaggaactgg   2400
acaccagcta ctgcatcgag agcgacatcg acctgtactg caccagagtg gtgaccttcc   2460
caatgagccc cggcatctac agctgcctga gcggcaacac cagcgcctgc atgtacagca   2520
agaccgaagg agcactgaca cacccctaca tggccctgaa gggaagcgtg atcgccaact   2580
gcaagatgac cacctgcaga tgcgccgacc ccccaggcat catcagccag aactacggcg   2640
aggccgtgag cctgatcgac aaacattcct gtagcgtgct gtccctggat ggcatcacac   2700
tgagactgag cggcgagttc gacgccacct accagaagaa catcagcatc ctggacagcc   2760
aggtgatcgt gaccggcaac ctggacatca gcaccgagct gggcaacgtg aacaacagca   2820
tcagcagcac cctggacaag ctggccgagt ccaacaacaa gctgaacaaa gtgaacgtga   2880
acctgaccag cacaagcgcc ctgatcacct acatcgtgct ggccatcgtg tccctggcct   2940
tcggcgtgat cagcctggtg ctggcctgct acctgatgta caagcagaga gcccagcaga   3000
```

```
aaaccctgct gtggctgggc aataacaccc tggaccagat gagggccacc accagaacct    3060
gatgagcggc cgcgatacct gcaggtttgc ggtgacattg atctggctca ttatatgccc    3120
cgagctcttg taacatcgcg gacgcgattt ccgtagtagg cacatctcaa atgcaaaagc    3180
ggcatgtcaa ccgtataggt acatccggcc ctgcttacag tcggtagggc atatatccac    3240
cggaaaactt cagctttaga ctcctcaggt gatgaggaat agtatgtaac cctctagcag    3300
tacggtattt ctaaaaaaag gtagatcctt ttccacacgg cacagactaa ataacgtaca    3360
ctacacaggt tctctcgaac ttcgtttgga ccggaattat ccctcggca gcgcctaaaa    3420 agcaaacctc tagagtagat aagtgtcagt gaacctaggc cttctttgtt ccacggctgg    3480
aaagctaagg gacgaggtac acgcgacccc agccacgcac gaacagagtt taacggaagc    3540
gtcgtttgcg ggataaggtt gtcggacccc gcgggtccgt tgaaaagtgg ctgcgcgcct    3600
accgacgaat acgtcggtaa caattttaga aatcgaatat gactgcgagt accgtacaat    3660
cgcgaaatac ggtctctata tagctactcg gtccttaaat atgtaagtat gatgtcccct    3720
actcccgaag acgaccgcga cttggtcgca gtacgtgggc tgctccggat gatggacgag    3780
accacatctg agcgacacaa acgttcgcgt tcaggatgcc cccggttgtt atgcggttgt    3840
acgatcggga tcgctcttac tgtgttcgtc atcacagcta cggtcgtgct agcttcgctg    3900
tttgcattct cttacatgtc cctggagtcc ggtacatgtc ctcacgaatg gatcggttta    3960
ggctatagtt gtatgcgcgc gatggggagc aacgctaccg agctagaagc cctagatacg    4020
tgctcccgac ataacagcaa gcttgtcgac tttactcatg cgaaaattct aatcgaagct    4080
atcgc                                                                4085

<210> SEQ ID NO 20
<211> LENGTH: 4335
<212> TYPE: DNA
<213> ORGANISM: artificial sequence
<220> FEATURE:
<223> OTHER INFORMATION: Partial plasmid pHVT US2 SV-Fopt-SynPA for
      vHVT306

<400> SEQUENCE: 20
taaaatggga tctatcatta cattcgttaa gagtctggat aattttactg tttgccagct      60
tcgatcttgg aacgtactgt ggatagtgcc ttacttggaa tcgtgaaaat ttgaaacgtc     120
cattatttgg atatcttccg gttgtcccat atcccgccct ggtaccgctc ggataccttg     180
cccgtatgga ttcgtattga cagtcgcgca atcggggacc aacaacgcgt gggtccacac     240
tcattcggaa attttccgat gattctgaat atttattgcc gctcgttacg agtcgttgga     300
catatctgta atacatttct tcttctgaag gatcgctgca catttgatct atacattggc     360
caggatgttc aagtctcaga tgttgcattc tggcacagca caactttatg gcatttccga     420
tgtaatcgtc cggcagccct gggggagttc tatattcgca tattgggatg gtaaggacaa     480
tagcagatct cgcaacctcc agggaggcta ataacgtt tttaaggat ggatttctca     540 taaaaatctg tcgcaaatta cactgagaat atcctttact agcgccgatt gagagcatcg     600
tcgtccaatt ttctaaatgg aaagaaaaca aggcgggcaa gagtgttcca aacattttca     660
ttttcggcga atctctcaaa tcccatggcg tgcaattgat tgcaaaattg gcacttccgt     720
tcacgtttgt atctccaaac tctaagacac ttttaattga aaaactacgt tctagtgtgg     780
aaagaaacct ataggcagac catagaacta tttgacacca catatctttt tgtatgtcaa     840
actgaccatg atcgtatgtt gctgaatgca ctagggcaat tcgctcgcgc gactccatac     900
```

```
attgaataat tccacacgtc agctcatcgg ttagcaaggt ccagtagttg aagtcattta    960
tttttccccg cggctggcca aatctacctc tgggaatatc caagttgtcg aatatgatcg   1020
caccggctct ggtcatggtg aaggaacttg tagcataaag acgcaggtat cataggggta   1080
atatttttt attcactcac atactaaaag taacgcatat tagcaccatg tatgggctat    1140
caattgacat ttgcgtagca ctacatcacg attatgtaca acataatggg acaacatatg   1200
cctgcaggtc gacccaattc gagctcggta cagcttggct gtggaatgtg tgtcagttag   1260
ggtgtggaaa gtccccaggc tccccagcag gcagaagtat gcaaagcatg catctcaatt   1320
agtcagcaac caggtgtgga agtcccccag gctccccagc aggcagaagt atgcaaagca   1380
tgcatctcaa ttagtcagca accatagtcc cgcccctaac tccgcccatc ccgcccctaa   1440
ctccgcccag ttccgcccat tctccgcccc atggctgact aatttttttt atttatgcag   1500
aggccgaggc cgcctcggcc tctgagctat tccagaagta gtgaggaggc ttttttggag   1560
gcctaggctt ttgcaaaaag ctcccggggc ggccgccacc atgggcagca agcccagcac   1620
aagaatccca gccccctga tgctgatcac ccgcatcatg ctgatcctgg gctgcatcag    1680
acccacaagc tccctggatg gacgccccct ggccgctgcc ggcatcgtgg tgaccggcga   1740
caaggccgtg aacgtgtaca ccagcagcca gaccggcagc atcatcgtga agctgctgcc   1800
caacatgccc agagacaaag aggcctgcgc caaggccccc ctggaagcct acaacagaac   1860
cctgaccacc ctgctgaccc ccctgggcga cagcatcaga aagatccagg ctccgtgag    1920
cacaagcggc ggaggaaagc agggcagact gatcggcgcc gtgatcggca gcgtggccct   1980
gggagtggct acagctgccc agattaccgc tgcagccgcc ctgatccagg ccaaccagaa   2040
cgccgccaac atcctgagac tgaaagagag cattgccgcc accaacgagg ccgtgcacga   2100
agtgaccgac ggcctgagcc agctgtccgt ggccgtgggc aagatgcagc agttcgtgaa   2160
cgaccagttc aacaacaccg ccagagagct ggactgcatc aagatcaccc agcaggtggg   2220
cgtggagctg aacctgtacc tgaccgagct gaccacagtg ttcggccccc agatcacaag   2280
cccagccctg acacagctga ccatccaggc cctgtacaac ctggctggcg caacatggga   2340
ctatctgctg acaaagctgg gaatcggcaa caaccagctg tccagcctga tcggaagcgg   2400
cctgatcacc ggctaccca tcctgtacga cagccagaca cagctgctgg gcatccaggt   2460
gaacctgccc agcgtgggca acctgaacaa catgcgcgcc acctacctgg aaaccctgag   2520
cgtgtccacc accaagggct acgccagcgc cctggtgccc aaggtggtga cacaggtggg   2580
cagcgtgatc gaggaactgg acaccagcta ctgcatcgag agcgacctgg acctgtactg   2640
caccagaatc gtgaccttcc caatgagccc cggcatctac agctgcctga gcggcaacac   2700
cagcgcctgc atgtacagca agaccgaagg cgcactgaca acaccctaca tggccctgaa   2760
gggaagcgtg atcgccaact gcaagatcac cacctgcaga tgcaccgacc ccccaggcat   2820
catcagccag aactacggcg aggccgtgag cctgatcgat cgccattcct gtaacgtgct   2880
gtccctggac ggcatcacac tgagactgag cggcgagttc gatgccacct accagaagaa   2940
catcagcatc ctggacagcc aggtgatcgt gaccggcaac ctggacatca gcaccgagct   3000
gggcaacgtg aataacagca tcagcaacgc cctggacaga ctggccgaga gcaacagcaa   3060
gctggaaaaa gtgaacgtgc gcctgacatc cacttccgct ctgatcacct acatcgtgct   3120
gaccgtgatc agcctggtgt tcggcgccct gagcctggtg ctggcctgct acctgatgta   3180
caagcagaag gcccagcaga aaaccctgct gtggctgggc aacaacaccc tggaccagat   3240
```

| gagagccacc accagagcct gatgagcggc cgcgatatca ataaaatatc tttattttca | 3300 |
| ttacatctgt gtgttggttt tttgtgtgaa tcgatagtac taacatacgc tctccatcaa | 3360 |
| aacaaaacga aacaaaacaa actagcaaaa taggctgtcc ccagtgcaag tgcaggtgcc | 3420 |
| agaacatttc tcttctagac ctgcaggccc gggcaagtag atgcaatttc ctcacactag | 3480 |
| ttgggtttat ctactattga attttcccct atctgtgata cacttgggag cctctacaag | 3540 |
| catattgcca tcatgtacgt ttttatctac tgtcttaacg cccatgggaa cggaggcgtc | 3600 |
| gtcgtcatgt attggacggc aacataggca gcaacacaaa ttgcgtttag gtggggtgca | 3660 |
| tgtggactcg ataccaagcc cctgcagctg ggaacgtct ggtggagagc cgataatttg | 3720 |
| atatacgcac gccatattac tgtcgttgaa gtacgcctta tcttctatgt tttcaaattt | 3780 |
| aggttcccaa gtggacgtga gaagtgtttg tatctcacat ggaatggccc aaggcattcc | 3840 |
| agcccaggtg cctggtactt taatggcaaa caaacgtttt ggtagaggta ttgattctat | 3900 |
| tgcagttctg cagatatctg cagccccgag tatccacagg ctatacgata cgttatcgga | 3960 |
| ggcctccgat tctagcatta catagccggt cagtagatcc tgccattcgg tagcgcaacc | 4020 |
| ggctacatct tcaaacagtc tcacaataaa tgcatctctc gttcctgcca atccggaacc | 4080 |
| gggcatacca ctcccgcctg ccgatttaat tctcacaatt gggcgatgcc ggcggggcaa | 4140 |
| aacgaatgtg gatttggcaa accgacacag gtctgctgta cggactaata tgggcacacc | 4200 |
| cacatcattc ttcagatgct ccatgcattg ttctatgaga aagatccata gggtggaggc | 4260 |
| agcgtcacga gatcgcccag gcaatcgatc gcattcgtct agtaaagtga cgagagttat | 4320 |
| catgcacaca cccat | 4335 |

<210> SEQ ID NO 21
<211> LENGTH: 5381
<212> TYPE: DNA
<213> ORGANISM: artificial sequence
<220> FEATURE:
<223> OTHER INFORMATION: plasmid pCD046+NDV-F wt for vHVT110

<400> SEQUENCE: 21
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960

```
gattaaaaga aaaatcggat ggttcaatta ggacatgcat ggattctgtg cgcataaacc    1020
ataaccgcag cactgttggg cacttcggta actcaaatgc gaagcgttgc acgtctgcga    1080
taactacgcc tactatgcac attgttactc ctgcatctta aaatatatc ctgtagtaat     1140 tttcacagca atgtcataac atcatctcgc taaagaatga cctgggattg gagaagtaat    1200
gaatatttgc aaccaatgca ttgaataaac taacattaaa cgaattcaat agtggatccc    1260
ccaactccgc ccgttttatg actagaacca atagttttta atgccaaatg cactgaaatc    1320
ccctaatttg caaagccaaa cgcccccctat gtgagtaata cggggacttt tacccaatt    1380 tcccacgcgg aaagccccct aatacactca tatggcatat gaatcagcac ggtcatgcac    1440
tctaatggcg gcccataggg actttccaca tagggggcgt tcaccatttc ccagcatagg    1500
ggtggtgact caatggcctt tacccaagta cattgggtca atgggaggta agccaatggg    1560 ttttcccat tactggcaag cacactgagt caaatgggac tttccactgg ttttgccca      1620 agtacattgg gtcaatggga ggtgagccaa tgggaaaaac ccattgctgc caagtacact    1680
gactcaatag ggactttcca atgggttttt ccattgttgg caagcatata aggtcaatgt    1740
gggtgagtca atagggactt tccattgtat tctgcccagt acataaggtc aatagggggt    1800
gaatcaacag gaaagtccca ttggagccaa gtacactgcg tcaatagggga ctttccattg    1860 ggttttgccc agtacataag gtcaataggg gatgagtcaa tgggaaaaac ccattggagc    1920
caagtacact gactcaatag ggactttcca ttgggttttg cccagtacat aaggtcaata    1980
gggggtgagt caacaggaaa gttccattgg agccaagtac attgagtcaa tagggacttt    2040
ccaatgggtt ttgcccagta cataaggtca atgggaggta agccaatggg ttttcccat     2100 tactggcacg tatactgagt cattagggac tttccaatgg ttttgccca gtacataagg     2160 tcaatagggg tgaatcaaca ggaaagtccc attggagcca agtacactga gtcaatagg     2220 actttccatt gggttttgcc cagtacaaaa ggtcaatagg gggtgagtca atgggttttt    2280
cccattattg gcacgtacat aaggtcaata ggggtgagtc attgggtttt tccagccaat    2340
ttaattaaaa cgccatgtac tttcccacca ttgacgtcaa tggctattg aaactaatgc     2400 aacgtgacct ttaaacggta cttttcccata gctgattaat gggaaagtac cgttctcgag    2460
ccaatacacg tcaatgggaa gtgaaagggc agccaaaacg taacaccgcc ccggttttcc    2520
cctggaaatt ccatattggc acgcattcta ttggctgagc tgcgttctac gtgggtataa    2580
gaggcgcgac cagcgtcggt accgtcgcag tcttcggtct gaccaccgta gaacgcagag    2640
ctcctcgctg caggcggccg catgggctcc aaaccttcta ccaggatccc agcacctctg    2700
atgctgatca cccggattat gctgatattg gctgtatcc gtccgacaag ctctcttgac      2760
ggcaggcctc ttgcagctgc aggaattgta gtaacaggag ataaggcagt caatgtatac    2820
acttcgtctc agacagggtc aatcatagtc aagttgctcc cgaatatgcc cagggataag    2880
gaggcgtgtg caaaagcccc attagaggca tataacagaa cactgactac tttgctcact    2940
cctcttggcg actccatccg caagatccaa gggtctgtgt ccacatctgg aggaggcaag    3000
caaggccgcc tgataggtgc tgttattggc agtgtagctc ttggggttgc aacagcggca    3060
cagataacag cagctgcggc cctaatacaa gccaaccaga atgccgccaa catcctccgg    3120
cttaaggaga gcattgctgc aaccaatgaa gctgtgcatg aagtcaccga cggattatca    3180
caactatcag tggcagttgg gaagatgcag cagtttgtca atgaccagtt taataatacg    3240
gcgcgagaat tggactgtat aaaaatcaca caacaggttg gtgtagaact caacctatac    3300
```

```
ctaactgaat tgactacagt attcgggcca cagatcacct ccctgcatt aactcagctg    3360 accatccagg cactttataa tttagctggt ggcaatatgg attacttatt aactaagtta    3420
ggtataggga acaatcaact cagctcgtta attggtagcg gcctgatcac tggttaccct    3480
atactgtatg actcacagac tcaactcttg ggcatacaag tgaatttacc ctcagtcggg    3540
aacttaaata atatgcgtgc cacctatttg gagaccttat ctgtaagtac aaccaaagga    3600
tatgcctcag cacttgtccc gaaagtagtg acacaagtcg gttccgtgat agaagagctt    3660
gacacctcat actgtatcga gtccgatctg gatttatatt gtactagaat agtgacattc    3720
cccatgtccc caggtattta ttcctgtttg agcggcaaca catcagcttg catgtattca    3780
aagactgaag gcgcactcac tacgccgtat atggccctta aaggctcagt tattgccaat    3840
tgtaaaataa caacatgtag atgtacagac cctcctggta tcatatcgca aaattatgga    3900
gaagctgtat ccctgataga tagacattcg tgcaatgtct tatcattaga cgggataact    3960
ctaaggctca gtgggaatt tgatgcaact tatcaaaaga acatctcaat actagattct    4020
caagtcatcg tgacaggcaa tcttgatata tcaactgaac ttggaaacgt caacaattca    4080
atcagcaatg ccttggatag gttggcagaa agcaacagca agctagaaaa agtcaatgtc    4140
agactaacca gcacatctgc tctcattacc tatattgttc taactgtcat ttctctagtt    4200
ttcggtgcac ttagtctggt gttagcgtgt tacctgatgt acaaacagaa ggcacaacaa    4260
aagaccttgc tatggcttgg gaataatacc ctcgatcaga tgagagccac tacaagagca    4320
tgagcggccg cggggatcca gacatgataa gatacattga tgagtttgga caaccacaa    4380 ctagaatgca gtgaaaaaaa tgctttattt gtgaaatttg tgatgctatt gctttatttg    4440
taaccattat aagctgcaat aaacaagtta caacaacaa ttgcattgat tttatgttc    4500 aggttcaggg ggaggtgtgg gaggttttt cggatcctct agagtcgaca attattttat    4560
ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata ccccctctat    4740
attcatggta taattatcgt ctacagcgtc caggatagtg gcgtgagaaa atggagatct    4800
gcagccctcc tttccatggc atgccgcttt attgttcatt aaacgcacaa tggtctcaac    4860
gccagatatg gcatagatt ctgaagaacc cgttgacaat ccgaagaaga aggcgtgcag    4920
gtctttggaa gactcgcacg ttggtcttat aatgtatgat cgagatgtca ccctaatgcc    4980
acatggtaca ggcttatcgc ggtcatggcg atcggacttg taatttgcaa cgatgggcaa    5040
aggatcgacg acatgccaaa cattctgaac ccgtagagat gttaacgatg acgaggatga    5100
atatcccatg ctcgctgcca tagtatcaag tacaccgcga ataaggacgc gtccaacatc    5160
gttatatgca cacaatgggc tacacgtgac taacaccccc gaatattagt catatgtgag    5220
tttcagtctg gctcccatat agcctgtaga ctatttgtgg tttaagtgtg aacgaggcgc    5280
tgtgaacgag actcgggccg attgtaagaa caagcaaatg cactttccat ttaacaagaa    5340
gtgtagagag aatactcaac ctcttggat gtatcctcga g                       5381
```

<210> SEQ ID NO 22
<211> LENGTH: 4337
<212> TYPE: DNA
<213> ORGANISM: artificial sequence
<220> FEATURE:
<223> OTHER INFORMATION: Partial plasmid pHM103+NDV-F wt sequence for vHVT111

```
<400> SEQUENCE: 22
gagctcaggg tatgatactc agctgttatt gtggccgacc aggaggactc caatgcttag      60
cattcataag aacgctagag atgctattta acgatgtgct gtcgtctaaa gaatttgtgc     120
atttagcctt taaatgtaaa accaatgacg cattcactac gctcgtgcgt gcaatttctg     180
ggccagggta tgcatattcc ataacagaaa tcgacacttg agaagaggat ctgactgttt     240
gggataaagg tcgtttgggt ctgtcctagc gatataattt atatgacgat atacattaaa     300
catctgtgtg cagtacttag gtatttaatc atgtcgatga aatgttatgt gtaaatatcg     360
gacaatatag ataacgggca cgctgctatt gtaacgtgcg cccgcgcgct agtgctgact     420
aatagtgtgg atgatgtata cagtatatta caaacggaaa tgatacgtaa taaattatgt     480
actcttattg atttataaaa acatacatgc agtgttgcta tgtcacataa ttagcctcgc     540
ccgtctacgc tccactgaag ataatgggct cccgctgttc aaaaaaatca gcgtgcgtcg     600
ataagacttt ggtgcagtct cttcggggtc gcaatttaga tttgccgcat ggagggtatc     660
tggggatttt tgccaatgct ggagcgacga ctgtacgatt cgtcccatcg ggatctagca     720
gaccaatgat gttgacacac atcggccatg catgtacgga cggtctattg cgcgagtttg     780
ttattttcga aggacaagat ggaagtgtat atggaaccag caataatgtt agtttgcatt     840
tcttagggcg gaatctacat gatatcttat ccaagcgggg tatgagccag agagatgtga     900
tggtcataaa gggtaaattt tttagatctg aaataacgca gttgcccaaa caacgatcgc     960
gattaaaaga aaaatcggat ggttcaatta ggacatgcat ggattctgtg cgcataaacc    1020
ataaccgcag cactgttggg cacttcggta actcaaatgc gaagcgttgc acgtctgcga    1080
taactacgcc tactatgcac attgttactc ctgcatctta aaaatatatc ctgtagtaat    1140
tttcacagca atgtcataac atcatctcgc taaagaatga cctgggattg gagaagtaat    1200
gaatatttgc aaccaatgca ttgaataaac taacattaaa cgaattcgag ctcggtacag    1260
cttggctgtg gaatgtgtgt cagttagggt gtggaaagtc cccaggctcc ccagcaggca    1320
gaagtatgca aagcatgcat ctcaattagt cagcaaccag gtgtggaaag tccccaggct    1380
ccccagcagg cagaagtatg caaagcatgc atctcaatta gtcagcaacc atagtcccgc    1440
ccctaactcc gcccatcccg ccctaactcc gcccagttc cgcccattct ccgccccatg     1500
gctgactaat tttttttatt tatgcagagg ccgaggccgc ctcggcctct gagctattcc    1560
agaagtagtg aggaggcttt tttggaggcc taggcttttg caaaaagctg cggccgcatg    1620
ggctccaaac cttctaccag gatcccagca cctctgatgc tgatcacccg gattatgctg    1680
atattgggct gtatccgtcc gacaagctct cttgacggca ggcctcttgc agctgcagga    1740
attgtagtaa caggagataa ggcagtcaat gtatacactt cgtctcagac agggtcaatc    1800
atagtcaagt tgctcccgaa tatgcccagg gataaggagg cgtgtgcaaa agccccatta    1860
gaggcatata acagaacact gactactttg ctcactcctc ttggcgactc catccgcaag    1920
atccaagggt ctgtgtccac atctggagga ggcaagcaag gccgcctgat aggtgctgtt    1980
attggcagtg tagctcttgg ggttgcaaca gcggcacaga taacagcagc tgcggcccta    2040
atacaagcca accagaatgc cgccaacatc ctccggctta aggagagcat tgctgcaacc    2100
aatgaagctg tgcatgaagt caccgacgga ttatcacaac tatcagtggc agttgggaag    2160
atgcagcagt ttgtcaatga ccagtttaat aatacggcgc gagaattgga ctgtataaaa    2220
atcacacaac aggttggtgt agaactcaac ctatacctaa ctgaattgac tacagtattc    2280
gggccacaga tcacctcccc tgcattaact cagctgacca tccaggcact ttataattta    2340
```

```
gctggtggca atatggatta cttattaact aagttaggta tagggaacaa tcaactcagc    2400
tcgttaattg gtagcggcct gatcactggt tacccctatac tgtatgactc acagactcaa    2460
ctcttgggca tacaagtgaa tttaccctca gtcgggaact taaataatat gcgtgccacc    2520
tatttggaga ccttatctgt aagtacaacc aaaggatatg cctcagcact tgtcccgaaa    2580
gtagtgacac aagtcggttc cgtgatagaa gagcttgaca cctcatactg tatagagtcc    2640
gatctggatt tatattgtac tagaatagtg acattcccca tgtccccagg tatttattcc    2700
tgtttgagcg gcaacacatc agcttgcatg tattcaaaga ctgaaggcgc actcactacg    2760
ccgtatatgg cccttaaagg ctcagttatt gccaattgta aaataacaac atgtagatgt    2820
acagaccctc ctggtatcat atcgcaaaat tatggagaag ctgtatccct gatagataga    2880
cattcgtgca atgtcttatc attagacggg ataactctaa ggctcagtgg ggaatttgat    2940
gcaacttatc aaaagaacat ctcaatacta gattctcaag tcatcgtgac aggcaatctt    3000
gatatatcaa ctgaacttgg aaacgtcaac aattcaatca gcaatgcctt ggataggttg    3060
gcagaaagca acagcaagct agaaaaagtc aatgtcagac taaccagcac atctgctctc    3120
attacctata ttgttctaac tgtcatttct ctagttttcg gtgcacttag tctggtgtta    3180
gcgtgttacc tgatgtacaa acagaaggca caacaaaaga ccttgctatg gcttgggaat    3240 aatacccctcg atcagatgag agccactaca agagcatgag cggccgcggg gatccagaca    3300
tgataagata cattgatgag tttggacaaa ccacaactag aatgcagtga aaaaaatgct    3360
ttatttgtga aatttgtgat gctattgctt tatttgtaac cattataagc tgcaataaac    3420
aagttaacaa caacaattgc attgatttta tgtttcaggt tcaggggag gtgtgggagg    3480 ttttttcgga tcctctagag tcgacaatta ttttatttaa taacatatag cccaaagacc    3540
tctatgaaca tttagttcc cgtatactca acggcgcgtg tacacacgca tctctttgca    3600
tagcgatgaa gtttgttcgg cagcagaaaa tgcagatatc caacaatctg agaaaactt    3660 atcatcacag tggcagtgga aacatacccc ctctatattc atggtataat tatcgtctac    3720
agcgtccagg atagtggcgt gagaaaatgg agatctgcag ccctcctttc catggcatgc    3780
cgctttattg ttcattaaac gcacaatggt ctcaacgcca gatatgggca tagattctga    3840
agaacccgtt gacaatccga agaagaaggc gtgcaggtct ttggaagact cgcacgttgg    3900
tcttataatg tatgatcgag atgtcaccct aatgccacat ggtacaggct atcgcggtc    3960 atggcgatcg gacttgtaat ttgcaacgat gggcaaagga tcgacgacat gccaaacatt    4020
ctgaacccgt agagatgtta acgatgacga ggatgaatat cccatgctcg ctgccatagt    4080
atcaagtaca ccgcgaataa ggacgcgtcc aacatcgtta tatgcacaca atgggctaca    4140
cgtgactaac acccccgaat attagtcata tgtgagtttc agtctggctc ccatatagcc    4200
tgtagactat ttgtggttta agtgtgaacg aggcgctgtg aacgagactc gggccgattg    4260
taagaacaag caaatgcact ttccatttaa caagaagtgt agagagaata ctcaacctct    4320
ttggatgtat cctcgag                                                   4337
```

<210> SEQ ID NO 23
<211> LENGTH: 4344
<212> TYPE: DNA
<213> ORGANISM: artificial sequence
<220> FEATURE:
<223> OTHER INFORMATION: Partial plasmid pHM103+NDV-F CA

```
gagctcaggg tatgatactc agctgttatt gtggccgacc aggaggactc caatgcttag    60
cattcataag aacgctagag atgctattta acgatgtgct gtcgtctaaa gaatttgtgc   120
atttagcctt taaatgtaaa accaatgacg cattcactac gctcgtgcgt gcaatttctg   180
ggccagggta tgcatattcc ataacagaaa tcgacacttg agaagaggat ctgactgttt   240
gggataaagg tcgtttgggt ctgtcctagc gatataattt atatgacgat atacattaaa   300
catctgtgtg cagtacttag gtatttaatc atgtcgatga atgttatgt gtaaatatcg    360 gacaatatag ataacgggca cgctgctatt gtaacgtgcg cccgcgcgct agtgctgact   420
aatagtgtgg atgatgtata cagtatatta caaacggaaa tgatacgtaa taaattatgt   480
actcttattg atttataaaa acatacatgc agtgttgcta tgtcacataa ttagcctcgc   540
ccgtctacgc tccactgaag ataatgggct cccgctgttc aaaaaaatca gcgtgcgtcg   600
ataagacttt ggtgcagtct cttcggggtc gcaatttaga tttgccgcat ggagggtatc   660
tggggatttt tgccaatgct ggagcgacga ctgtacgatt cgtcccatcg ggatctagca   720
gaccaatgat gttgacacac atcggccatg catgtacgga cggtctattg cgcgagtttg   780
ttattttcga aggacaagat ggaagtgtat atggaaccga caataatgtt agtttgcatt   840
tcttagggcg gaatctacat gatatcttat ccaagcgggg tatgagccag agagatgtga   900
tggtcataaa gggtaaattt tttagatctg aaataacgca gttgcccaaa caacgatcgc   960
gattaaaaga aaaatcggat ggttcaatta ggacatgcat ggattctgtg cgcataaacc  1020
ataaccgcag cactgttggg cacttcggta actcaaatgc gaagcgttgc acgtctgcga  1080
taactacgcc tactatgcac attgttactc ctgcatctta aaaatatatc ctgtagtaat  1140
tttcacagca atgtcataac atcatctcgc taaagaatga cctgggattg gagaagtaat  1200
gaatatttgc aaccaatgca ttgaataaac taacattaaa cgaattcgag ctcggtacag  1260
cttggctgtg gaatgtgtgt cagttagggt gtggaaagtc cccaggctcc ccagcaggca  1320
gaagtatgca aagcatgcat ctcaattagt cagcaaccag gtgtggaaag tccccaggct  1380
ccccagcagg cagaagtatg caaagcatgc atctcaatta gtcagcaacc atagtcccgc  1440
ccctaactcc gcccatcccg cccctaactc cgcccagttc cgcccattct ccgccccatg  1500
gctgactaat ttttttttatt tatgcagagg ccgaggccgc ctcggcctct gagctattcc  1560
agaagtagtg aggaggcttt tttggaggcc taggcttttg caaaaagctg cggccgccac  1620
catgggcagc aagcccagca cctggatcag cgtgacccctg atgctgatca ccagaaccat  1680
gctgatcctg agctgcatct gccccacaag cagcctggac ggcagacccc tggccgctgc  1740
cggcatcgtg gtgaccggcg acaaggccgt gaacatctac accagcagcc agaccggcag  1800
catcatcatc aagctgctgc ccaacatgcc caaggacaaa gaggcctgcg ccaaggcccc  1860
cctggaagcc tacaacagaa ccctgaccac cctgctgacc cccctgggcg acagcatcag  1920
aagaatccag ggcagcgcca ccacaagcgg cggaggaaag cagggcagac tggtgggcgc  1980
tatcatcggg agcgtggccc tgggcgtggc cacagctgcc cagattaccg ctgcagccgc  2040
cctgattcag gccaatcaga acgccgccaa catcctgaga ctgaaagaga gcattgccgc  2100
caccaacgac gccgtgcacg aagtgacaaa cggactgtcc cagctggctg tcgctgtcgg  2160
caagatgcag cagttcgtga caaccagtt caacaacacc gccagagagc tggactgcat  2220
caagatcgcc cagcaggtgg gcgtggagct gaacctgtac ctgaccgagc tgaccacagt  2280
gttcggcccc cagatcacaa gccccgctct gacccagctg acaatccagg ccctgtacaa  2340
cctggctggc ggcaacatgg actatctgct gactaagctg ggagtgggca caaccagct   2400
```

```
gtccagcctg atcgggtccg ggctgatcac aggcaacccc atcctgtacg acagccagac    2460
acagctgctg ggcatccaga tcaacctgcc atccgtggga agcctgaaca acatgagagc    2520
cacctacctg gaaaccctga gcgtgtccac caccaagggc ttcgccagcg ccctggtgcc    2580
caaggtggtg acacaggtgg gcagcgtgat cgaggaactg acaccagct  actgcatcga    2640 gagcgacatc gacctgtact gcaccagagt ggtgaccttc ccaatgagcc ccggcatcta    2700
cagctgcctg agcggcaaca ccagcgcctg catgtacagc aagaccgaag agcactgac    2760 aacaccctac atggccctga agggaagcgt gatcgccaac tgcaagatga ccacctgcag    2820
atgcgccgac ccccaggca  tcatcagcca gaactacggc gaggccgtga gcctgatcga    2880
caaacattcc tgtagcgtgc tgtccctgga tggcatcaca ctgagactga gcggcgagtt    2940
cgacgccacc taccagaaga acatcagcat cctggacagc caggtgatcg tgaccggcaa    3000
cctggacatc agcaccgagc tgggcaacgt gaacaacagc atcagcagca ccctggacaa    3060 gctgccgag  tccaacaaca agctgaacaa agtgaacgtg aacctgacca gcacaagcgc    3120
cctgatcacc tacatcgtgc tggccatcgt gtccctggcc ttcggcgtga tcagcctggt    3180
gctggcctgc tacctgatgt acaagcagag agcccagcag aaaaccctgc tgtggctggg    3240
caataacacc ctggaccaga tgagggccac caccagaacc tgatgagcgg ccgcggggat    3300
ccagacatga taagatacat tgatgagttt ggacaaacca aactagaat  gcagtgaaaa    3360 aaatgcttta tttgtgaaat tgtgatgct  attgctttat ttgtaaccat tataagctgc    3420
aataaacaag ttaacaacaa caattgcatt gattttatgt ttcaggttca gggggaggtg    3480
tgggaggttt tttcggatcc tctagagtcg acaattattt tatttaataa catatagccc    3540
aaagacctct atgaacattt agtttcccgt atactcaacg gcgcgtgtac acacgcatct    3600
ctttgcatag cgatgaagtt tgttcggcag cagaaaatgc agatatccaa caatctggag    3660
aaaacttatc atcacagtgg cagtggaaac ataccccctc tatattcatg gtataattat    3720
cgtctacagc gtccaggata gtggcgtgag aaaatggaga tctgcagccc tcctttccat    3780
ggcatgccgc tttattgttc attaaacgca caatggtctc aacgccagat atgggcatag    3840
attctgaaga acccgttgac aatccgaaga agaaggcgtg caggtctttg aagagactcgc   3900 acgttggtct tataatgtat gatcgagatg tcaccctaat gccacatggt acaggcttat    3960
cgcggtcatg cgatcggac  ttgtaatttg caacgatggg caaggatcg  acgacatgcc    4020 aaacattctg aacccgtaga gatgttaacg atgacgagga tgaatatccc atgctcgctg    4080
ccatagtatc aagtacaccg cgaataagga cgcgtccaac atcgttatat gcacacaatg    4140
ggctacacgt gactaacacc cccgaatatt agtcatatgt gagtttcagt ctggctccca    4200
tatagcctgt agactatttg tggtttaagt gtgaacgagg cgctgtgaac gagactcggg    4260
ccgattgtaa gaacaagcaa atgcactttc catttaacaa gaagtgtaga gagaatactc    4320
aacctctttg gatgtatcct cgag                                          4344
```

<210> SEQ ID NO 24
<211> LENGTH: 3988
<212> TYPE: DNA
<213> ORGANISM: artificial sequence
<220> FEATURE:
<223> OTHER INFORMATION: Partial plasmid HVTIG2 SV Fwt SbfI sequence for vHVT301

<400> SEQUENCE: 24

```
tgtttcgcac catatccaag ctggctgtcc ctaagagctt attcctgcaa gacctcatac      60
```

```
ggaataattg cccgaccaat acttattacg gacataggta ggccgataaa tattatgttg    120
actggaggat ggaaaggagg ttttgtaaca gctacatcgc tcgttcatca gcaagcgata    180
ctttggatat ccgagcttca aaagccgcat aaaccccgct ttatttctga atacgcccca    240
acagtaacac atgcgtggtt cctggcactt ggaacgccgt gttttatagg caagaacata    300
ctacccaaag aggtcttggg atttctggcg cgtcgttgca atgaagaaat gaattctttg    360
ttccttgaaa tgccgacaac tctaaaaacg gtattcgagc accattactt tacgcgtgga    420
tctgaagtaa atccagcgtt gttgatggag cctaacagat ttttgcaact gatggattcg    480
cggaaaatcc tatgtttata cgaatccgct atgtgcgaca accccggagc tcagggtatg    540
atactcagct gttattgtgg ccgaccagga ggactccaat gcttagcatt cataagaacg    600
ctagagatgc tatttaacga tgtgctgtcg tctaaagaat ttgtgcattt agcctttaaa    660
tgtaaaacca atgacgcatt cactacgctc gtgcgtgcaa tttctgggcc agggtatgca    720
tattccataa cagaaatcga cacttgagaa gaggatctga ctgtttggga taaggtcgt    780 ttgggtctgt cctagcgata taatttatat gacgatatac attaaacatc tgtgtgcagt    840
acttaggtat ttaatcatgt cgatgaaatg ttatgtgtaa atatcggaca atatagataa    900
cgggcacgct gctattgtaa cgtgcgcccg cgcgctagtg ctgactaata gtgtggatga    960
tgtatacagt atattacaaa cggaaatgat acgtaataaa cctgcaggtc gacccaattc   1020
gagctcggta cagcttggct gtggaatgtg tgtcagttag ggtgtggaaa gtccccaggc   1080
tccccagcag gcagaagtat gcaaagcatg catctcaatt agtcagcaac caggtgtgga   1140
aagtccccag gctccccagc aggcagaagt atgcaaagca tgcatctcaa ttagtcagca   1200
accatagtcc cgcccctaac tccgcccatc ccgcccctaa ctccgcccag ttccgcccat   1260
tctccgcccc atggctgact aattttttt atttatgcag aggccgaggc cgcctcggcc   1320
tctgagctat tccagaagta gtgaggaggc tttttggag gcctaggctt ttgcaaaaag   1380
ctgcggccgc atgggctcca aaccttctac caggatccca gcacctctga tgctgatcac   1440
ccggattatg ctgatattgg gctgtatccg tccgacaagc tctcttgacg gcaggcctct   1500
tgcagctgca ggaattgtag taacaggaga taaggcagtc aatgtataca cttcgtctca   1560
gacagggtca atcatagtca agttgctccc gaatatgccc agggataagg aggcgtgtgc   1620
aaaagcccca ttagaggcat ataacagaac actgactact tgctcactc ctcttggcga   1680 ctccatccgc aagatccaag ggtctgtgtc cacatctgga ggaggcaagc aaggccgcct   1740
gataggtgct gttattggca gtgtagctct tggggttgca acagcggcac agataacagc   1800
agctgcggcc ctaatacaag ccaaccagaa tgccgccaac atcctccggc ttaaggagag   1860
cattgctgca accaatgaag ctgtgcatga agtcaccgac ggattatcac aactatcagt   1920
ggcagttggg aagatgcagc agtttgtcaa tgaccagttt aataatacgg cgcgagaatt   1980
ggactgtata aaaatcacac aacaggttgg tgtagaactc aacctatacc taactgaatt   2040
gactacagta ttcgggccac agatcacctc ccctgcatta actcagctga ccatccaggc   2100
actttataat ttagctggtg gcaatatgga ttacttatta actaagttag gtataggga    2160 caatcaactc agctcgttaa ttggtagcgg cctgatcact ggttacccta tactgtatga   2220
ctcacagact caactcttgg gcatacaagt gaatttaccc tcagtcggga acttaaataa   2280
tatgcgtgcc acctatttgg agaccttatc tgtaagtaca accaaaggat atgcctcagc   2340
acttgtcccg aaagtagtga cacaagtcgg ttccgtgata gaagagcttg acacctcata   2400
```

```
ctgtatagag tccgatctgg atttatattg tactagaata gtgacattcc ccatgtcccc   2460
aggtatttat tcctgtttga gcggcaacac atcagcttgc atgtattcaa agactgaagg   2520
cgcactcact acgccgtata tggcccttaa aggctcagtt attgccaatt gtaaaataac   2580
aacatgtaga tgtacagacc ctcctggtat catatcgcaa aattatggag aagctgtatc   2640
cctgatagat agacattcgt gcaatgtctt atcattagac gggataactc taaggctcag   2700
tggggaattt gatgcaactt atcaaaagaa catctcaata ctagattctc aagtcatcgt   2760
gacaggcaat cttgatatat caactgaact tggaaacgtc aacaattcaa tcagcaatgc   2820
cttggatagg ttggcagaaa gcaacagcaa gctagaaaaa gtcaatgtca gactaaccag   2880
cacatctgct ctcattacct atattgttct aactgtcatt tctctagttt tcggtgcact   2940
tagtctggtg ttagcgtgtt acctgatgta caaacagaag gcacaacaaa agaccttgct   3000
atggcttggg aataataccc tcgatcagat gagagccact acaagagcat gagcggccgc   3060
ggggatccag acatgataag atacattgat gagtttggac aaaccacaac tagaatgcag   3120
tgaaaaaaat gctttatttg tgaaatttgt gatgctattg ctttatttgt aaccattata   3180
agctgcaata aacaagttaa caacaacaat tgcattgatt ttatgtttca ggttcagggg   3240
gaggtgtggg aggtttttc ggatcctcta gaggggatta atcctgcagg ttatgtactc   3300
ttattgattt ataaaaacat acatgcagtg ttgctatgtc acataattag cctcgcccgt   3360
ctacgctcca ctgaagataa tgggctcccg ctgttcaaaa aaatcagcgt gcgtcgataa   3420
gactttggtg cagtctcttc ggggtcgcaa tttagatttg ccgcatggag ggtatctggg   3480
gatttttgcc aatgctggag cgacgactgt acgattcgtc ccatcgggat ctagcagacc   3540
aatgatgttg acacacatcg gccatgcatg tacggacggt ctattgcgcg agtttgttat   3600
tttcgaagga caagatggaa gtgtatatgg aaccgacaat aatgttagtt tgcatttctt   3660
agggcggaat ctacatgata tcttatccaa gcggggtatg agccagagag atgtgatggt   3720
cataaagggt aaattttta gatctgaaat aacgcagttg cccaaacaac gatcgcgatt   3780
aaaagaaaaa tcggatggtt caattaggac atgcatggat tctgtgcgca taaaccataa   3840
ccgcagcact gttgggcact tcggtaactc aaatgcgaag cgttgcacgt ctgcgataac   3900
tacgcctact atgcacattg ttactcctgc atcttaaaaa tatatcctgt agtaattttc   3960
acagcaatgt cataacatca tctcgcta                                      3988
```

<210> SEQ ID NO 25
<211> LENGTH: 3707
<212> TYPE: DNA
<213> ORGANISM: artificial sequence
<220> FEATURE:
<223> OTHER INFORMATION: Partial plasmid pHVTUS10 cds F opt plasmid for vHVT302

<400> SEQUENCE: 25

```
tcccttacgg cggatcgaaa cgacattagg catactcggg taccattttg cattccgatc     60
agcacggatg aaattaggca ggaatgcggt ttatattatg cggcattgga caaacgatat    120
ggcattgatt ggcagtttat gaatgtcttc atgttgggcg taaacggatt cctattggtt    180
cagaagacaa cgacgatata tttagagaga aaaagctacc cagcatagga taaacacaca    240
ttgagcattg agagacatag gtatcggtat ggatgggaaa actacacacg tgaacaccaa    300
acgacttata tactcgagcg gtgatactac tgagcaagaa tgcactgcat ctgagccact    360
gaatgaagac tgtgatgaaa atgtgaccat cgatggaatt ggagaagaat atgcgcagtt    420
```

```
cttcatgtcc ccgcaatggg tcccaaatct acatcgcttg agcgaggata ccaaaaaggt    480
ataccgatgt atggtttcca acagactcaa ttattttccc tattatgagg cgttcaggcg    540
gtctttgttt gatatgtata tgctaggtcg gttgggggcgt cgacttaagc gatctgactg    600
ggagactatt atgcatctgt caccaacgca aagtcggcc ctacatagaa ctttaagatt    660
tgtggagcgt agaattatcc catctaacag ttatatacgc acatcgggcc acgttccgcc    720
ttcgagggca cttccgacag atacgaattt aaagatggat gaataattaa attggaaaga    780
gtaactacat taatcgagcg tcatgacggc gtcccgtgaa aatgggaatt ttctactcga    840
aacaccgtga catttgacag acctggaatt gttattctga tatatagtgg gtgtgtctgg    900
ccggcaacat acataatgtg catgcgaaac cactttttca gtgtacgctg acattgtgca    960
acacggaggg gtagcatcta catacaatat atgttgatta cctgcagggc ggccgccacc   1020
atgggcagca agcccagcac aagaatccca gccccctga tgctgatcac ccgcatcatg   1080
ctgatcctgg gctgcatcag acccacaagc tccctggatg gacgccccct ggccgctgcc   1140
ggcatcgtgg tgaccggcga caaggccgtg aacgtgtaca ccagcagcca gaccggcagc   1200
atcatcgtga agctgctgcc caacatgccc agagacaaag aggcctgcgc caaggccccc   1260
ctggaagcct acaacagaac cctgaccacc ctgctgaccc ccctgggcga cagcatcaga   1320
aagatccagg gctccgtgag cacaagcggc ggaggaaagc agggcagact gatcggcgcc   1380
gtgatcggca gcgtggccct gggagtggct acagctgccc agattaccgc tgcagccgcc   1440
ctgatccagg ccaaccagaa cgccgccaac atcctgagac tgaaagagag cattgccgcc   1500
accaacgagg ccgtgcacga agtgaccgac ggcctgagcc agctgtccgt ggccgtgggc   1560
aagatgcagc agttcgtgaa cgaccagttc aacaacaccg ccagagagct ggactgcatc   1620
aagatcaccc agcaggtggg cgtggagctg aacctgtacc tgaccgagct gaccacagtg   1680
ttcggccccc agatcacaag cccagccctg acacagctga ccatccaggc cctgtacaac   1740
ctggctggcg gcaacatgga ctatctgctg acaaagctgg gaatcggcaa caaccagctg   1800
tccagcctga tcggaagcgg cctgatcacc ggctaccccca tcctgtacga cagccagaca   1860
cagctgctgg gcatccaggt gaacctgccc agcgtgggca acctgaacaa catgcgcgcc   1920
acctacctgg aaaccctgag cgtgtccacc accaagggct acgccagcgc cctggtgccc   1980
aaggtggtga cacaggtggg cagcgtgatc gaggaactgg acaccagcta ctgcatcgag   2040
agcgacctgg acctgtactg caccagaatc gtgaccttcc caatgagccc cggcatctac   2100
agctgcctga gcggcaacac cagcgcctgc atgtacagca agaccgaagg cgcactgaca   2160
acaccctaca tggccctgaa gggaagcgtg atcgccaact gcaagatcac cacctgcaga   2220
tgcaccgacc ccccaggcat catcagccag aactacggcg aggccgtgag cctgatcgat   2280
cgccattcct gtaacgtgct gtccctggac ggcatcacac tgagactgag cggcgagttc   2340
gatgccacct accagaagaa catcagcatc ctggacagcc aggtgatcgt gaccggcaac   2400
ctggacatca gcaccgagct gggcaacgtg aataacagca tcagcaacgc cctggacaga   2460
ctggccgaga gcaacagcaa gctggaaaaa gtgaacgtgc gcctgacatc cacttccgct   2520
ctgatcacct acatcgtgct gaccgtgatc agcctggtgt tcggcgccct gagcctggtg   2580
ctggcctgct acctgatgta caagcagaag gcccagcaga aaaccctgct gtggctgggc   2640
aacaacaccc tggaccagat gagagccacc accagagcct gatgagcggc cgccccgggc   2700
ctgcaggcat aggcacgctc tgatgttaca gaccacaata ccgcatacat ttattgtaag   2760
gttgttaata aaggtttatt ctatgtaaga ctacaatact ttcgacattg cttgtataca   2820
```

```
tattaaatac tttctcaagt tcctattaca taaaatggga tctatcatta cattcgttaa    2880
gagtctggat aattttactg tttgccagct tcgatcttgg aacgtactgt ggatagtgcc    2940
ttacttggaa tcgtgaaaat ttgaaacgtc cattatttgg atatcttccg gttgtcccat    3000
atcccgccct ggtaccgctc ggataccttg cccgtatgga ttcgtattga cagtcgcgca    3060
atcggggacc aacaacgcgt gggtccacac tcattcggaa attttccgat gattctgaat    3120
atttattgcc gctcgttacg agtcgttgga catatctgta atacatttct tcttctgaag    3180
gatcgctgca catttgatct atacattggc caggatgttc aagtctcaga tgttgcattc    3240
tggcacagca caactttatg gcatttccga tgtaatcgtc cggcagccct gggggagttc    3300
tatattcgca tattgggatg gtaaggacaa tagcagatct cgcaacctcc agggaggcta    3360
taataacgtt tttaaaggat ggattctcta taaaaatctg tcgcaaatta cactgagaat    3420
atcctttact agcgccgatt gagagcatcg tcgtccaatt ttctaaatgg aaagaaaaca    3480
aggcgggcaa gagtgttcca acatttttca ttttcggcga atctctcaaa tcccatggcg    3540
tgcaattgat tgcaaaattg gcacttccgt tcacgtttgt atctccaaac tctaagacac    3600
ttttaattga aaaactacgt tctagtgtgg aagaaacct ataggcagac catagaacta    3660
tttgacacca catatctttt tgtatgtcaa actgaccatg atcgtat                 3707

<210> SEQ ID NO 26
<211> LENGTH: 3707
<212> TYPE: DNA
<213> ORGANISM: artificial sequence
<220> FEATURE:
<223> OTHER INFORMATION: Partial plasmid pHVT US20 cds F CA02 opt
      sequence for vHVT303

<400> SEQUENCE: 26
tcccttacgg cggatcga

```
ggcatcgtgg tgaccggcga caaggccgtg aacatctaca ccagcagcca gaccggcagc    1200
atcatcatca agctgctgcc caacatgccc aaggacaaag aggcctgcgc caaggccccc    1260
ctggaagcct acaacagaac cctgaccacc ctgctgaccc ccctgggcga cagcatcaga    1320
agaatccagg gcagcgccac cacaagcggc ggaggaaagc agggcagact ggtgggcgct    1380
atcatcggga gcgtggccct gggcgtggcc acagctgccc agattaccgc tgcagccgcc    1440
ctgattcagg ccaatcagaa cgccgccaac atcctgagac tgaaagagag cattgccgcc    1500
accaacgacg ccgtgcacga agtgacaaac ggactgtccc agctggctgt cgctgtcggc    1560
aagatgcagc agttcgtgaa caaccagttc aacaacaccg ccagagagct ggactgcatc    1620
aagatcgccc agcaggtggg cgtggagctg aacctgtacc tgaccgagct gaccacagtg    1680 ttcggcccc agatcacaag ccccgctctg acccagctga caatccaggc cctgtacaac    1740
ctggctggcg gcaacatgga ctatctgctg actaagctgg gagtgggcaa caaccagctg    1800
tccagcctga tcgggtccgg gctgatcaca ggcaaccca tcctgtacga cagccagaca    1860
cagctgctgg gcatccagat caacctgcca tccgtgggaa gcctgaacaa catgagagcc    1920
acctacctgg aaaccctgag cgtgtccacc accaagggct cgccagcgc cctggtgccc    1980 aaggtggtga cacaggtggg cagcgtgatc gaggaactgg acaccagcta ctgcatcgag    2040
agcgacatcg acctgtactg caccagagtg gtgaccttcc caatgagccc cggcatctac    2100
agctgcctga gcggcaacac cagcgcctgc atgtacagca gaccgaagg agcactgaca    2160 acaccctaca tggccctgaa gggaagcgtg atcgccaact gcaagatgac cacctgcaga    2220
tgcgccgacc ccccaggcat catcagccag aactacggcg aggccgtgag cctgatcgac    2280
aaacattcct gtagcgtgct gtccctggat ggcatcacac tgagactgag cggcgagttc    2340
gacgccacct accagaagaa catcagcatc ctggacagcc aggtgatcgt gaccggcaac    2400
ctggacatca gcaccgagct gggcaacgtg aacaacagca tcagcagcac cctggacaag    2460
ctggccgagt ccaacaacaa gctgaacaaa gtgaacgtga acctgaccag cacaagcgcc    2520
ctgatcacct acatcgtgct ggccatcgtg tccctggcct tcggcgtgat cagcctggtg    2580
ctggcctgct acctgatgta caagcagaga gcccagcaga aaccctgct gtggctgggc    2640 aataacaccc tggaccagat gagggccacc accagaacct gatgagcggc cgccccgggc    2700
ctgcaggcat aggcacgctc tgatgttaca gaccacaata ccgcatacat ttattgtaag    2760
gttgttaata aaggtttatt ctatgtaaga ctacaatact ttcgacattg cttgtataca    2820
tattaaatac tttctcaagt tcctattaca taaaatggga tctatcatta cattcgttaa    2880
gagtctggat aattttactg tttgccagct tcgatcttgg aacgtactgt ggatagtgcc    2940
ttacttggaa tcgtgaaaat ttgaaacgtc cattatttgg atatcttccg gttgtcccat    3000
atcccgccct ggtaccgctc ggataccttg cccgtatgga ttcgtattga cagtcgcgca    3060
atcggggacc aacaacgcgt gggtccacac tcattcggaa attttccgat gattctgaat    3120
atttattgcc gctcgttacg agtcgttgga catatctgta atacatttct tcttctgaag    3180
gatcgctgca catttgatct atacattggc caggatgttc aagtctcaga tgttgcattc    3240
tggcacagca caactttatg gcatttccga tgtaatcgtc cggcagccct gggggagttc    3300
tatattcgca tattgggatg gtaaggacaa tagcagatct cgcaacctcc agggaggcta    3360
taataacgtt tttaaaggat ggatttctca taaaaatctg tcgcaaatta cactgagaat    3420
atcctttact agcgccgatt gagagcatcg tcgtccaatt ttctaaatgg aaagaaaaca    3480
```

| | |
|---|---|
| aggcgggcaa gagtgttcca aacattttca ttttcggcga atctctcaaa tcccatggcg | 3540 |
| tgcaattgat tgcaaaattg gcacttccgt tcacgtttgt atctccaaac tctaagacac | 3600 |
| ttttaattga aaaactacgt tctagtgtgg aaagaaacct ataggcagac catagaacta | 3660 |
| tttgacacca catatctttt tgtatgtcaa actgaccatg atcgtat | 3707 |

<210> SEQ ID NO 27
<211> LENGTH: 3946
<212> TYPE: DNA
<213> ORGANISM: artificial sequence
<220> FEATURE:
<223> OTHER INFORMATION: Partial plasmid HVT IG2 SVFopt syn tail
      sequence for vHVT304

<400> SEQUENCE: 27

| | |
|---|---|
| tgtttcgcac catatccaag ctggctgtcc ctaagagctt attcctgcaa gacctcatac | 60 |
| ggataattg cccgaccaat acttattacg gacataggta ggccgataaa tattatgttg | 120 |
| actggaggat ggaaaggagg ttttgtaaca gctacatcgc tcgttcatca gcaagcgata | 180 |
| ctttggatat ccgagcttca aaagccgcat aaaccccgct ttatttctga atacgcccca | 240 |
| acagtaacac atgcgtggtt cctggcactt ggaacgccgt gttttatagg caagaacata | 300 |
| ctacccaaag aggtcttggg atttctggcg cgtcgttgca atgaagaaat gaattctttg | 360 |
| ttccttgaaa tgccgacaac tctaaaaacg gtattcgagc accattactt tacgcgtgga | 420 |
| tctgaagtaa atccagcgtt gttgatggag cctaacagat ttttgcaact gatggattcg | 480 |
| cggaaaatcc tatgtttata cgaatccgct atgtgcgaca ccccggagc tcagggtatg | 540 |
| atactcagct gttattgtgg ccgaccagga ggactccaat gcttagcatt cataagaacg | 600 |
| ctagagatgc tatttaacga tgtgctgtcg tctaaagaat ttgtgcattt agcctttaaa | 660 |
| tgtaaaacca atgacgcatt cactacgctc gtgcgtgcaa tttctgggcc agggtatgca | 720 |
| tattccataa cagaaatcga cacttgagaa gaggatctga ctgtttggga taaaggtcgt | 780 |
| ttgggtctgt cctagcgata taatttatat gacgatatac attaaacatc tgtgtgcagt | 840 |
| acttaggtat ttaatcatgt cgatgaaatg ttatgtgtaa atatcggaca atatagataa | 900 |
| cgggcacgct gctattgtaa cgtgcgcccg cgcgctagtg ctgactaata gtgtggatga | 960 |
| tgtatacagt atattacaaa cggaaatgat acgtaataaa cctgcaggtc gacccaattc | 1020 |
| gagctcggta cagcttggct gtggaatgtg tgtcagttag ggtgtggaaa gtccccaggc | 1080 |
| tccccagcag gcagaagtat gcaaagcatg catctcaatt agtcagcaac caggtgtgga | 1140 |
| aagtccccag gctccccagc aggcagaagt atgcaaagca tgcatctcaa ttagtcagca | 1200 |
| accatagtcc cgcccctaac tccgcccatc ccgccctaa ctccgcccag ttccgcccat | 1260 |
| tctccgcccc atggctgact aattttttt atttatgcag aggccgaggc cgcctcggcc | 1320 |
| tctgagctat tccagaagta gtgaggaggc ttttttggag gcctaggctt ttgcaaaaag | 1380 |
| ctcccgggc ggccgccacc atgggcagca agcccagcac aagaatccca gcccccctga | 1440 |
| tgctgatcac ccgcatcatg ctgatcctgg gctgcatcag cccacaagc tccctggatg | 1500 |
| gacgccccct ggccgctgcc ggcatcgtgg tgaccggcga caaggccgtg aacgtgtaca | 1560 |
| ccagcagcca gaccggcagc atcatcgtga agctgctgcc caacatgccc agagacaaag | 1620 |
| aggcctgcgc caaggccccc ctggaagcct acaacagaac cctgaccacc ctgctgaccc | 1680 |
| ccctgggcga cagcatcaga aagatccagg gctccgtgag cacaagcggc ggaggaaagc | 1740 |
| agggcagact gatcggcgcc gtgatcggca gcgtggcect gggagtggct acagctgccc | 1800 |

| | |
|---|---|
| agattaccgc tgcagccgcc ctgatccagg ccaaccagaa cgccgccaac atcctgagac | 1860 |
| tgaaagagag cattgccgcc accaacgagg ccgtgcacga agtgaccgac ggcctgagcc | 1920 |
| agctgtccgt ggccgtgggc aagatgcagc agttcgtgaa cgaccagttc aacaacaccg | 1980 |
| ccagagagct ggactgcatc aagatcaccc agcaggtggg cgtggagctg aacctgtacc | 2040 |
| tgaccgagct gaccacagtg ttcggccccc agatcacaag cccagccctg acacagctga | 2100 |
| ccatccaggc cctgtacaac ctggctggcg gcaacatgga ctatctgctg acaaagctgg | 2160 |
| gaatcggcaa caaccagctg tccagcctga tcggaagcgg cctgatcacc ggctacccca | 2220 |
| tcctgtacga cagccagaca cagctgctgg gcatccaggt gaacctgccc agcgtgggca | 2280 |
| acctgaacaa catgcgcgcc acctacctgg aaaccctgag cgtgtccacc accaagggct | 2340 |
| acgccagcgc cctggtgccc aaggtggtga cacaggtggg cagcgtgatc gaggaactgg | 2400 |
| acaccagcta ctgcatcgag agcgacctgg acctgtactg caccagaatc gtgaccttcc | 2460 |
| caatgagccc cggcatctac agctgcctga gcggcaacac cagcgcctgc atgtacagca | 2520 |
| agaccgaagg cgcactgaca cacccctaca tggcccctgaa gggaagcgtg atcgccaact | 2580 |
| gcaagatcac cacctgcaga tgcaccgacc cccaggcat catcagccag aactacggcg | 2640 |
| aggccgtgag cctgatcgat cgccattcct gtaacgtgct gtccctggac ggcatcacac | 2700 |
| tgagactgag cggcgagttc gatgccacct accagaagaa catcagcatc ctggacagcc | 2760 |
| aggtgatcgt gaccggcaac ctggacatca gcaccgagct gggcaacgtg aataacagca | 2820 |
| tcagcaacgc cctggacaga ctggccgaga gcaacagcaa gctggaaaaa gtgaacgtgc | 2880 |
| gcctgacatc cacttccgct ctgatcacct acatcgtgct gaccgtgatc agcctggtgt | 2940 |
| tcggcgccct gagcctggtg ctggcctgct acctgatgta caagcagaag gcccagcaga | 3000 |
| aaaccctgct gtggctgggc aacaaccccc tggaccagat gagagccacc accagagcct | 3060 |
| gatgagcggc cgcgatatca ataaaatatc tttatttttca ttacatctgt gtgttggttt | 3120 |
| tttgtgtgaa tcgatagtac taacatacgc tctccatcaa aacaaaacga aacaaaacaa | 3180 |
| actagcaaaa taggctgtcc ccagtgcaag tgcaggtgcc agaacatttc tcttctagac | 3240 |
| ctgcaggtta tgtactctta ttgatttata aaaacataca tgcagtgttg ctatgtcaca | 3300 |
| taattagcct cgcccgtcta cgctccactg aagataatgg gctcccgctg ttcaaaaaaa | 3360 |
| tcagcgtgcg tcgataagac tttggtgcag tctcttcggg gtcgcaattt agatttgccg | 3420 |
| catggagggt atctggggat ttttgccaat gctggagcga cgactgtacg attcgtccca | 3480 |
| tcgggatcta gcagaccaat gatgttgaca cacatcggcc atgcatgtac ggacggtcta | 3540 |
| ttgcgcgagt ttgttatttt cgaaggacaa gatggaagtg tatatggaac cgacaataat | 3600 |
| gttagtttgc atttcttagg gcggaatcta catgatatct tatccaagcg gggtatgagc | 3660 |
| cagagagatg tgatggtcat aaagggtaaa tttttagat ctgaaataac gcagttgccc | 3720 |
| aaacaacgat cgcgattaaa agaaaaatcg gatggttcaa ttaggacatg catgatttct | 3780 |
| gtgcgcataa accataaccg cagcactgtt gggcacttcg gtaactcaaa tgcgaagcgt | 3840 |
| tgcacgtctg cgataactac gcctactatg cacattgtta ctcctgcatc ttaaaaatat | 3900 |
| atcctgtagt aatttttcaca gcaatgtcat aacatcatct cgctaa | 3946 |

<210> SEQ ID NO 28
<211> LENGTH: 4654
<212> TYPE: DNA
<213> ORGANISM: artificial sequence
<220> FEATURE:
<223> OTHER INFORMATION: Partial plasmid pHVT US2 SV-FCA02 opt-synPA for vHVT307

<400> SEQUENCE: 28

```
tatctccaca tcgtattcag gcccacggaa gtcttcgtta tcgaagctat tgttactagt    60
atctggcgac atcgacggtt ctgcaaccgt cgtaccgctt tcgatatttt cacagacaat   120
acccatattc gaggcactta ctttcgaaga ctcaacatct acttccatcg ccgccacgta   180
tgtaatttcg ggacgttgga tgatataaaa tatatagtac gcgtccgggt atacacctgt   240
gcgaaagtag tacgagaccg gcagtcaaaa agacgtttcc gatcttccac agctccagtt   300
attcggaagg cgtgggcatg ggtgtgtgca tgataactct cgtcacttta ctagacgaat   360
gcgatcgatt gcctgggcga tctcgtgacg ctgcctccac cctatggatc tttctcatag   420
aacaatgcat ggagcatctg aagaatgatg tgggtgtgcc catattagtc cgtacagcag   480
acctgtgtcg gtttgccaaa tccacattcg ttttgccccg ccggcatcgc ccaattgtga   540
gaattaaatc ggcaggcggg agtggtatgc ccggttccgg attggcagga acgagagatg   600
catttattgt gagactgttt gaagatgtag ccggttgcgc taccgaatgg caggatctac   660
tgaccggcta tgtaatgcta gaatcggagg cctccgataa cgtatcgtat agcctgtgga   720
tactcggggc tgcagatatc tgcagaactg caatagaatc aatacctcta ccaaaacgtt   780
tgtttgccat taaagtacca ggcacctggg ctggaatgcc ttgggccatt ccatgtgaga   840
tacaaacact tctcacgtcc acttgggaac ctaaatttga aaacatagaa gataaggcgt   900
acttcaacga cagtaatatg gcgtgcgtat atcaaattat cggctctcca ccagacgttc   960
cccagctgca ggggcttggt atcgagtcca catgcacccc acctaaacgc aatttgtgtt  1020
gctgcctatg ttgccgtcca atacatgacg acgacgcctc cgttcccatg ggcgttaaga  1080
cagtagataa aaacgtacat gatggcaata tgcttgtaga ggctcccaag tgtatcacag  1140
ataggggaaa attcaatagt agataaaccc aactagtgtg aggaaattgc atctacttgc  1200
ccccgggcct gcaggtcgac ccaattcgag ctcggtacag cttggctgtg aatgtgtgt  1260
cagttagggt gtggaaagtc cccaggctcc ccagcaggca gaagtatgca aagcatgcat  1320
ctcaattagt cagcaaccag gtgtggaaag tccccaggct cccagcagg cagaagtatg  1380
caaagcatgc atctcaatta gtcagcaacc atagtcccgc ccctaactcc gcccatcccg  1440
cccctaactc cgcccagttc cgcccattct ccgcccatg gctgactaat ttttttatt   1500
tatgcagagg ccgaggccgc ctcggcctct gagctattcc agaagtagtg aggaggcttt  1560
tttggaggcc taggctttg caaaaagctc ccggggcggc cgccaccatg gcagcaagc   1620
ccagcacctg gatcagcgtg accctgatgc tgatcaccag aaccatgctg atcctgagct  1680
gcatctgccc cacaagcagc ctggacggca gacccctggc cgctgccggc atcgtggtga  1740
ccggcgacaa ggccgtgaac atctacacca gcagccagac cggcagcatc atcatcaagc  1800
tgctgcccaa catgcccaag gacaaagagg cctgcgccaa gggcccctg gaagcctaca  1860
acagaaccct gaccaccctg ctgacccccc tgggcgacag catcagaaga tccagggca  1920
gcgccaccac aagcggcgga ggaaagcagg gcagactggt gggcgctatc atcgggagcg  1980
tggccctggg cgtggcccac actgcccaga ttaccgctgc agccgccctg attcaggca   2040
atcagaacgc cgccaacatc ctgagactga aagagagcat tgccgccacc aacgacgccg  2100
tgcacgaagt gacaaacgga ctgtcccagc tggctgtcgc tgtcggcaag atgcagcagt  2160
tcgtgaacaa ccagttcaac aacaccgcca gagagctgga ctgcatcaag atcgcccagc  2220
aggtgggcgt ggagctgaac ctgtacctga ccgagctgac cacagtgttc ggcccccaga  2280
```

```
tcacaagccc cgctctgacc cagctgacaa tccaggccct gtacaacctg gctggcggca    2340
acatggacta tctgctgact aagctgggag tgggcaacaa ccagctgtcc agcctgatcg    2400
ggtccgggct gatcacaggc aaccccatcc tgtacgacag ccagacacag ctgctgggca    2460
tccagatcaa cctgccatcc gtgggaagcc tgaacaacat gagagccacc tacctggaaa    2520
ccctgagcgt gtccaccacc aagggcttcg ccagcgccct ggtgcccaag gtggtgacac    2580
aggtgggcag cgtgatcgag gaactggaca ccagctactg catcgagagc gacatcgacc    2640
tgtactgcac cagagtggtg accttcccaa tgagccccgg catctacagc tgcctgagcg    2700
gcaacaccag cgcctgcatg tacagcaaga ccgaaggagc actgacaaca ccctacatgg    2760
ccctgaaggg aagcgtgatc gccaactgca agatgaccac ctgcagatgc gccgaccccc    2820
caggcatcat cagccagaac tacggcgagg ccgtgagcct gatcgacaaa cattcctgta    2880
gcgtgctgtc cctggatggc atcacactga gactgagcgg cgagttcgac gccacctacc    2940
agaagaacat cagcatcctg gacagccagg tgatcgtgac cggcaacctg gacatcagca    3000
ccgagctggg caacgtgaac aacagcatca gcagcaccct ggacaagctg gccgagtcca    3060
acaacaagct gaacaaagtg aacgtgaacc tgaccagcac aagcgccctg atcacctaca    3120
tcgtgctggc catcgtgtcc ctggccttcg gcgtgatcag cctggtgctg gcctgctacc    3180
tgatgtacaa gcagagagcc cagcagaaaa ccctgctgtg gctgggcaat aacaccctgg    3240
accagatgag ggccaccacc agaacctgat gagcggccgc gatatcaata aaatatcttt    3300
attttcatta catctgtgtg ttggttttttt gtgtgaatcg atagtactaa catacgctct    3360
ccatcaaaac aaaacgaaac aaaacaaact agcaaaatag gctgtcccca gtgcaagtgc    3420
aggtgccaga acatttctct tctagacctg caggcatatg ttgtcccatt atgttgtaca    3480
taatcgtgat gtagtgctac gcaaatgtca attgatagcc catacatggt gctaatatgc    3540 gttacttta gtatgtgagt gaataaaaaa atattacccc tatgatacct gcgtctttat    3600
gctacaagtt ccttcaccat gaccagagcc ggtgcgatca tattcgacaa cttggatatt    3660
cccagaggta gatttggcca gccgcgggga aaaataaatg acttcaacta ctggaccttg    3720
ctaaccgatg agctgacgtg tggaattatt caatgtatgg agtcgcgcga gcgaattgcc    3780
ctagtgcatt cagcaacata cgatcatggt cagtttgaca tacaaaaaga tatgtggtgt    3840
caaatagttc tatggtctgc ctataggttt ctttccacac tagaacgtag tttttcaatt    3900
aaaagtgtct tagagtttgg agatacaaac gtgaacggaa gtgccaattt tgcaatcaat    3960
tgcacgccat gggatttgag agattcgccg aaaatgaaaa tgtttggaac actcttgccc    4020
gccttgtttt ctttccattt agaaaattgg acgacgatgc tctcaatcgg cgctagtaaa    4080
ggatattctc agtgtaattt gcgacagatt tttatgagaa atccatcctt taaaaacgtt    4140
attatagcct ccctggaggt tgcgagatct gctattgtcc ttaccatccc aatatgcgaa    4200
tatagaactc ccccagggct gccggacgat tacatcggaa atgccataaa gttgtgctgt    4260
gccagaatgc aacatctgag acttgaacat cctggccaat gtatagatca aatgtgcagc    4320
gatccttcag aagaagaaat gtattacaga tatgtccaac gactcgtaac gagcggcaat    4380
aaatattcag aatcatcgga aaatttccga atgagtgtgg acccacgcgt tgttggtccc    4440
cgattgcgcg actgtcaata cgaatccata cgggcaaggt atccgagcgg taccagggcg    4500
ggatatggga caaccggaag atatccaaat aatggacgtt tcaaattttc acgattccaa    4560
gtaaggcact atccacagta cgttccaaga tcgaagctgg caaacagtaa aattatccag    4620
```
actcttaacg aatgtaatga tagatcccat ttta 4654

<210> SEQ ID NO 29
<211> LENGTH: 5381
<212> TYPE: DNA
<213> ORGANISM: artificial sequence
<220> FEATURE:
<223> OTHER INFORMATION: partial plasmid pCD046+NDV-F VII YZCQ sequence for HVT112

<400> SEQUENCE: 29
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960
gattaaaaga aaaatcggat ggttcaatta ggacatgcat ggattctgtg cgcataaacc 1020
ataaccgcag cactgttggg cacttcggta actcaaatgc gaagcgttgc acgtctgcga 1080
taactacgcc tactatgcac attgttactc ctgcatctta aaaatatatc ctgtagtaat 1140
tttcacagca atgtcataac atcatctcgc taaagaatga cctgggattg gagaagtaat 1200
gaatatttgc aaccaatgca ttgaataaac taacattaaa cgaattcaat agtggatccc 1260
ccaactccgc ccgttttatg actagaacca atagtttta atgccaaatg cactgaaatc 1320
ccctaatttg caaagccaaa cgccccctat gtgagtaata cggggacttt ttacccaatt 1380
tcccacgcgg aaagcccct aatacactca tatggcatat gaatcagcac ggtcatgcac 1440
tctaatggcg gcccataggg actttccaca tagggggcgt tcaccatttc ccagcatagg 1500
ggtggtgact caatggcctt tacccaagta cattgggtca atgggaggta agccaatggg 1560
tttttcccat tactggcaag cacactgagt caaatgggac tttccactgg gttttgccca 1620
agtacattgg gtcaatggga ggtgagccaa tgggaaaaac ccattgctgc caagtacact 1680
gactcaatag ggactttcca atgggttttt ccattgttgg caagcatata aggtcaatgt 1740
gggtgagtca atagggactt tccattgtat tctgcccagt acataaggtc aatagggggt 1800
gaatcaacag gaaagtccca ttggagccaa gtacactgcg tcaataggga ctttccattg 1860
ggttttgccc agtacataag gtcaataggg gatgagtcaa tgggaaaaac ccattggagc 1920
caagtacact gactcaatag ggactttcca ttgggttttg cccagtacat aaggtcaata 1980

-continued

```
gggggtgagt caacaggaaa gttccattgg agccaagtac attgagtcaa tagggacttt    2040
ccaatgggtt ttgcccagta cataaggtca atgggaggta agccaatggg ttttcccat     2100 tactggcacg tatactgagt cattagggac tttccaatgg gttttgccca gtacataagg    2160
tcaatagggg tgaatcaaca ggaaagtccc attggagcca agtacactga gtcaataggg    2220
actttccatt gggttttgcc cagtacaaaa ggtcaatagg gggtgagtca atgggttttt    2280
cccattattg gcacgtacat aaggtcaata ggggtgagtc attgggtttt tccagccaat    2340
ttaattaaaa cgccatgtac tttcccacca ttgacgtcaa tgggctattg aaactaatgc    2400
aacgtgacct ttaaacggta ctttcccata gctgattaat gggaaagtac cgttctcgag    2460
ccaatacacg tcaatgggaa gtgaaagggc agccaaaacg taacaccgcc ccggttttcc    2520
cctggaaatt ccatattggc acgcattcta ttggctgagc tgcgttctac gtgggtataa    2580
gaggcgcgac cagcgtcggt accgtcgcag tcttcggtct gaccaccgta gaacgcagag    2640
ctcctcgctg caggcggccg catgggctct aaaccttcta ccaggatccc agcacctctg    2700
atgctgatca cccggattat gctgatattg gactgtatcc gtccgacaag ctctcttgac    2760
ggcaggcctc ttgcagctgc aggaattgta gtaacaggag ataaggcagt caatgtatat    2820
acctcgtctc agacagggtc aatcatagtc aagttgctcc cgaatatgcc caaggataag    2880
gaggcgtgtg cgaaagaccc attagaggca tataacagaa cactgactac tttgctcact    2940
cctcttggcg aatccatccg caagatccaa gggtctgtgt ccacgtctgg aggaggcaag    3000
caaggccgcc tgataggtgc tgttattggt agtgtagctc ttggggttgc aacagcggca    3060
caaataacag cagctgcggc cctaatacaa gccaaccaga atgctgccaa catccttcgg    3120
cttaaggaga gcattgctgc aaccaatgaa gctgtgcatg aagtcaccga cggattatca    3180
caactatcag tggcagttgg gaagatgcag cagtttgtca atgaccagtt taataataca    3240
gcgcgagaat tggactgtat aaaaatcaca caacaggttg gtgtagaact caacctatac    3300
ctaactgaat tgactacagt attcgggcca cagatcacct cccctgcatt aactcagctg    3360
accatccagg cactttataa tttagctggt ggcaatatgg attacttatt aactaagtta    3420
ggtataggga caatcaact cagctcatta attggcagcg gcctgatcac tggttaccct    3480
atattgtatg actcacagac tcaactcttg gcatacaag tgaatttgcc ctcagtcggg    3540
aacttaaata atatgcgtgc cacctattta gagaccttat ctgtaagtac agccaaagga    3600
tatgcctcag cacttgttcc aaaagtagtg acacaagtcg gttctgtgat agaagagctt    3660
gacacctcat actgtatcga gtccgatctg gatttatatt gtactagaat agtgacattc    3720
cccatgtccc caggtattta ttcctgttta agcggcaaca catcagcttg catgtattca    3780
aagactgaag gcgcactcac tacgccgtat atggccctta aaggctcagt tattgccaat    3840
tgtaagataa caacatgtag atgtacagac cctcctggta tcatatcgca aaattatgga    3900
gaagctgtat ccctgatgga tagacattcg tgcaatgtct tatcattaga cgggataact    3960
ctgaggctca gtggagaatt tgatgcaact tatcaaaaga acatctcaat actagattct    4020
caagtcatcg tgacaggcaa tcttgatata tcaactgaac ttggaaacgt caacaattca    4080
atcagcaatg ccttggataa gttggcaaaa gcaacagca agctagaaaa agtcaatgtc    4140
agactaacca gcacatccgc tctcattacc tatattgttc tgactgtcat ttctctagtt    4200
ttcggtgcac taagtctggg tttaacatgt tacctgatgt acaaacaaaa ggcacaacaa    4260
aagaccttgc tatggcttgg gaataatacc ctcgatcaga tgagagccac tacaagagca    4320
tgagcggccg cggggatcca gacatgataa gatacattga tgagtttgga caaaccacaa    4380
```

```
ctagaatgca gtgaaaaaaa tgctttattt gtgaaatttg tgatgctatt gctttatttg    4440
taaccattat aagctgcaat aaacaagtta acaacaacaa ttgcattgat tttatgtttc    4500
aggttcaggg ggaggtgtgg gaggttttttt cggatcctct agagtcgaca attattttat   4560
ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata cccctctat    4740 attcatggta taattatcgt ctacagcgtc caggatagtg gcgtgagaaa atggagatct    4800
gcagccctcc tttccatggc atgccgcttt attgttcatt aaacgcacaa tggtctcaac    4860
gccagatatg gcatagatt ctgaagaacc cgttgacaat ccgaagaaga aggcgtgcag     4920
gtctttggaa gactcgcacg ttggtcttat aatgtatgat cgagatgtca ccctaatgcc    4980
acatggtaca ggcttatcgc ggtcatggcg atcggacttg taatttgcaa cgatgggcaa    5040
aggatcgacg acatgccaaa cattctgaac ccgtagagat gttaacgatg acgaggatga    5100
atatcccatg ctcgctgcca tagtatcaag tacaccgcga ataaggacgc gtccaacatc    5160
gttatatgca cacaatgggc tacacgtgac taacacccccc gaatattagt catatgtgag   5220
tttcagtctg gctcccatat agcctgtaga ctatttgtgg tttaagtgtg aacgaggcgc    5280
tgtgaacgag actcgggccg attgtaagaa caagcaaatg cactttccat ttaacaagaa    5340
gtgtagagag aatactcaac ctctttggat gtatcctcga g                        5381
```

<210> SEQ ID NO 30
<211> LENGTH: 5381
<212> TYPE: DNA
<213> ORGANISM: artificial sequence
<220> FEATURE:
<223> OTHER INFORMATION: partial plasmid pCD046+Texas NDV-F sequence for HVT113

<400> SEQUENCE: 30

```
gagctcaggg tatgatactc agctgttatt gtggccgacc aggaggactc caatgcttag     60
cattcataag aacgctagag atgctatta acgatgtgct gtcgtctaaa gaatttgtgc    120
atttagcctt taaatgtaaa accaatgacg cattcactac gctcgtgcgt gcaatttctg    180
ggccagggta tgcatattcc ataacagaaa tcgacacttg agaagaggat ctgactgttt    240
gggataaagg tcgtttgggt ctgtcctagc gatataattt atatgacgat atacattaaa    300
catctgtgtg cagtacttag gtatttaatc atgtcgatga atgttatgt gtaaatatcg    360 gacaatatag ataacgggca cgctgctatt gtaacgtgcg cccgcgcgct agtgctgact    420
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660 tggggattt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
```

```
ataaccgcag cactgttggg cacttcggta actcaaatgc gaagcgttgc acgtctgcga    1080
taactacgcc tactatgcac attgttactc ctgcatctta aaaatatatc ctgtagtaat    1140
tttcacagca atgtcataac atcatctcgc taaagaatga cctgggattg agaagtaat    1200
gaatatttgc aaccaatgca ttgaataaac taacattaaa cgaattcaat agtggatccc    1260
ccaactccgc ccgttttatg actagaacca atagttttta atgccaaatg cactgaaatc    1320
ccctaatttg caaagccaaa cgcccctat gtgagtaata cggggacttt tacccaatt    1380
tcccacgcgg aaagccccct aatacactca tatggcatat gaatcagcac ggtcatgcac    1440
tctaatggcg gcccataggg actttccaca tagggggcgt tcaccatttc ccagcatagg    1500
ggtggtgact caatggcctt tacccaagta cattgggtca atgggaggta agccaatggg    1560
tttttcccat tactggcaag cacactgagt caaatgggac tttccactgg gttttgccca    1620
agtacattgg gtcaatggga ggtgagccaa tgggaaaaac ccattgctgc caagtacact    1680
gactcaatag ggactttcca atgggttttt ccattgttgg caagcatata aggtcaatgt    1740
gggtgagtca atagggactt tccattgtat tctgcccagt acataaggtc aataggggt    1800
gaatcaacag gaaagtccca ttggagccaa gtacactgcg tcaatagggea ctttccattg    1860
ggttttgccc agtacataag gtcaataggg gatgagtcaa tgggaaaaac ccattggagc    1920
caagtacact gactcaatag ggactttcca ttgggttttg cccagtacat aaggtcaata    1980
ggggtgagt caacaggaaa gttccattgg agccaagtac attgagtcaa tagggacttt    2040
ccaatgggtt ttgcccagta cataaggtca atggaggta agccaatggg ttttcccat    2100
tactggcacg tatactgagt cattagggac tttccaatgg gttttgccca gtacataagg    2160
tcaataggg tgaatcaaca ggaaagtccc attggagcca agtacactga gtcaatagg    2220
actttccatt gggttttgcc cagtacaaaa ggtcaatagg gggtgagtca atgggttttt    2280
cccattattg gcacgtacat aaggtcaata ggggtgagtc attgggtttt tccagccaat    2340
ttaattaaaa cgccatgtac tttcccacca ttgacgtcaa tgggctattg aaactaatgc    2400
aacgtgacct ttaaacggta ctttcccata gctgattaat gggaaagtac cgttctcgag    2460
ccaatacacg tcaatgggaa gtgaaagggc agccaaaacg taacaccgcc ccggttttcc    2520
cctgaaatt ccatattggc acgcattcta ttggctgagc tgcgttctac gtgggtataa    2580
gaggcgcgac cagcgtcggt accgtcgcag tcttcggtct gaccaccgta gaacgcagag    2640
ctcctcgctg caggcggccg catgggctcc agatcttcta ccaggatccc ggtacctcta    2700
atgctgatca tccgaaccgc gctgacactg agctgtatcc gtctgacaag ctctcttgat    2760
ggcaggcctc ttgcggctgc agggatcgtg gtaacaggag ataaagcagt caacatatac    2820
acctcatccc agacagggtc aatcatagtt aagttactcc cgaatatgcc caaggacaaa    2880
gaggtgtgtg caaaagcccc attggaggca tacaacagga cactgactac tttactcacc    2940
ccccttggtg attctatccg caggatacaa gagtctgtga ctacttccgg aggaggcaag    3000
caaggccgcc tgataggtgc cattatcggc agtgtagctc ttgggggttgc gacagctgca    3060
cagataacag cagcttcggc cctgatacaa gccaaccaga atgctgccaa catcctccgg    3120
cttaaagaga gcattgctgc aaccaatgaa gctgtgcacg aggtcactga cggattatca    3180
caactagcag tggcagtagg aagatgcaa cagtttgtca atgaccagtt caataataca    3240
gcgcaagaat tggactgtat aaaaattgca cagcaggtcg gtgtagaact caacttgtac    3300
ctaactgaat tgactacagt atttgggcca caaatcactt cccctgcctt aactcagctg    3360
```

-continued

| | |
|---|---|
| actatccaag cgctttacaa tctagctggt ggtaatatgg attacttgct gactaagtta | 3420 |
| ggtgtaggga caaccaact cagctcatta attggtagcg gcttgatcac cggcaaccct | 3480 |
| attctgtacg actcacagac tcagatcttg ggtatacagg taactttgcc ttcagttggg | 3540 |
| aacctgaata atatgcgtgc cacctacctg gagaccttat ctgtaagcac aaccaaggga | 3600 |
| tttgcctcag cacttgtccc aaaagtggtg acacaggtcg gttccgtgat agaagaactt | 3660 |
| gacacctcat actgtatagg gaccgacttg gatttatact gtacaagaat agtgacattc | 3720 |
| cctatgtctc ctggtattta ttcttgtctg agcggtaata catcggcttg catgtattca | 3780 |
| aagactgaag gcgcacttac tacgccatat atggctctca aaggctcagt tattgccaat | 3840 |
| tgcaagctga acatgtag atgtgcagat cccccaggta tcatatcgca aaattatgga | 3900 |
| gaagctgtgt ccttaataga taggcactca tgcaacgtct tatccttaga cgggataact | 3960 |
| ctgaggctca gtggggaatt tgatgcaacc tatcaaaaga atatctctat actagattct | 4020 |
| caagttatag tgacaggcaa tcttgatata tcaactgagc ttgggaatgt caacaactca | 4080 |
| ataagtaatg ccctgaataa gttagaggaa agcaacagca aactgacaa agtcaatgtc | 4140 |
| aaactgacca gcacatctgc tctcattacc tacatcgttt taactgtcat atctcttgtt | 4200 |
| tttggtgtac ttagcctggt tctagcatgc tacctgatgt acaagcaaaa ggcacaacaa | 4260 |
| aagaccttgt tatggcttgg gaataatacc cttgatcaga tgagagccac tacaaaaata | 4320 |
| tgagcggccg cggggatcca gacatgataa gatacattga tgagtttgga caaaccacaa | 4380 |
| ctagaatgca gtgaaaaaaa tgctttattt gtgaaatttg tgatgctatt gctttatttg | 4440 |
| taaccattat aagctgcaat aaacaagtta acaacaacaa ttgcattgat tttatgtttc | 4500 |
| aggttcaggg ggaggtgtgg gaggtttttt cggatcctct agagtcgaca attatttttat | 4560 |
| ttaataacat atagcccaaa gacctctatg aacattagt ttcccgtata ctcaacggcg | 4620 |
| cgtgtacaca cgcatctctt tgcatagcga tgaagtttgt tcggcagcag aaaatgcaga | 4680 |
| tatccaacaa tctggagaaa acttatcatc acagtggcag tggaaacata ccccctctat | 4740 |
| attcatggta taattatcgt ctacagcgtc caggatagtg gcgtgagaaa atggagatct | 4800 |
| gcagccctcc tttccatggc atgccgcttt attgttcatt aaacgcacaa tggtctcaac | 4860 |
| gccagatatg ggcatagatt ctgaagaacc cgttgacaat ccgaagaaga aggcgtgcag | 4920 |
| gtctttggaa gactcgcacg ttggtcttat aatgtgatg cgagatgtca ccctaatgcc | 4980 |
| acatggtaca ggcttatcgc ggtcatggcg atcggacttg taatttgcaa cgatgggcaa | 5040 |
| aggatcgacg acatgccaaa cattctgaac ccgtagagat gttaacgatg acgaggatga | 5100 |
| atatcccatg ctcgctgcca tagtatcaag tacaccgcga ataaggacgc gtccaacatc | 5160 |
| gttatatgca cacaatgggc tacacgtgac taacacccc gaatattagt catatgtgag | 5220 |
| tttcagtctg gctcccatat agcctgtaga ctatttgtgg tttaagtgtg aacgaggcgc | 5280 |
| tgtgaacgag actcgggccg attgtaagaa caagcaaatg cactttccat ttaacaagaa | 5340 |
| gtgtagagag aatactcaac ctctttggat gtatcctcga g | 5381 |

<210> SEQ ID NO 31
<211> LENGTH: 4600
<212> TYPE: DNA
<213> ORGANISM: artificial sequence
<220> FEATURE:
<223> OTHER INFORMATION: partial plasmid pHM119 sequence for vHVT039

<400> SEQUENCE: 31
gagctcaggg tatgatactc agctgttatt gtggccgacc aggaggactc caatgcttag      60

-continued

```
cattcataag aacgctagag atgctattta acgatgtgct gtcgtctaaa gaatttgtgc      120
atttagcctt taaatgtaaa accaatgacg cattcactac gctcgtgcgt gcaatttctg      180
ggccagggta tgcatattcc ataacagaaa tcgacacttg agaagaggat ctgactgttt      240
gggataaagg tcgtttgggt ctgtcctagc gatataattt atatgacgat atacattaaa     300
catctgtgtg cagtacttag gtatttaatc atgtcgatga aatgttatgt gtaaatatcg     360
gacaatatag ataacgggca cgctgctatt gtaacgtgcg cccgcgcgct agtgctgact     420
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca   720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaagaa aaaatcggat ggttcaatta ggacatgcat ggattctgtg cgcataaacc    1020
ataaccgcag cactgttggg cacttcggta actcaaatgc gaagcgttgc acgtctgcga    1080
taactacgcc tactatgcac attgttactc ctgcatctta aaaatatatc ctgtagtaat    1140
tttcacagca atgtcataac atcatctcgc taaagaatga cctgggattg gagaagtaat    1200
gaatatttgc aaccaatgca ttgaataaac taacattaaa cgaattccga tgtttagtca    1260
cgatagacat cggttcgccc agccgtcgaa tacagcatta tattttagtg ttgaaaatgt    1320
agggctgctt cctcacttaa aggaggaaat ggctcgattc atgtttcata gcagtagaaa    1380
aacagattgg accgtcagta agtttagagg gttttatgac tttagcacta tagataatgt    1440
aactgcggcc catcgcatgg cttggaaata tatcaaagaa ctgattttg caacagcttt    1500 attttcttct gtatttaaat gtggcgaatt gcacatctgt cgtgccgaca gtttgcagat    1560
caacagcaat ggagactatg tatggaaaaa tggaatatat ataacatatg aaaccgaata    1620
tccacttata atgattctgg ggtcagaatc aagcacttca gaaacgcaaa atatgactgc    1680
aattattgat acagatgttt tttcgttgct ttattctatt ttgcagtata tggccccgt    1740 tacggcagat caggtgcgag tagaacagat taccaacagc cacgccccca tctgacccgt    1800
ccaatattct tgtgtccctg cattttatct cacacaattt atgaacagca tcattaagat   1860
catctcactg cggccgcaag atgggctcca gatcttctac caggatcccg gtacctctaa    1920
tgctgatcat ccgaaccgcg ctgacactga gctgtatccg tctgacaagc tctcttgatg   1980
gcaggcctct tgcggctgca gggatcgtgg taacaggaga taaagcagtc aacatataca    2040
cctcatccca gacagggtca atcatagtta agttactccc gaatatgccc aaggacaaag    2100
aggtgtgtgc aaaagcccca ttggaggcat acaacaggac actgactact ttactcaccc    2160
cccttggtga ttctatccgc aggatacaag agtctgtgac tacttccgga ggaaggagac    2220
agagacgctt tataggtgcc attatcggca gtgtagctct tggggttgcg acagctgcac    2280
agataacagc agcttcggcc ctgatacaag ccaaccagaa tgctgccaac atcctccggc    2340
ttaaagagag cattgctgca accaatgaag ctgtgcacga ggtcactgac ggattatcac    2400
```

```
aactagcagt ggcagtaggg aagatgcaac agtttgtcaa tgaccagttc aataatacag    2460
cgcaagaatt ggactgtata aaaattgcac agcaggtcgg tgtagaactc aacttgtacc    2520
taactgaatt gactacagta tttgggccac aaatcacttc ccctgcctta actcagctga    2580
ctatccaagc gctttacaat ctagctggtg gtaatatgga ttacttgctg actaagttag    2640
gtgtagggaa caaccaactc agctcattaa ttggtagcgg cttgatcacc ggcaaccct a   2700 ttctgtacga ctcacagact cagatcttgg gtatacaggt aactttgcct tcagttggga    2760
acctgaataa tatgcgtgcc acctacctgg agaccttatc tgtaagcaca accaagggat    2820
ttgcctcagc acttgtccca aaagtggtga cacaggtcgg ttccgtgata aagaacttg     2880 acacctcata ctgtataggg accgacttgg atttatactg tacaagaata gtgacattcc    2940
ctatgtctcc tggtatttat tcttgtctga gcggtaatac atcggcttgc atgtattcaa    3000
agactgaagg cgcacttact acgccatata tggctctcaa aggctcagtt attgccaatt    3060
gcaagctgac aacatgtaga gtgcagatc ccccaggtat catatcgcaa aattatggag     3120
aagctgtgtc cttaatagat aggcactcat gcaacgtctt atccttagac gggataactc    3180
tgaggctcag tggggaattt gatgcaacct atcaaaagaa tatctctata ctagattctc    3240
aagttatagt gacaggcaat cttgatatat caactgagct tgggaatgtc aacaactcaa    3300
taagtaatgc cctgaataag ttagaggaaa gcaacagcaa actagacaaa gtcaatgtca    3360
aactgaccag cacatctgct ctcattacct acatcgtttt aactgtcata tctcttgttt    3420
ttggtgtact agcctggtt ctagcatgct acctgatgta caagcaaaag gcacaacaaa     3480
agaccttgtt atggcttggg aataataccc ttgatcagat gagagccact acaaaaatat    3540
gagcggccgc ggggatccag acatgataag atacattgat gagtttggac aaaccacaac    3600
tagaatgcag tgaaaaaaat gctttatttg tgaaatttgt gatgctattg ctttatttgt    3660
aaccattata agctgcaata aacaagttaa caacaacaat tgcattcatt ttatgtttca    3720
ggttcagggg gaggtgtggg aggttttttc ggatcctcta gagtcgacaa ttatttatt     3780 taataacata tagcccaaag acctctatga acatttagtt tcccgtatac tcaacggcgc    3840
gtgtacacac gcatctcttt gcatagcgat gaagtttgtt cggcagcaga aaatgcagat    3900
atccaacaat ctggagaaaa cttatcatca cagtggcagt ggaaacatac cccctctata    3960
ttcatggtat aattatcgtc tacagcgtcc aggatagtgg cgtgagaaaa tggagatctg    4020
cagccctcct ttccatggca tgccgcttta ttgttcatta aacgcacaat ggtctcaacg    4080
ccagatatgg gcatagattc tgaagaaccc gttgacaatc cgaagaagaa ggcgtgcagg    4140
tctttggaag actcgcacgt tggtcttata atgtatgatc gagatgtcac cctaatgcca    4200
catggtacag gcttatcgcg gtcatggcga tcggacttgt aatttgcaac gatgggcaaa    4260
ggatcgacga catgccaaac attctgaacc cgtagagatg ttaacgatga cgaggatgaa    4320
tatcccatgc tcgctgccat agtatcaagt acaccgcgaa taaggacgcg tccaacatcg    4380
ttatatgcac acaatgggct acacgtgact aacaccccg aatattagtc atatgtgagt     4440
ttcagtctgg ctcccatata gcctgtagac tatttgtggt ttaagtgtga acgaggcgct    4500
gtgaacgaga ctcgggccga ttgtaagaac aagcaaatgc actttccatt taacaagaag    4560
tgtagagaga atactcaacc tctttggatg tatcctcgag                          4600
```

<210> SEQ ID NO 32
<211> LENGTH: 1662
<212> TYPE: DNA
<213> ORGANISM: artificial sequence
<220> FEATURE:
<223> OTHER INFORMATION: NDV Texas F gene (wild type non-modified)

<400> SEQUENCE: 32

```
atgggctcca gatcttctac caggatcccg gtacctctaa tgctgatcat ccgaaccgcg      60
ctgacactga gctgtatccg tctgacaagc tctcttgatg caggcctct tgcggctgca      120
gggatcgtgg taacaggaga taaagcagtc aacatataca cctcatccca gacagggtca     180
atcatagtta agttactccc gaatatgccc aaggacaaag aggtgtgtgc aaaagcccca     240
ttggaggcat acaacaggac actgactact ttactcaccc cccttggtga ttctatccgc     300
aggatacaag agtctgtgac tacttccgga ggaaggagac agagacgctt tataggtgcc     360
attatcggca gtgtagctct tggggttgcg acagctgcac agataacagc agcttcggcc     420
ctgatacaag ccaaccagaa tgctgccaac atcctccggc ttaaagagag cattgctgca     480
accaatgaag ctgtgcacga ggtcactgac ggattatcac aactagcagt ggcagtaggg     540
aagatgcaac agtttgtcaa tgaccagttc aataatacag cgcaagaatt ggactgtata     600
aaaattgcac agcaggtcgg tgtagaactc aacttgtacc taactgaatt gactacagta     660
tttgggccac aaatcacttc ccctgcctta actcagctga ctatccaagc gctttacaat     720
ctagctggtg gtaatatgga ttacttgctg actaagttag gtgtagggaa caaccaactc     780
agctcattaa ttggtagcgg cttgatcacc ggcaacccta ttctgtacga ctcacagact     840
cagatcttgg gtatacaggt aactttgcct tcagttggga acctgaataa tatgcgtgcc     900
acctacctgg agaccttatc tgtaagcaca accaagggat tgcctcagc acttgtccca      960
aaagtggtga cacaggtcgg ttccgtgata aagaacttg acacctcata ctgtataggg     1020
accgacttgg atttatactg tacaagaata gtgacattcc ctatgtctcc tggtattat      1080
tcttgtctga gcggtaatac atcggcttgc atgtattcaa agactgaagg cgcacttact     1140
acgccatata tggctctcaa aggctcagtt attgccaatt gcaagctgac acatgtaga      1200
tgtgcagatc ccccaggtat catatcgcaa aattatggag aagctgtgtc cttaatagat     1260
aggcactcat gcaacgtctt atccttagac gggataactc tgaggctcag tgggggaattt     1320
gatgcaacct atcaaaagaa tatctctata ctagattctc aagttatagt gacaggcaat     1380
cttgatatat caactgagct tgggaatgtc aacaactcaa taagtaatgc cctgaataag     1440
ttagaggaaa gcaacagcaa actagacaaa gtcaatgtca aactgaccag cacatctgct     1500
ctcattacct acatcgtttt aactgtcata tctcttgttt ttggtgtact agcctggtt      1560
ctagcatgct acctgatgta caagcaaaag gcacaacaaa agaccttgtt atggcttggg     1620
aataataccc ttgatcagat gagagccact acaaaaatat ga                       1662
```

<210> SEQ ID NO 33
<211> LENGTH: 553
<212> TYPE: PRT
<213> ORGANISM: artificial sequence
<220> FEATURE:
<223> OTHER INFORMATION: NDV Texas F protein (wild type non-modified)

<400> SEQUENCE: 33

Met Gly Ser Arg Ser Ser Thr Arg Ile Pro Val Pro Leu Met Leu Ile
1               5                  10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

```
Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
                100                 105                 110

Arg Gln Arg Arg Phe Ile Gly Ala Ile Ile Gly Ser Val Ala Leu Gly
                115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
                180                 185                 190

Thr Ala Gln Glu Leu Asp Cys Ile Lys Ile Ala Gln Gln Val Gly Val
                195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Ile Leu Gly Ile Gln Val Thr
                275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
                355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
                420                 425                 430

Thr Leu Arg Leu Ser Gly Glu Phe Asp Ala Thr Tyr Gln Lys Asn Ile
                435                 440                 445

Ser Ile Leu Asp Ser Gln Val Ile Val Thr Gly Asn Leu Asp Ile Ser
    450                 455                 460
```

-continued

```
Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Ile
545                 550
```

<210> SEQ ID NO 34
<211> LENGTH: 1662
<212> TYPE: DNA
<213> ORGANISM: artificial sequence
<220> FEATURE:
<223> OTHER INFORMATION: NDV-F YZCQ wildtype DNA sequence

<400> SEQUENCE: 34

```
atgggctcca gatcttctac caggatcccg gtacctctaa tgctgatcat ccgaaccgcg      60
ctgacactga gctgtatccg tctgacaagc tctcttgatg gcaggcctct tgcggctgca     120
gggatcgtgg taacaggaga taaagcagtc aacatataca cctcatccca gacagggtca     180
atcatagtta agttactccc gaatatgccc aaggacaaag aggtgtgtgc aaaagcccca     240
ttggaggcat acaacaggac actgactact ttactcaccc cccttggtga ttctatccgc     300
aggatacaag agtctgtgac tacttccgga ggaggcaagc aaggccgcct gataggtgcc     360
attatcggca gtgtagctct tggggttgcg acagctgcac agataacagc agcttcggcc     420
ctgatacaag ccaaccagaa tgctgccaac atcctccggc ttaaagagag cattgctgca     480
accaatgaag ctgtgcacga ggtcactgac ggattatcac aactagcagt ggcagtaggg     540
aagatgcaac agtttgtcaa tgaccagttc aataatacag cgcaagaatt ggactgtata     600
aaaattgcac agcaggtcgg tgtagaactc aacttgtacc taactgaatt gactacagta     660
tttgggccac aaatcacttc ccctgcctta actcagctga ctatccaagc gctttacaat     720
ctagctggtg gtaatatgga ttacttgctg actaagttag gtgtagggaa caaccaactc     780
agctcattaa ttggtagcgg cttgatcacc ggcaacccta ttctgtacga ctcacagact     840
cagatcttgg gtatacaggt aactttgcct tcagttggga acctgaataa tatgcgtgcc     900
acctacctgg agaccttatc tgtaagcaca accaagggat ttgcctcagc acttgtccca     960
aaagtggtga cacaggtcgg ttccgtgata gaagaacttg acacctcata ctgtataggg    1020
accgacttgg atttatactg tacaagaata gtgacattcc ctatgtctcc tggtatttat    1080
tcttgtctga gcggtaatac atcggcttgc atgtattcaa agactgaagg cgcacttact    1140
acgccatata tggctctcaa aggctcagtt attgccaatt gcaagctgac aacatgtaga    1200
tgtgcagatc cccccaggtat catatcgcaa aattatggag aagctgtgtc cttaatagat    1260
aggcactcat gcaacgtctt atccttagac gggataactc tgaggctcag tggggaattt    1320
gatgcaacct atcaaaagaa tatctctata ctagattctc aagttatagt gacaggcaat    1380
cttgatatat caactgagct tgggaatgtc aacaactcaa taagtaatgc cctgaataag    1440
ttagaggaaa gcaacagcaa actagacaaa gtcaatgtca aactgaccag cacatctgct    1500
ctcattacct acatcgtttt aactgtcata tctcttgttt ttggtgtact tagcctggtt    1560
```

-continued

```
ctagcatgct acctgatgta caagcaaaag gcacaacaaa agaccttgtt atggcttggg    1620 aataatccc ttgatcagat gagagccact acaaaaatat ga                        1662
```

<210> SEQ ID NO 35
<211> LENGTH: 553
<212> TYPE: PRT
<213> ORGANISM: artificial sequence
<220> FEATURE:
<223> OTHER INFORMATION: NDV-F protein from wildtype YZCQ strain (Amino
      Acid Sequence of NDV-F of Texas strain with lentogenic cleavage
      site sequence)

<400> SEQUENCE: 35

```
Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335
```

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Leu Asp Ser Gln Val Ile Val Thr Gly Asn Leu Asp Ile Ser
450                 455                 460

Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
            515                 520                 525

Gln Lys Ala Gln Gln Lys Thr Leu Leu Trp Leu Gly Asn Asn Thr Leu
            530                 535                 540

Asp Gln Met Arg Ala Thr Thr Lys Ile
545                 550

<210> SEQ ID NO 36
<211> LENGTH: 1662
<212> TYPE: DNA
<213> ORGANISM: artificial sequence
<220> FEATURE:
<223> OTHER INFORMATION: NDV-F Texas wildtype DNA sequence

<400> SEQUENCE: 36
atgggctcta aaccttctac caggatccca gcacctctga tgctgatcac ccggattatg     60
ctgatattgg actgtatccg tccgacaagc tctcttgacg gcaggcctct tgcagctgca    120
ggaattgtag taacaggaga taaggcagtc aatgtatata cctcgtctca gacagggtca    180
atcatagtca agttgctccc gaatatgccc aaggataagg aggcgtgtgc gaaagaccca    240
ttagaggcat ataacagaac actgactact ttgctcactc ctcttggcga atccatccgc    300
aagatccaag ggtctgtgtc cacgtctgga ggaggcaagc aaggccgcct gataggtgct    360
gttattggta gtgtagctct tggggttgca acagcggcac aaataacagc agctgcggcc    420
ctaatacaag ccaaccagaa tgctgccaac atccttcggc ttaaggagag cattgctgca    480
accaatgaag ctgtgcatga agtcaccgac ggattatcac aactatcagt ggcagttggg    540
aagatgcagc agtttgtcaa tgaccagttt aataatacag cgcgagaatt ggactgtata    600
aaaatcacac aacaggttgg tgtagaactc aacctatacc taactgaatt gactacagta    660
ttcgggccac agatcacctc ccctgcatta actcagctga ccatccaggc actttataat    720
ttagctggtg gcaatatgga ttacttatta actaagttag gtataggaa caatcaactc    780

```
agctcattaa ttggcagcgg cctgatcact ggttacccta tattgtatga ctcacagact      840
caactcttgg gcatacaagt gaatttgccc tcagtcggga acttaaataa tatgcgtgcc      900
acctatttag agaccttatc tgtaagtaca gccaaaggat atgcctcagc acttgttcca      960
aaagtagtga cacaagtcgg ttctgtgata gaagagcttg cacctcata ctgtatagag      1020 tccgatctgg atttatattg tactagaata gtgacattcc ccatgtcccc aggtatttat      1080
tcctgtttaa gcggcaacac atcagcttgc atgtattcaa agactgaagg cgcactcact      1140
acgccgtata tggcccttaa aggctcagtt attgccaatt gtaagataac aacatgtaga      1200
tgtacagacc ctcctggtat catatcgcaa aattatggag aagctgtatc cctgatagat      1260
agacattcgt gcaatgtctt atcattagac gggataactc tgaggctcag tggagaattt      1320
gatgcaactt atcaaaagaa catctcaata ctagattctc aagtcatcgt gacaggcaat      1380
cttgatatat caactgaact tggaaacgtc aacaattcaa tcagcaatgc cttggataag      1440
ttggcaaaaa gcaacagcaa gctagaaaaa gtcaatgtca gactaaccag cacatccgct      1500
ctcattacct atattgttct gactgtcatt tctctagttt tcggtgcact aagtctgggt      1560
ttaacatgtt acctgatgta caaacaaaag gcacaacaaa agaccttgct atggcttggg      1620
aataataccc tcgatcagat gagagccact acaagagcat ga                       1662
```

<210> SEQ ID NO 37
<211> LENGTH: 553
<212> TYPE: PRT
<213> ORGANISM: artificial sequence
<220> FEATURE:
<223> OTHER INFORMATION: NDV-F protein from wildtype Texas strain (Amino
      Acid Sequence of NDV-F VIId wt YZCQ with lentogenic cleavage site
      sequence)

<400> SEQUENCE: 37

```
Met Gly Ser Lys Pro Ser Thr Arg Ile Pro Ala Pro Leu Met Leu Ile
1               5                   10                  15

Thr Arg Ile Met Leu Ile Leu Asp Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Lys Asp Lys Glu Ala Cys Ala Lys Asp Pro
65                  70                  75                  80

Leu Glu Ala Tyr Asn Arg Thr Leu Thr Thr Leu Leu Thr Pro Leu Gly
                85                  90                  95

Glu Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
```

```
                    195                 200                 205
Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
    290                 295                 300

Thr Leu Ser Val Ser Thr Ala Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asp Lys
465                 470                 475                 480

Leu Ala Lys Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Gly Leu Thr Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550
```

<210> SEQ ID NO 38
<211> LENGTH: 622
<212> TYPE: DNA
<213> ORGANISM: artificial sequence
<220> FEATURE:
<223> OTHER INFORMATION: MDV gB promoter

<400> SEQUENCE: 38
cgatgtttag tcacgataga catcggttcg cccagccgtc gaatacagca ttatatttta    60

```
gtgttgaaaa tgtagggctg cttcctcact taaaggagga atggctcga ttcatgtttc      120 atagcagtag aaaaacagat tggaccgtca gtaagtttag agggttttat gactttagca      180
ctatagataa tgtaactgcg gcccatcgca tggcttggaa atatatcaaa gaactgattt      240
ttgcaacagc tttattttct tctgtattta aatgtggcga attgcacatc tgtcgtgccg      300
acagtttgca gatcaacagc aatggagact atgtatggaa aaatggaata tatataacat      360
atgaaaccga atatccactt ataatgattc tggggtcaga atcaagcact tcagaaacgc      420
aaaatatgac tgcaattatt gatacagatg ttttttcgtt gctttattct attttgcagt      480
atatggcccc cgttacggca gatcaggtgc gagtagaaca gattccaac agccacgccc       540 ccatctgacc cgtccaatat tcttgtgtcc ctgcatttta tctcacacaa tttatgaaca      600
gcatcattaa gatcatctca ct                                               622

<210> SEQ ID NO 39
<211> LENGTH: 4850
<212> TYPE: DNA
<213> ORGANISM: artificial sequence
<220> FEATURE:
<223> OTHER INFORMATION: Partial plasmid SORF3-US2 gpVar-Ewtsyn sequence
      for vHVT202

<400> SEQUENCE: 39
taaaatggga tctatcatta cattcgttaa gagtctggat aattttactg tttgccagct       60
tcgatcttgg aacgtactgt ggatagtgcc ttacttggaa tcgtgaaaat tgaaacgtc       120 cattatttgg atatcttccg gttgtcccat atcccgccct ggtaccgctc ggataccttg      180
cccgtatgga ttcgtattga cagtcgcgca atcggggacc aacaacgcgt gggtccacac      240
tcattcggaa atttccgat gattctgaat atttattgcc gctcgttacg agtcgttgga       300
catatctgta atacatttct tcttctgaag gatcgctgca catttgatct atacattggc      360
caggatgttc aagtctcaga tgttgcattc tggcacagca caactttatg gcatttccga      420
tgtaatcgtc cggcagccct gggggagttc tatattcgca tattgggatg gtaaggacaa      480
tagcagatct cgcaacctcc agggaggcta ataatacgtt tttaaaggat ggatttctca      540
taaaaatctg tcgcaaatta cactgagaat atcctttact agcgccgatt gagagcatcg      600
tcgtccaatt ttctaaatgg aaagaaaaca aggcgggcaa gagtgttcca acatttttca      660
ttttcggcga atctctcaaa tcccatggcg tgcaattgat tgcaaaattg gcacttccgt      720
tcacgtttgt atctccaaac tctaagacac ttttaattga aaaactacgt tctagtgtgg      780
aaagaaacct ataggcagac catagaacta tttgacacca catatctttt tgtatgtcaa      840
actgaccatg atcgtatgtt gctgaatgca ctagggcaat tcgctcgcgc gactccatac      900
attgaataat tccacacgtc agctcatcgg ttagcaaggt ccagtagttg aagtcattta      960
tttttccccg cggctggcca aatctacctc tgggaatatc caagttgtcg aatatgatcg     1020
caccggctct ggtcatggtg aaggaacttg tagcataaag acgcaggtat catagggta      1080 atatttttt attcactcac atactaaaag taacgcatat tagcaccatg tatgggctat     1140
caattgacat ttgcgtagca ctacatcacg attatgtaca acataatggg acaacatatg     1200
cctgcaggtt agtcatatgt tacttggcag aggccgcatg gaaagtccct ggacgtggga     1260
catctgatta atacgtgagg aggtcagcca tgttcttttt ggcaaaggac tacggtcatt     1320
ggacgtttga ttggcatggg ataggqtcag ccagagttaa cagtgttctt ttggcaaagg     1380
gatacgtgga aagtcccggg ccatttacag taaactgata cggggacaaa gcacagccat     1440
```

```
atttagtcat gtattgcttg gcagagggtc tatggaaagt ccctggacgt gggacgtctg    1500
attaatatga aagaaggtca gccagaggta gctgtgtcct ttttggcaaa gggatacggt    1560
tatgggacgt ttgattggac tgggataggg tcagccagag ttaacagtgt tcttttggca    1620
aaggaaacgt ggaaagtccc gggccattta cagtaaactg atactgggac aaagtacacc    1680
catatttagt catgttcttt ttggcaaaga gcatctggaa agtcccgggc agcattatag    1740
tcacttggca gagggaaagg gtcactcaga gttaagtaca tctttccagg gccaatattc    1800
cagtaaatta cacttagttt tatgcaaatc agccacaaag gggattttcc cggtcaatta    1860 tgacttttc cttagtcatg cggtatccaa ttactgccaa attggcagta catactaggt    1920
gattcactga catttggccg tcctctggaa agtccctgga aaccgctcaa gtactgtatc    1980
atggtgactt tgcatttttg gagagcacgc cccactccac cattggtcca cgtaccctat    2040
gggggagtgg tttatgagta tataagggc tccggtttag aagccgggca gagcggccgc    2100
atgacaaacc tgcaagatca aacccaacag attgttccgt tcatacggag ccttctgatg    2160
ccaacaaccg gaccggcgtc cattccggac gacaccctgg agaagcacac tctcaggtca    2220
gagacctcga cctacaattt gactgtgggg gacacagggt cagggctaat tgtcttttc    2280 cctggattcc ctggctcaat tgtgggtgct cactacacac tgcagagcaa tgggaactac    2340
aagttcgatc agatgctcct gactgcccag aacctaccgg ccagctacaa ctactgcagg    2400
ctagtgagtc ggagtctcac agtaaggtca agcacactcc ctggtggcgt ttatgcacta    2460
aacggcacca taaacgccgt gaccttccaa ggaagcctga gtgaactgac agatgttagc    2520
tacaacgggt tgatgtctgc aacagccaac atcaacgaca aaattgggaa cgtcctagta    2580
ggggaagggg taaccgtcct cagcttaccc acatcatatg atcttgggta tgtgaggctt    2640
ggtgacccca tacccgctat agggcttgac ccaaaaatgg tagcaacatg tgacagcagt    2700
gacaggccca gagtctacac cataactgca gccgataatt accaattctc atcacagtac    2760
caaacaggtg gggtaacaat cacactgttc tcagccaaca ttgatgccat acaagtctc    2820 agcgttgggg gagagctcgt gttcaaaaca agcgtccaaa gccttgtact gggcgccacc    2880
atctacctta taggctttga tgggactgcg gtaatcacca gagctgtggc cgcaaacaat    2940
gggctgacgg ccggcatcga caatcttatg ccattcaatc ttgtgattcc aaccaatgag    3000
ataacccagc caatcacatc catcaaactg gagatagtga cctccaaaag tgatggtcag    3060 gcagggaac agatgtcatg gtcggcaagt gggagcctag cagtgacgat ccatggtggc    3120
aactatccag gagccctccg tcccgtcaca ctagtggcct acgaaagagt ggcaacagga    3180
tctgtcgtta cggtcgctgg ggtgagcaac ttcgagctga tcccaaatcc tgaactagca    3240
aagaacctgg ttacagaata tggccgattt gacccaggag ccatgaacta cacgaaattg    3300
atactgagtg agagggaccg ccttggcatc aagaccgtct ggccaacaag ggagtacact    3360
gactttcgtg agtacttcat ggaggtggcc gacctcaact ctcccctgaa gattgcagga    3420
gcatttggct tcaaagacat aatccgggcc ataaggaggt gagcggccgc gatatcaata    3480
aaatatcttt atttcatta catctgtgtg ttggttttt gtgtgaatcg atagtactaa    3540
catacgctct ccatcaaaac aaaacgaaac aaaacaaact agcaaaatag gctgtcccca    3600
gtgcaagtgc aggtgccaga acatttctct tctagacctg caggcccggg gcaagtagat    3660
gcaatttcct cacactagtt gggtttatct actattgaat tttcccctat ctgtgataca    3720
cttgggagcc tctacaagca tattgccatc atgtacgttt ttatctactg tcttaacgcc    3780
```

```
catgggaacg gaggcgtcgt cgtcatgtat tggacggcaa cataggcagc aacacaaatt    3840
gcgtttaggt ggggtgcatg tggactcgat accaagcccc tgcagctggg aacgtctgg    3900 tggagagccg ataatttgat atacgcacgc catattactg tcgttgaagt acgccttatc    3960
ttctatgttt tcaaatttag gttcccaagt ggacgtgaga agtgtttgta tctcacatgg    4020
aatggcccaa ggcattccag cccaggtgcc tggtacttta atggcaaaca aacgttttgg    4080
tagaggtatt gattctattg cagttctgca gatatctgca gccccgagta tccacaggct    4140
atacgatacg ttatcggagg cctccgattc tagcattaca tagccggtca gtagatcctg    4200
ccattcggta gcgcaaccgg ctacatcttc aaacagtctc acaataaatg catctctcgt    4260
tcctgccaat ccggaaccgg gcataccact cccgcctgcc gatttaattc tcacaattgg    4320
gcgatgccgg cggggcaaaa cgaatgtgga tttggcaaac cgacacaggt ctgctgtacg    4380
gactaatatg ggcacaccca catcattctt cagatgctcc atgcattgtt ctatgagaaa    4440
gatccatagg gtggaggcag cgtcacgaga tcgcccaggc aatcgatcgc attcgtctag    4500
taaagtgacg agagttatca tgcacacacc catgcccacg ccttccgaat aactggagct    4560
gtggaagatc ggaaacgtct ttttgactgc cggtctcgta ctactttcgc acaggtgtat    4620 accccggacgc gtactatata ttttatatca tccaacgtcc cgaaattaca tacgtggcgg    4680
cgatggaagt agatgttgag tcttcgaaag taagtgcctc gaatatgggt attgtctgtg    4740
aaaatatcga aagcggtacg acggttgcag aaccgtcgat gtcgccagat actagtaaca    4800
atagcttcga taacgaagac ttccgtgggc ctgaatacga tgtggagata              4850
```

<210> SEQ ID NO 40
<211> LENGTH: 4943
<212> TYPE: DNA
<213> ORGANISM: artificial sequence
<220> FEATURE:
<223> OTHER INFORMATION: Partial plasmid SB1US2 gpVIIdwtsyn sequence for vSB1-010

<400> SEQUENCE: 40

```
tctcgtctaa aacgctccag tgctttacag ttcgataatc tggacctggg gacgcgtata      60
ggatcgttcc tccacatgcg ctgctgtcgg tatctcgaat ccccggtatt cagttgaatc     120
gttggcggag tgtcctcctg gactctgcaa tgttccctag ccgtcttcac tatctcgtgc     180
aaggctctat aatacagttc ctctgcagac ccgtcgttgc tcttcccttc tgcgtcgtta     240
gttatttctg taggctccag acgatttgcc tgcatttgtg cgcaacataa tctgattgca     300
ttccctatct cgtcttccgg taatcccata ggtgttcggt attcgcagat aggtagagaa     360
agcaccactg caaatcgtgc aatttccatt gccccaacca atatttttt taagaacggc     420 atcgccgtta atgtacctcg ggcattgtga cgatcgaaac ccttatggat gcctaaagag     480
agcattgcgg tccagttctc caggtgaaaa gagaatagcg cgggtagaaa cgggccgatt     540
agttttatct tcgccgcgtc cctaatatcc caagttctgc agtataactt ccatcgtccg     600
ttttcgacaa ggtccggcgc gacatagttt gaaatgtcat ctatcagaaa catctcgccc     660
atcgtagaaa aaaacctgta cgcagaccat aaaaccattc ggtaccacat atccttgtgt     720
atatcaaacg atatgttggt tatgtcgttg gcggatgttg tatgaaatag agctaagcgt     780
tctctggatt ccacgcactg aacgattccg ttagtcaatt catctgctaa cataggccaa     840
aagtttattc gtgttacttt tctcggcggt ttggcaaaac gccccttgg cacatccatg      900 tcattaaata cagcggcata actcctactc atgtgttcca tagcccaggt ttctgttcgg     960
```

```
tctgctacta cgatcagatc agtggcgcga tcagatgcgt gggatgaatg aagtgtatcc    1020
gaaagcagtt ttgagatata cgctaaactg tacgacgatt gtggcactaa acgaagcttt    1080
gcgcgacccc catcccacgc cctgcaggtt agtcatatgt tacttggcag aggccgcatg    1140
gaaagtccct ggacgtggga catctgatta atacgtgagg aggtcagcca tgttcttttt    1200
ggcaaaggac tacggtcatt ggacgtttga ttggcatggg atagggtcag ccagagttaa    1260
cagtgttctt ttggcaaagg gatacgtgga aagtcccggg ccatttacag taaactgata    1320
cggggacaaa gcacagccat atttagtcat gtattgcttg gcagagggtc tatggaaagt    1380
ccctggacgt gggacgtctg attaatatga agaaggtca gccagaggta gctgtgtcct    1440
ttttggcaaa gggatacggt tatgggacgt ttgattggac tgggataggg tcagccagag    1500
ttaacagtgt tcttttggca aggaaacgt ggaaagtccc gggccattta cagtaaactg    1560
atactgggac aaagtacacc catatttagt catgttcttt ttggcaaaga gcatctggaa    1620
agtcccgggc agcattatag tcacttggca gagggaaagg gtcactcaga gttaagtaca    1680
tctttccagg gccaatattc cagtaaatta cacttagttt tatgcaaatc agccacaaag    1740
gggattttcc cggtcaatta tgactttttc cttagtcatg cggtatccaa ttactgccaa    1800
attggcagta catactaggt gattcactga catttggccg tcctctggaa agtccctgga    1860
aaccgctcaa gtactgtatc atggtgactt tgcattttg gagagcacgc cccactccac    1920
cattggtcca cgtaccctat ggggagtgg tttatgagta tataagggc tccggtttag    1980 aagccgggca gagcggccgc atgggctcca aaccttctac caggatccca gcacctctga    2040
tgctgatcac ccggattatg ctgatattgg gctgtatccg tccgacaagc tctcttgacg    2100
gcaggcctct tgcagctgca ggaattgtag taacaggaga taaggcagtc aatgtataca    2160
cttcgtctca gacagggtca atcatagtca agttgctccc gaatatgccc agggataagg    2220
aggcgtgtgc aaaagcccca ttagaggcat ataacagaac actgactact tgctcactc    2280 ctcttggcga ctccatccgc aagatccaag ggtctgtgtc cacatctgga ggaggcaagc    2340
aaggccgcct gataggtgct gttattggca gtgtagctct tggggttgca acagcggcac    2400
agataacagc agctgcggcc ctaatacaag ccaaccagaa tgccgccaac atcctccggc    2460
ttaaggagag cattgctgca accaatgaag ctgtgcatga agtcaccgac ggattatcac    2520
aactatcagt ggcagttggg aagatgcagc agtttgtcaa tgaccagttt aataatacgg    2580
cgcgagaatt ggactgtata aaaatcacac aacaggttgg tgtagaactc aacctatacc    2640
taactgaatt gactacagta ttcgggccac agatcacctc ccctgcatta actcagctga    2700
ccatccaggc actttataat ttagctggtg gcaatatgga ttacttatta actaagttag    2760 gtataggaa caatcaactc agctcgttaa ttggtagcgg cctgatcact ggttacccta    2820
tactgtatga ctcacagact caactcttgg gcatacaagt gaatttaccc tcagtcggga    2880
acttaaataa tatgcgtgcc acctatttgg agaccttatc tgtaagtaca accaaaggat    2940
atgcctcagc acttgtcccg aaagtagtga cacaagtcgg ttccgtgata gaagagcttg    3000
acacctcata ctgtatagag tccgatctgg atttatattg tactagaata gtgacattcc    3060
ccatgtcccc aggtatttat tcctgtttga gcggcaacac atcagcttgc atgtattcaa    3120
agactgaagg cgcactcact acgccgtata tggcccttaa aggctcagtt attgccaatt    3180
gtaaaataac aacatgtaga tgtacagacc ctcctggtat catatcgcaa aattatggag    3240
aagctgtatc cctgatagat agacattcgt gcaatgtctt atcattagac gggataactc    3300
taaggctcag tggggaattt gatgcaactt atcaaaagaa catctcaata ctagattctc    3360
```

```
aagtcatcgt gacaggcaat cttgatatat caactgaact tggaaacgtc aacaattcaa    3420
tcagcaatgc cttggatagg ttggcagaaa gcaacagcaa gctagaaaaa gtcaatgtca    3480
gactaaccag cacatctgct ctcattacct atattgttct aactgtcatt tctctagttt    3540
tcggtgcact tagtctggtg ttagcgtgtt acctgatgta caaacagaag gcacaacaaa    3600
agaccttgct atggcttggg aataatacccc tcgatcagat gagagccact acaagagcat    3660
gagcggccgc gatatcaata aaatatcttt attttcatta catctgtgtg ttggttttt     3720 gtgtgaatcg atagtactaa catacgctct ccatcaaaac aaaacgaaac aaaacaaact    3780
agcaaaatag gctgtcccca gtgcaagtgc aggtgccaga acatttctct tctagacctg    3840
caggggagtc tgtgcaaggt taatgaccct cgcagttcat tcggaagtta taactgccgc    3900
cttcgcacat ttcttttgt cctgttttgt attgccataa cagataggaa ttgaaacctg     3960
atcctcctgt tttttgcagc atggccagca acagaatact ttgtcggatc gactacttgc    4020
gcgagatggt tccgttcttg gaggtttcgg cgggtcgggt ggagaaccta ttattttata    4080
cacacacgtc ataccgttgt cgcgaaaatg ttctttgtct tctgccgtct cgaacgtcgg    4140
ttcccacgta gacgttagga gcgttggaat ggtatcagga agagcccacg gcatgccgga    4200
ccaagtaccc gctactttga ccgcgagcag tctcttcggt aatgggatgt attccagagc    4260
agcgcggcag agatcagcgg ccccccactat ccacagactg tatgaagtgt tttctgaaac   4320
atcggactcc aacatcaaat atccagacat aacatcttgc cattcggaag cacatccgcc    4380
gacatcttca aatagcctaa ctataaacga gtctctagtt cctgctaacc cagtacctcg    4440
aatgccagtc ccatccggtg ggttcgtcct gataatcggt ctctgacgcc gaggaagaac    4500
taaaaggggt ctggaaaagc ggaacagatc tgcagaccga acgactacag acacgcccac    4560
atcatcatgt atctgttcca tgcattgctt tatgagaaaa atccataagg ccgaggcggc    4620
atctctagat ctcccgggga gtctctcgca ctcatctagg agagtgacga cagttatcat    4680
agacacgccc atttgtgcac caaacgaaaa gttcctgtac tggtggagcg tcggcgcggg    4740
aatcggtccg tgctctgaaa ccagtgtcta gacagaagac catccggtaa attctggtgt    4800
atgaactgac ggtctccaga cgaacgtcga agacattaac gatggaaact aacgagcttt    4860
cttcaaaagt gtctgattac aacgctaata gaccttacga aactatacgc agcgatacca    4920
gtgacacaga tccgtcggtg tcg                                            4943
```

<210> SEQ ID NO 41
<211> LENGTH: 1362
<212> TYPE: DNA
<213> ORGANISM: artificial sequence
<220> FEATURE:
<223> OTHER INFORMATION: IBDV DNA encoding VP2 protein of IBDV E strain

<400> SEQUENCE: 41

```
atgacaaacc tgcaagatca aacccaacag attgttccgt tcatacggag ccttctgatg     60
ccaacaaccg gaccggcgtc cattccggac gacaccctgg agaagcacac tctcaggtca    120
gagacctcga cctacaattt gactgtgggg gacacagggt cagggctaat tgtcttttc     180 cctggattcc ctggctcaat tgtgggtgct cactacacac tgcagagcaa tgggaactac    240
aagttcgatc agatgctcct gactgcccag aacctaccgg ccagctacaa ctactgcagg    300
ctagtgagtc ggagtctcac agtaaggtca agcacactcc ctggtggcgt ttatgcacta    360
aacggcacca taaacgccgt gacccttcca ggaagcctga gtgaactgac agatgttagc    420
```

```
tacaacgggt tgatgtctgc aacagccaac atcaacgaca aaattgggaa cgtcctagta    480
ggggaagggg taaccgtcct cagcttaccc acatcatatg atcttgggta tgtgaggctt    540
ggtgacccca tacccgctat agggcttgac ccaaaaatgg tagcaacatg tgacagcagt    600
gacaggccca gagtctacac cataactgca gccgataatt accaattctc atcacagtac    660
caaacaggtg gggtaacaat cacactgttc tcagccaaca ttgatgccat cacaagtctc    720
agcgttgggg gagagctcgt gttcaaaaca agcgtccaaa gccttgtact gggcgccacc    780
atctacctta taggctttga tgggactgcg gtaatcacca gagctgtggc cgcaaacaat    840
gggctgacgg ccggcatcga caatcttatg ccattcaatc ttgtgattcc aaccaatgag    900
ataacccagc caatcacatc catcaaactg gagatagtga cctccaaaag tgatggtcag    960
gcaggggaac agatgtcatg gtcggcaagt gggagcctag cagtgacgat ccatggtggc   1020
aactatccag gagccctccg tcccgtcaca ctagtggcct acgaaagagt ggcaacagga   1080
tctgtcgtta cggtcgctgg ggtgagcaac ttcgagctga tcccaaatcc tgaactagca   1140
aagaacctgg ttacagaata tggccgattt gacccaggag ccatgaacta cacgaaattg   1200
atactgagtg agagggaccg ccttggcatc aagaccgtct ggccaacaag ggagtacact   1260
gactttcgtg agtacttcat ggaggtggcc gacctcaact ctcccctgaa gattgcagga   1320
gcatttggct tcaaagacat aatccggggcc ataaggaggt ga                     1362
```

<210> SEQ ID NO 42
<211> LENGTH: 453
<212> TYPE: PRT
<213> ORGANISM: artificial sequence
<220> FEATURE:
<223> OTHER INFORMATION: IBDV VP2 protein of IBDV E strain

<400> SEQUENCE: 42

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
```

```
                195                 200                 205
Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450

<210> SEQ ID NO 43
<211> LENGTH: 884
<212> TYPE: DNA
<213> ORGANISM: artificial sequence
<220> FEATURE:
<223> OTHER INFORMATION: Guinea pig CMV promoter

<400> SEQUENCE: 43
ttagtcatat gttacttggc agaggccgca tggaaagtcc ctggacgtgg gacatctgat      60
taatacgtga ggaggtcagc catgttcttt ttggcaaagg actacggtca ttggacgttt    120
gattggcatg ggatagggtc agccagagtt aacagtgttc ttttggcaaa gggatacgtg    180
gaaagtcccg ggccatttac agtaaactga tacgggggaca aagcacagcc atatttagtc    240
atgtattgct tggcagaggg tctatggaaa gtccctggac gtgggacgtc tgattaatat    300
gaaagaaggt cagccagagg tagctgtgtc ttttttggca aagggatacg gttatgggac    360
gtttgattgg actgggatag gtcagccag agttaacagt gttctttttgg caaaggaaac    420 gtggaaagtc ccgggccatt tacagtaaac tgatactggg acaaagtaca cccatattta    480
gtcatgttct ttttgcaaa gagcatctgg aaagtcccgg gcagcattat agtcacttgg    540
cagagggaaa gggtcactca gagttaagta catctttcca gggccaatat tccagtaaat    600
```

```
tacacttagt tttatgcaaa tcagccacaa aggggatttt cccggtcaat tatgactttt      660
tccttagtca tgcggtatcc aattactgcc aaattggcag tacatactag gtgattcact      720
gacatttggc cgtcctctgg aaagtccctg gaaaccgctc aagtactgta tcatggtgac      780
tttgcatttt tggagagcac gccccactcc accattggtc cacgtaccct atgggggagt      840
ggtttatgag tatataaggg gctccggttt agaagccggg caga                      884

<210> SEQ ID NO 44
<211> LENGTH: 30
<212> TYPE: DNA
<213> ORGANISM: artificial sequence
<220> FEATURE:
<223> OTHER INFORMATION: primer HM101

<400> SEQUENCE: 44
ccggaattcc gatgtttagt cacgatagac                                       30

<210> SEQ ID NO 45
<211> LENGTH: 35
<212> TYPE: DNA
<213> ORGANISM: artificial sequence
<220> FEATURE:
<223> OTHER INFORMATION: Primer HM102

<400> SEQUENCE: 45
ataagagcgg ccgcagtgag atgatcttaa tgatg                                 35

<210> SEQ ID NO 46
<211> LENGTH: 38
<212> TYPE: DNA
<213> ORGANISM: artificial sequence
<220> FEATURE:
<223> OTHER INFORMATION: primer F-ATG

<400> SEQUENCE: 46
tatagcggcc gcaagatggg ctccagatct tctaccag                              38

<210> SEQ ID NO 47
<211> LENGTH: 34
<212> TYPE: DNA
<213> ORGANISM: artificial sequence
<220> FEATURE:
<223> OTHER INFORMATION: Primer F-STOP

<400> SEQUENCE: 47
cgaggcggcc gctcatattt ttgtagtggc tctc                                  34
```